US006815443B2

(12) United States Patent
Buschmann et al.

(10) Patent No.: US 6,815,443 B2
(45) Date of Patent: Nov. 9, 2004

(54) 5-AMINO-1-PENTENE-3-OL SUBSTITUTED DERIVATIVES

(75) Inventors: Helmut Buschmann, Aachen (DE); Corinna Maul, Aachen (DE); Bernd Sundermann, Aachen (DE); Utz-Peter Jagusch, Aachen (DE); Michael Haurand, Aachen (DE); Boris Chizh, Aachen (DE)

(73) Assignee: Gruenenthal GmbH, Aachen (DE)

( * ) Notice: Subject to any disclaimer, the term of this patent is extended or adjusted under 35 U.S.C. 154(b) by 18 days.

(21) Appl. No.: 10/402,259

(22) Filed: Mar. 31, 2003

(65) Prior Publication Data

US 2003/0220390 A1 Nov. 27, 2003

Related U.S. Application Data

(63) Continuation of application No. PCT/EP01/11244, filed on Sep. 28, 2001.

(30) Foreign Application Priority Data

Sep. 30, 2000 (DE) ........................................ 100 48 714

(51) Int. Cl.[7] .................... A61K 31/045; A61K 31/495; C07D 241/04; C07D 333/20; C07D 205/02

(52) U.S. Cl. .................. 514/252.12; 514/438; 514/724; 544/336; 549/74; 568/704; 568/705

(58) Field of Search ............................ 514/252.12, 438, 514/724; 544/336; 549/74; 568/704, 705

(56) References Cited

U.S. PATENT DOCUMENTS

| | | | |
|---|---|---|---|
| 3,974,157 A | 8/1976 | Shetty et al. | 260/247.2 B |
| 4,686,309 A | 8/1987 | Barriere et al. | 564/355 |

FOREIGN PATENT DOCUMENTS

| | | |
|---|---|---|
| CH | 500 162 | 1/1971 |
| DE | 239 403 A5 | 9/1986 |
| GB | 1117226 | 6/1968 |
| GB | 2 323 594 A | 9/1998 |
| WO | 99/37296 | 7/1999 |
| WO | 00/02545 | 1/2000 |
| WO | 00/15611 | 3/2000 |

*Primary Examiner*—Taofiq Solola
(74) *Attorney, Agent, or Firm*—Crowell & Moring LLP

(57) ABSTRACT

The invention relates to 5-amino-1-pentene-3-ol substituted derivatives, a method for the production thereof, medicaments containing said compounds, the use of substituted 5-amino-1-pentene-3-ol derivatives for the production of medicaments, and methods of treatment using the medicaments.

34 Claims, No Drawings

5-AMINO-1-PENTENE-3-OL SUBSTITUTED DERIVATIVES

CROSS REFERENCE TO RELATED APPLICATIONS

The present application is a continuation of International Patent Application No. PCT/EP01/11244, filed Sep. 28, 2001, designating the United States of America and published in German as WO 02/30869, the entire disclosure of which is incorporated herein by reference. Priority is claimed based on Federal Republic of Germany Patent Application No. 100 48 714.9, filed Sep. 30, 2000.

BACKGROUND AND SUMMARY OF THE INVENTION

The present invention relates to substituted 5-amino-1-penten-3-ol derivatives, a process for their production, medicaments containing these compounds, and the use of substituted 5-amino-1-penten-3-ol derivatives for the production of medicaments.

The cyclic GABA (gamma-aminobutyric acid) analog gabapentin is a clinically tested antiepileptic. Gabapentin exhibits further interesting, medically relevant properties, in particular as an analgesic. New structure classes that exhibit an affinity for the gabapentin binding site are therefore of interest. There is therefore a further need for substances that exhibit similar properties to those of gabapentin, for example the analgesic action.

The treatment of chronic and non-chronic pain conditions is of great importance in medicine. There is therefore a universal need for highly effective pain treatments. The urgent practical need for a patient-oriented and targeted treatment of chronic and non-chronic pain conditions, which in the present context is understood to mean the successful and satisfactory treatment of pain in the patient, is documented by the large number of scientific publications that have recently appeared in the field of applied analgesics and in basic research on nociception.

Conventional opioids such as morphine are highly effective in the treatment of severe to extremely severe pain. Their use is however limited due to their known side effects, for example respiratory depression, nausea, sedation, constipation and development of tolerance. Also, they are less effective in treating neuropathic or incidental pain, from which tumor patients in particular suffer.

DESCRIPTION OF THE INVENTION

The object of the invention was accordingly to discover new structures that exhibit an affinity for the gabapentin binding site and/or exhibit corresponding physiological activities, for example as regards analgesia.

The present invention accordingly provides substituted 5-amino-1-penten-3-ol derivatives of the general formula I,

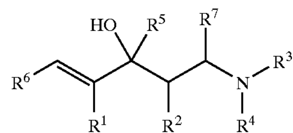

I wherein $R^1$ and $R^2$ in each case independently of one another are selected from $C_{1-6}$ alkyl, branched or unbranched, saturated or unsaturated, unsubstituted or singly or multiply substituted, or $R^1$ and $R^2$ together form a $(CH_2)_{2-9}$ ring that may optionally be substituted by $C_{1-8}$ alkyl, branched or unbranched, saturated or unsaturated, unsubstituted or singly or multiply substituted, or by aryl, unsubstituted or singly or multiply substituted, $R^3$ and $R^4$ in each case independently of one another are selected from $C_{1-6}$ alkyl, branched or unbranched, saturated or unsaturated, unsubstituted or singly or multiply substituted, from $C_{3-6}$ cycloalkyl, saturated or unsaturated, unsubstituted or singly or multiply substituted, or from phenyl, benzyl or phenethyl, unsubstituted or singly or multiply substituted or the radicals $R^3$ and $R^4$ together form a ring and denote $CH_2CH_2OCH_2CH_2$, $CH_2CH_2NR^{22}CH_2CH_2$ or $(CH_2)_{3-6}$, where $R^{22}$ is selected from H; $C_{1-10}$ alkyl or $C_{3-10}$ cycloalkyl that is in each case saturated or unsaturated, branched or unbranched, singly or multiply substituted or unsubstituted; aryl or heteroaryl, in each case singly or multiply substituted or unsubstituted; or aryl bound via $C_{1-3}$ alkyl that is saturated or unsaturated, $C_{3-10}$ cycloalkyl or heteroaryl, in each case singly or multiply substituted or unsubstituted, $R^5$ is selected from $C_{1-10}$ alkyl, saturated or unsaturated, branched or unbranched, singly or multiply substituted or unsubstituted, from $C_{3-9}$ cycloalkyl, saturated or unsaturated, from aryl, heteroaryl, aryl bound via saturated or unsaturated $C_{1-3}$ alkyl, from $C_{3-10}$ cycloalkyl bound via saturated or unsaturated $C_{1-3}$ alkyl, or from heteroalkyl bound via saturated or unsaturated $C_{1-3}$ alkyl, wherein all aryl, heteroaryl and cycloalkyl radicals may in each case independently of one another be unsubstituted or may be singly or multiply substituted with radicals selected independently of one another from F, Cl, Br, I, $OR^{18}$, $SR^{18}$, $SO_2R^{18}$, $SO_2OR^{18}$, CN, $COOR^{18}$, $NR^{19}R^{20}$; $C_1$–$C_{10}$ alkyl, saturated or unsaturated, branched or unbranched, singly or multiply substituted or unsubstituted; $C_{3-9}$ cycloalkyl, saturated or unsaturated, unsubstituted or singly or multiply substituted; aryl or heteroaryl, in each case unsubstituted or singly or multiply substituted; or from aryl, $C_{3-9}$ cycloalkyl or heteroaryl bound via saturated or unsaturated $C_{1-3}$ alkyl, and may in each case be unsubstituted or singly or multiply substituted, where $R^{18}$ is selected from H; $C_{1-10}$ alkyl, saturated or unsaturated, branched or unbranched, unsubstituted or singly or multiply substituted; $C_{3-9}$ cycloalkyl, saturated or unsaturated, unsubstituted or singly or multiply substituted; aryl or heteroaryl, unsubstituted or singly or multiply substituted; or aryl, $C_{3-9}$ cycloalkyl or heteroaryl bound via saturated or unsaturated $C_{1-3}$ alkyl and in each case unsubstituted or singly or multiply substituted; and $R^{19}$ and $R^{20}$ independently of one another are selected from H; $C_{1-10}$ alkyl, saturated or unsaturated, branched or unbranched, unsubstituted or singly or multiply substituted; $C_{3-9}$ cycloalkyl, saturated or unsaturated, unsubstituted or singly or multiply substituted; aryl or heteroaryl, in each case unsubstituted or singly or multiply substituted; or from aryl, $C_{3-9}$ cycloalkyl or heteroaryl bound via saturated or unsaturated $C_{1-3}$ alkyl and in each case unsubstituted or singly or multiply substituted;

or $R^{19}$ and $R^{20}$ together form $CH_2CH_2OCH_2CH_2$, $CH_2CH_2NR^{21}CH_2CH_2$ or $(CH_2)_{3-6}$, where $R^{21}$ is selected from H; phenyl, substituted or unsubstituted; $C_{1-10}$ alkyl saturated or unsaturated, branched or unbranched, unsubstituted or singly or multiply substituted;

and $R^6$ is selected from $C_{1-10}$ alkyl, saturated or unsaturated, branched or unbranched, singly or multiply substituted or unsubstituted; or from $C_{5-7}$ cycloalkyl, aryl or heteroaryl, in each case unsubstituted or singly or multiply substituted;

$R^7$ is selected from H; aryl or heteroaryl; in each case unsubstituted or singly or multiply substituted;

optionally in the form of their racemates, their pure stereoisomers, in particular enantiomers or diastereomers, or in the form of mixtures of the stereoisomers, in particular of the enantiomers or diastereomers, in an arbitrary mixture ratio; in the specified form or in the form of their acids or their bases or in the form of their salts, in particular of physiologically acceptable salts or in the form of their solvates, in particular hydrates.

The substances according to the invention bind to the gabapentin binding site and exhibit an excellent analgesic effect.

Within the context of the present invention alkyl and cycloalkyl radicals are understood to mean saturated and unsaturated (but not aromatic), branched, unbranched and cyclic hydrocarbons, which may be unsubstituted or singly or multiply substituted. In this connection $C_{1-2}$ alkyl denotes $C_1$ or $C_2$ alkyl, $C_{1-3}$ alkyl denotes $C_1$, $C_2$ or $C_3$ alkyl, $C_{1-4}$ alkyl denotes $C_1$, $C_2$, $C_3$ or $C_4$ alkyl, $C_{1-5}$ alkyl denotes $C_1$, $C_2$, $C_3$, $C_4$ or $C_5$ alkyl, $C_{1-6}$ alkyl denotes $C_1$, $C_2$, $C_3$, $C_4$, $C_5$ or $C_6$ alkyl, $C_{1-7}$ alkyl denotes $C_1$, $C_2$, $C_3$, $C_4$, $C_5$, $C_6$ or $C_7$ alkyl, $C_{1-8}$ alkyl denotes $C_1$, $C_2$, $C_3$, $C_4$, $C_5$, $C_6$, $C_7$ or $C_8$ alkyl, $C_{1-10}$ alkyl denotes $C_1$, $C_2$, $C_3$, $C_4$, $C_5$, $C_6$, $C_7$, $C_8$, $C_9$ or $C_{10}$ alkyl, $C_{1-18}$ alkyl denotes $C_1$, $C_2$, $C_3$, $C_4$, $C_5$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$ or $C_{18}$ alkyl. Also, $C_{3-4}$ cycloalkyl denotes $C_3$ or $C_4$ cycloalkyl, $C_{3-5}$ cycloalkyl denotes $C_3$, $C_4$ or $C_5$ cycloalkyl, $C_{3-6}$ cycloalkyl denotes $C_3$, $C_4$, $C_5$ or $C_6$ cycloalkyl, $C_{3-7}$ cycloalkyl denotes $C_3$, $C_4$, $C_5$, $C_6$ or $C_7$ cycloalkyl, $C_{3-8}$ cycloalkyl denotes $C_3$, $C_4$, $C_5$, $C_6$, $C_7$ or $C_8$ cycloalkyl, $C_{4-5}$ cycloalkyl denotes $C_4$ or $C_5$ cycloalkyl, $C_{4-6}$ cycloalkyl denotes $C_4$, $C_5$ or $C_6$ cycloalkyl, $C_{4-7}$ cycloalkyl denotes $C_4$, $C_5$, $C_6$ or $C_7$ cycloalkyl, $C_{5-6}$ cycloalkyl denotes $C_5$ or $C_6$ cycloalkyl and $C_{5-7}$ cycloalkyl denotes $C_5$, $C_6$ or $C_7$ cycloalkyl. With regard to cycloalkyl the term also includes saturated cycloalkyls in which one or two carbon atoms are replaced by a heteroatom, namely S, N or O. The term cycloalkyl furthermore also includes in particular singly or multiply, preferably singly, unsaturated cycloalkyls without a heteroatom in the ring as long as the cycloalkyl does not form an aromatic system. The alkyl and cycloalkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, but also adamantyl, $CH_2F$, $CHF_2$, $CF_3$ or $CH_2OH$ as well as pyrazolinone, oxopyrazolinone, [1,4] dioxane or dioxolane.

In connection with alkyl and cycloalkyl, the term "substituted" within the context of the present invention—as long as it is not specifically defined otherwise—is understood to mean the substitution of at least one hydrogen atom(s) by F, Cl, Br, I, $NH_2$, SH or OH, and the term "multiply substituted" or "substituted" in the case of multiple substitution is understood to mean that the substitution occurs on various atoms as well as on the same atoms multiply with the same or different substituents, for example triply on the same C atom as in the case of $CF_3$, or at various positions as in the case of —CH(OH)—CH═CH—$CHCl_2$. Particularly preferred substituents in this case are F, Cl and OH. With regard to cycloalkyl, the hydrogen atom may also be replaced by $OC_{1-3}$ alkyl or $C_{1-3}$ alkyl (each singly or multiply substituted or unsubstituted), in particular methyl, ethyl, n-propyl, i-propyl, $CF_3$, methoxy or ethoxy.

The term $(CH_2)_{3-6}$ is understood to denote —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, and the term $(CH_2)_{1-4}$ is understood to denote —$CH_2$—, —$CH_2$—$CH_2$—, —$CH_2$—$CH_2$—$CH_2$— and —$CH_2$—$CH_2$—$CH_2$—$CH_2$—, etc.

The term aryl radical is understood to mean ring systems with at least one aromatic ring, but without heteroatoms in any of the rings. Examples are phenyl, naphthyl, fluoranthenyl, fluoroenyl, tetralinyl or indanyl, in particular 9H-fluorenyl or anthracenyl radicals, which may be unsubstituted or singly or multiply substituted.

The term heteroaryl radical is understood to mean heterocyclic ring systems with at least one unsaturated ring that may contain one or more heteroatoms from the group of nitrogen, oxygen and/or sulfur, and which may also be singly or multiply substituted. Examples from the group of heteroaryl compounds are furan, benzofuran, thiophene, benzothiophene, pyrrole, pyridine, pyrimidine, pyrazine, quinoline, isoquinoline, phthalazine, benxo-1,2,5-thiadiazole, benzothiazole, indole, benzotriazole, benzodioxolane, benzodioxane, carbazole, indole and quinazoline.

In connection with aryl and heteroaryl the term substituted is understood to mean—unless expressly defined otherwise—the substitution of the aryl or heteroaryl by $R^{23}$, $OR^{23}$, a halogen, preferably F and/or Cl, a $CF_3$, a CN, an $NO_2$, an $NR^{24}R^{25}$, a $C_{1-6}$ alkyl (saturated), a $C_{1-6}$ alkoxy, a $C_{3-8}$ cycloalkoxy, a $C_{3-8}$ cycloalkyl or a $C_{2-6}$ alkylene.

In this connection the radical $R^{23}$ denotes H, a $C_{1-10}$ alkyl radical, preferably a $C_{1-6}$ alkyl, an aryl or heteroaryl, or an aryl or heteroaryl radical bound via $C_{1-3}$ alkyl, saturated or unsaturated, or a $C_{1-3}$ alkylene group, wherein these aryl and heteroaryl radicals themselves are not substituted by aryl or heteroaryl radicals, the radicals $R^{24}$ and $R^{25}$, which may be the same or different, denote H, a $C_{1-10}$ alkyl, preferably a $C_{1-6}$ alkyl, an aryl, a heteroaryl or an aryl or heteroaryl radical bound via $C_{1-3}$ alkyl, saturated or unsaturated, or a $C_{1-3}$ alkylene group, wherein these aryl and heteroaryl radicals themselves are not substituted by aryl or heteroaryl radicals, or the radicals $R^{24}$ and $R^{25}$ together denote $CH_2CH_2OCH_2CH_2$, $CH_2CH_2NR^{26}CH_2$—$CH_2$ or $(CH_2)_{3-6}$, and the radical $R^{26}$ denotes H, a $C_{1-10}$ alkyl, preferably a $C_{1-6}$ alkyl, an aryl or heteroaryl radical or an aryl or heteroaryl radical bound via $C_{1-3}$ alkyl, saturated or unsaturated, or a $C_{1-3}$ alkylene group, wherein these aryl and heteroaryl radicals themselves are not substituted by aryl or heteroaryl radicals.

The term salt is understood to denote any form of the compound according to the invention in which the latter adopts an ionic form or is charged and is coupled to a counterion (a cation or anion) or is in dissolved form. The term is also understood to include complexes of the active constituent with other molecules and ions, in particular complexes that are complexed via ionic interactions. In particular this is understood to mean physiologically acceptable salts with cations or bases and physiologically acceptable salts with anions or acids.

The term physiologically acceptable salt with cations or bases is understood to mean, within the context of the present invention, salts of at least one of the compounds according to the invention—generally of a (deprotonated) acid—as anion with at least one, preferably inorganic cation, that are physiologically acceptable, especially when administered to humans or other mammals. Particularly preferred are the salts of alkali metals and alkaline earth metals as well as of $NH_4^+$, especially the (mono) or (di) sodium, (mono) or (di) potassium, magnesium or calcium salts.

The term physiologically acceptable salt with anions or acids is understood within the context of the present invention to mean salts of at least one of the compounds according to the invention—generally protonated, for example on nitrogen—as cation with at least one physiologically acceptable anion, especially when administered to humans and other mammals. In particular the salt formed with a physiologically acceptable acid is understood within the context of the present invention to mean salts with inorganic or organic acids that are physiologically acceptable, when administered to humans and other mammals. Examples of physiologically acceptable salts of specific acids are salts of hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydro1$\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, $\alpha$-liponic acid, acetylglycine, acetylsalicylic acid, hippuric acid and/or aspartic acid. Particularly preferred is the hydrochloride or dihydrochloride salt.

In a preferred embodiment of the invention, in the substituted 5-amino-1-penten-3-ol derivatives according to formula I $R^7$ is selected from H or heteroaryl or is a radical according to formula II,

II

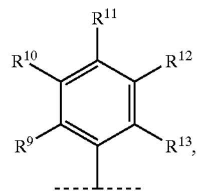

where $R^9$ to $R^{13}$ in each case independently of one another are selected from H, F, Cl, Br, I, $CF_3$, $CHF_2$, $CH_2F$, OH, $OR^{14}$, $OCF_3$, $OCHF_2$, $OCH_2F$, $SR^{14}$, $SO_2CH_3$, $SO_2CF_3$; $C_{1-6}$ alkyl, branched or unbranched, saturated or unsaturated, unsubstituted or singly or multiply substituted; phenyl, unsubstituted or singly or multiply substituted; CN, $COOR^{14}$, $NO_2$ or $R^9$ and $R^{10}$, or $R^{10}$ and $R^{11}$ together form an $OCH_2O$ or $OCH_2CH_2O$ ring, and $R^{14}$ is selected from $C_{1-6}$ alkyl, branched or unbranched, saturated or unsaturated, unsubstituted or singly or multiply substituted; or from phenyl, benzyl, phenethyl or thiophene, in each case unsubstituted or singly or multiply substituted.

More preferably, $R^7$is hydrogen.

In a preferred embodiment of the invention, in the substituted 5-amino-1-penten-3-ol derivatives of formula I $R^1$ and $R^2$ together form a $(CH_2)_{2-5}$ ring that may optionally be substituted with $C_{1-6}$ alkyl, branched or unbranched, saturated or unsaturated, unsubstituted or singly or multiply substituted; or phenyl, unsubstituted or singly or multiply substituted, though the said ring is preferably unsubstituted, and wherein $R^1$ and $R^2$ preferably together form an unsubstituted $(CH_2)_{2-4}$ ring or $R^1$ and $R^2$ independently of one another are selected from $C_{1-3}$ alkyl, unbranched, saturated and unsubstituted, preferably $CH_3$, and in particular $R^1$ and $R^2$ both denote $CH_3$.

In a further preferred embodiment of the invention, in the substituted 5-amino-1-penten-3-ol derivatives of formula I $R^3$ and $R^4$ in each case independently of one another are selected from $C_{1-6}$ alkyl, branched or unbranched, saturated or unsaturated, unsubstituted or singly or multiply substituted, and preferably both are $CH_3$;

or $R^3$ and $R^4$ together form a ring and denote $CH_2CH_2NR^{22}CH_2CH_2$ or $(CH_2)_{3-6}$, in particular denote $(CH_2)_{4-5}$ or $CH_2CH_2NR^{22}CH_2CH_2$, where $R^{22}$ is selected from H or $C_{1-6}$ alkyl that is saturated, branched or unbranched and unsubstituted; in particular H or $CH_3$.

In a preferred embodiment of the invention, in the substituted 5-amino-1-penten-3-ol derivatives of formula I $R^5$ is selected from $C_{1-6}$ alkyl, saturated or unsaturated, branched or unbranched, singly or multiply substituted or unsubstituted; from $C_{5-6}$ cycloalkyl, phenyl, thiophenyl, furyl, benzofuranyl, benzothiophenyl, pyrrolyl, pyridinyl, pyrimidinyl, quinolinyl, isoquinolinyl or quinazolinyl, preferably phenyl, furyl, thiophenyl or $C_{5-6}$ cycloalkyl; from phenyl, $C_{5-6}$ cycloalkyl, thiophenyl, furyl, benzofuranyl, benzothiophenyl, pyrrolyl, pyridinyl, pyrimidinyl, quinolinyl, isoquinolinyl, quinazolinyl bound via saturated or unsaturated $C_{1-3}$ alkyl, preferably phenyl, furyl, thiophenyl or $C_{5-6}$ cycloalkyl bound via saturated or unsaturated $C_{1-3}$ alkyl;

wherein all aryl, heteroaryl and cycloalkyl radicals in each case independently of one another may be unsubstituted or singly or multiply substituted, preferably unsubstituted, or are singly or multiply substituted by substituents selected independently of one another from F, Cl, Br, I, OH, O—$C_{1-4}$ alkyl, $C_{1-6}$ alkyl, $CF_3$, $CHF_2$, $CH_2F$, $NH_2$ and/or SH, preferably $R^5$ is selected from $C_{1-3}$ alkyl, saturated or unsaturated, unsubstituted and/or unbranched; or from naphthyl, furyl, cyclohexyl, cyclopentyl, phenyl or thiophenyl, unsubstituted or singly or multiply substituted, preferably by F, Cl, Br, I, $CF_3$, $CHF_2$, $CH_2F$, OH, O—$C_{1-4}$ alkyl, $C_{1-6}$ alkyl, $NH_2$ and/or SH; or from phenyl bound via saturated or unsaturated $C_{1-3}$ alkyl and unsubstituted or singly or multiply substituted preferably by F, Cl, Br, I, $CF_3$, $CHF_2$, $CH_2F$, OH, O—$C_{1-4}$ alkyl, $C_{1-6}$ alkyl, $NH_2$ and/or SH, in particular, $R^5$ is selected from —CH═$CH_2$, cyclohexyl, cyclopentyl, phenyl, phenethyl (phenyl bound via $CH_2$—$CH_2$), benzyl (phenyl bound via $CH_2$) or thiophenyl, unsubstituted or singly or multiply substituted, preferably by F, Cl, Br, I, OH, $OCH_3$, $OC_2H_5$, $OC_3H_7$, SH, $CF_3$, $CHF_2$, $CH_2F$, $CH_3$, $C_2H_5$, $C_3H_7$ and/or $C_4H_9$ or t-butyl.

In a preferred embodiment of the invention, in the substituted 5-amino-1-penten-3-ol derivatives of formula I $R^6$ is selected from phenyl or furyl, in each case unsubstituted or singly or multiply substituted, preferably unsubstituted, or singly or multiply substituted by substituents selected independently of one another from fluorine, chlorine, $CH_3$, $OCH_3$, $CF_3$ or tert.-butyl.

In a preferred embodiment of the invention, in the substituted 5-amino-1-penten-3-ol derivatives of formula I, if $R^5$ is selected from aryl, $C_{3-9}$ cycloalkyl or heteroaryl bound via saturated or unsaturated $C_{1-3}$ alkyl, then the $C_{1-3}$ alkyl, bound via the aryl, heteroaryl or cycloalkyl, is selected from:

—$CH_2$—, —$C_2H_4$—, —$C_3H_6$—, —C≡C—, —CH═CH—, —CH═CH—$CH_2$—,—$CH_2$—CH═CH—, —C≡C—$CH_2$— or —$CH_2$—C≡C—, preferably —$CH_2$—, —$C_2H_4$— or —C≡C—.

In a preferred embodiment of the invention, the substituted 5-amino-1-penten-3-ol derivatives are selected from the following group:

2-benzylidene-1-(3-chlorobenzyl)-6-dimethylaminomethyl-cyclohexanol
2-benzylidene-6-dimethylaminomethyl-1-(2,5-dimethylbenzyl)-cyclohexanol
2-benzylidene-1-(2-chloro-6-fluorobenzyl)-6-dimethylaminomethyl-cyclohexanol
2-benzylidene-1-(4-chlorobenzyl-6-dimethylaminomethyl)-cyclohexanol
2-benzylidene-6-dimethylaminomethyl-1-(3-methylbenzyl)-cyclohexanol
2-benzylidene-6-dimethylaminomethyl-1-(3-trifluoromethylphenyl)-cyclohexanol
2-benzylidene-1-(3-chloro-4-fluorophenyl)-6-dimethylaminomethyl-cyclohexanol
2-benzylidene-6-dimethylaminomethyl-1-(2-methylbenzyl)-cyclohexanol
2-benzylidene-6-dimethylaminomethyl-1-(2-methoxyphenyl)-cyclohexanol
2-benzylidene-6-dimethylaminomethyl-1-(3-fluorobenzyl)-cyclohexanol
2-benzylidene-1-(4-chloro-3-trifluoromethylphenyl)-6-dimethylamino-methyl-cyclohexanol
2-benzylidene-6-dimethylaminomethyl-1-(3-methoxybenzyl)-cyclohexanol
2-benzylidene-6-dimethylaminomethyl-1-(4-fluorobenzyl)-cyclohexanol
2-benzylidene-1-(2-chlorobenzyl)-6-dimethylaminomethyl-cyclohexanol
2-benzylidene-1-(3,5-dichlorophenyl)-6-dimethylaminomethyl-cyclohexanol
2-benzylidene-1-(3-chlorophenyl)-6-dimethylaminomethyl-cyclohexanol
2-benzylidene-6-dimethylaminomethyl-1-(3-fluorophenyl)-cyclohexanol
2-benzylidene-6-dimethylaminomethyl-1-(5-fluoro-2-methoxyphenyl)-cyclohexanol
2-benzylidene-1-cyclohexylmethyl-6-dimethylaminomethyl-cyclohexanol
2-benzylidene-6-dimethylaminomethyl-1-(4-methoxyphenyl)-cyclohexanol
2-benzylidene-6-dimethylaminomethyl-1-p-tolyl-cyclohexanol
2-benzylidene-6-dimethylaminomethyl-1-(3-phenylpropyl)-cyclohexanol
2-benzylidene-6-dimethylaminomethyl-1-(3-methoxyphenyl)-cyclohexanol
2-benzylidene-6-dimethylaminomethyl-1-thiophen-2-yl-cyclohexanol
2-benzylidene-6-dimethylaminomethyl-1-phenylethynyl-cyclohexanol
2-benzylidene-6-dimethylaminomethyl-1-phenethyl-cyclohexanol
2-benzylidene-6-dimethylaminomethyl-1-(4-fluorophenyl)-cyclohexanol
2-benzylidene-6-dimethylaminomethyl-bicyclohexyl-1-ol
2-benzylidene-6-dimethylaminomethyl-1-m-tolyl-cyclohexanol
2-benzylidene-1-cyclopentyl-6-dimethylaminomethyl-cyclohexanol
2-benzylidene-1-(4-tert.-butylphenyl)-6-dimethylaminomethyl-cyclohexanol
2-benzylidene-6-dimethylaminomethyl-1-vinyl-cyclohexanol
2-benzylidene-6-dimethylaminomethyl-1-o-tolyl-cyclohexanol
2-benzylidene-6-dimethylaminomethyl-1-(4-fluoro-3-methylphenyl)-cyclohexanol
1-benzyl-2-benzylidene-6-dimethylaminomethyl-cyclohexanol
2-benzylidene-1-(4-chlorophenyl)-6-dimethylaminomethyl-cyclohexanol
2-benzylidene-6-dimethylaminomethyl-1-phenyl-cyclohexanol
1-(3-chlorobenzyl)-2-(4-chlorobenzylidene)-6-dimethylaminomethyl-cyclohexanol
2-(4-chlorobenzylidene)-6-dimethylaminomethyl-1-(2,5-dimethylbenzyl)-cyclohexanol
2-(4-chlorobenzylidene)-1-(2-chloro-6-fluorobenzyl)-6-dimethylaminomethyl-cyclohexanol
1-(4-chlorobenzyl)-2-(4-chlorobenzylidene)-6-dimethylaminomethyl-cyclohexanol
2-(4-chlorobenzylidene)-6-dimethylaminomethyl-1-(3-trifluoro-methylphenyl)-cyclohexanol
2-(4-chlorobenzylidene)-1-(3-chloro-4-fluorophenyl)-6-dimethyl-aminomethyl-cyclohexanol
2-(4-chlorobenzylidene)-6-dimethylaminomethyl-1-(2-methylbenzyl)-cyclohexanol
2-(4-chlorobenzylidene)-6-dimethylaminomethyl-1-(2-methoxyphenyl)-cyclohexanol
2-(4-chlorobenzylidene)-6-dimethylaminomethyl-1-(3-fluorobenzyl)-cyclohexanol
2-(4-chlorobenzylidene)-1-(4-chloro-3-trifluoromethylphenyl)-6-dimethylaminomethyl-cyclohexanol
2-(4-chlorobenzylidene)-6-dimethylaminomethyl-1-(3-methoxybenzyl)-cyclohexanol
2-(4-chlorobenzylidene)-6-dimethylaminomethyl-1-(4-fluorobenzyl)-cyclohexanol
1-(2-chlorobenzyl)-2-(4-chlorobenzylidene)-6-dimethylaminomethyl-cyclohexanol
2-(4-chlorobenzylidene)-1-(3,5-dichlorophenyl)-6-dimethylaminomethyl-cyclohexanol 2-(4-chlorobenzylidene)-1-(3-chlorophenyl)-6-dimethylaminomethyl-cyclohexanol 2-(4-chlorobenzylidene)-6-dimethylaminomethyl-1-(3-fluorophenyl)-cyclohexanol 2-(4-chlorobenzylidene)-6-dimethylaminomethyl-1-(5-fluoro-2-methoxyphenyl)-cyclohexanol 2-(4-chlorobenzylidene)-1-cyclohexylmethyl-6-dimethylaminomethyl-cyclohexanol 2-(4-chlorobenzylidene)-6-dimethylaminomethyl-1-(4-methoxy-phenyl)-cyclohexanol 2-(4-chlorobenzylidene)-6-dimethylaminomethyl-1-p-tolyl-cyclohexanol 2-(4-chlorobenzylidene)-6-dimethylaminomethyl-1-(3-phenyl-propyl)-cyclohexanol 2-(4-chlorobenzylidene)-6-dimethylaminomethyl-1-(3-methoxyphenyl)-cyclohexanol 2-(4-chlorobenzylidene)-6-dimethylaminomethyl-1-thiophen-2-yl-cyclohexanol 2-(4-chlorobenzylidene)-6-dimethylaminomethyl-1-phenylethynyl-cyclohexanol 2-(4-chlorobenzylidene)-6-dimethylaminomethyl-1-phenethyl-cyclohexanol 2-(4-chlorobenzylidene)-6-dimethylaminomethyl-1-(4-fluorophenyl)-cyclohexanol 2-(4-chlorobenzylidene)-6-dimethylaminomethyl-bicylcohexyl-1-ol 2-(4-chlorobenzylidene)-6-dimethylaminomethyl-1-m-tolyl-cyclohexanol 2-(4-chlorobenzylidene)-1-cyclopentyl-6-dimethylaminomethyl-cyclohexanol 1-(4-tert.-butylphenyl)-2-(4-chlorobenzylidene-6-dimethylamino-methyl-cyclohexanol 2-(4-chlorobenzylidene)-6-dimethylaminomethyl-1-vinyl-cyclohexanol 2-(4-chlorobenzylidene)-6-dimethylaminomethyl-1-o-tolyl-cyclohexanol 2-(4-chlorobenzylidene)-6-dimethylaminomethyl-1-(4-fluoro-3-methylphenyl)-cyclohexanol 1-benzyl-2-(4-chlorobenzylidene)-6-dimethylaminomethyl-cyclohexanol 2-(4-chlorobenzylidene)-1-(4-chlorophenyl)-6-dimethylaminomethyl-cyclohexanol 2-(4-chlorobenzylidene)-6-dimethylaminomethyl-1-phenyl-cyclohexanol 1-(3-chlorobenzyl)-2-dimethylaminomethyl-6-(4-methoxy-benzylidene)-cyclohexanol 2-dimethylaminomethyl-1-(2,5-dimethylbenzyl)-6-(4-methoxy-benzylidene)-cyclohexanol 1-(2-chloro-6-fluorobenzyl)-2-dimethylaminomethyl-6-(4-methoxy-benzylidene)-cyclohexanol 2-dimethylaminomethyl-6-(4-methoxybenzylidene)-1-(3-methyl-benzyl)-cyclohexanol 2-dimethylaminomethyl-6-(4-methoxybenzylidene)-1-(3-trifluoro-methylphenyl)-cyclohexanol 1-(3-chloro-4-fluorophenyl)-2-dimethylaminomethyl-6-(4-methoxy-benzylidene)-cyclohexanol 2-dimethylaminomethyl-6-(4-methoxybenzylidene)-1-(2-methoxy-phenyl)-cyclohexanol 1-(4-chloro-3-trifluoromethylphenyl)-2-dimethylaminomethyl-6-(4-methoxybenzylidene)-cyclohexanol 2-dimethylaminomethyl-1-(4-fluorobenzyl)-6-(4-methoxy-benzylidene)-cyclohexanol 1-(2-chlorobenzyl)-2-dimethylaminomethyl-6-(4-methoxy-benzylidene)-cyclohexanol 1-(3,5-dichlorophenyl)-2-dimethylaminomethyl-6-(4-methoxy-benzylidene)-cyclohexanol 1-(3-chlorophenyl)-2-dimethylaminomethyl-6-(4-methoxy-benzylidene)-cyclohexanol 2-dimethylaminomethyl-1-(5-fluoro-2-methoxyphenyl)-6-(4-methoxybenzylidene)-cyclohexanol 1-cyclohexylmethyl-2-dimethylaminomethyl-6-(4-methoxy-benzylidene)-cyclohexanol 2-dimethylaminomethyl-6-(4-methoxybenzylidene)-1-(4-methoxy-phenyl)-cyclohexanol 2-dimethylaminomethyl-6-(4-methoxybenzylidene)-1-p-tolyl-cyclohexanol 1-(2,3-dichlorophenyl)-2-dimethylaminomethyl-6-(4-methoxy-benzylidene)-cyclohexanol 2-dimethylaminomethyl-6-(4-methoxybenzylidene)-1-(3-phenyl-propyl)-cyclohexanol 2-dimethylaminomethyl-6-(4-methoxybenzylidene)-1-(3-methoxy-phenyl)-cyclohexanol 2-dimethylaminomethyl-6-(4-methoxybenzylidene)-1-thiophen-2-yl-cyclohexanol 2-dimethylaminomethyl-6-(4-methoxybenzylidene)-1-phenylethynyl-cyclohexanol 2-dimethylaminomethyl-6-(4-methoxybenzylidene)-1-phenethyl-cyclohexanol 2-dimethylaminomethyl-1-(4-fluorophenyl)-6-(4-methoxy-benzylidene)-cyclohexanol 6-dimethylaminomethyl-2-(4-methoxybenzylidene)-bicyclohexyl-1-ol 2-dimethylaminomethyl-6-(4-methoxybenzylidene)-1-m-tolyl-cyclohexanol 1-cyclopentyl-2-dimethylaminomethyl-6-(4-methoxybenzylidene)-cyclohexanol 1-(4-tert.-butylphenyl)-2-dimethylaminomethyl-6-(4-methoxy-benzylidene)-cyclohexanol 2-dimethylaminomethyl-6-(4-methoxybenzylidene)-1-vinyl-cyclohexanol 2-dimethylaminomethyl-6-(4-methoxybenzylidene)-1-o-tolyl-cyclohexanol 2-dimethylaminomethyl-1-(4-fluoro-3-methylphenyl)-6-(4-methoxy-benzylidene)-cyclohexanol 1-benzyl-2-dimethylaminomethyl-6-(4-methoxybenzylidene)-cyclohexanol 1-(4-chlorophenyl)-2-dimethylaminomethyl-6-(4-methoxy-benzylidene)-cyclohexanol 2-dimethylaminomethyl-6-(4-methoxybenzylidene)-1-phenyl-cyclohexanol 1-(3-chlorobenzyl)-2-dimethylaminomethyl-6-(3-methoxy-benzylidene)-cyclohexanol 2-dimethylaminomethyl-1-(2,5-dimethylbenzyl)-6-(3-methoxy-benzylidene)-cyclohexanol 2-dimethylaminomethyl-6-(3-methoxybenzylidene)-1-(2-methyl-benzyl)-cyclohexanol 2-dimethylaminomethyl-6-(3-methoxybenzylidene)-1-(2-methoxy-phenyl)-cyclohexanol 1-(4-chloro-3-trifluoromethylphenyl)-2-dimethylaminomethyl-6-(3-methoxybenzylidene)-cyclohexanol 1-(2-chlorobenzyl)-2-dimethylaminomethyl-6-(3-methoxy-benzylidene)-cyclohexanol 6-dimethylaminomethyl-2-(3-methoxybenzylidene)-bicyclohexyl-1-ol 1-cyclopentyl-2-dimethylaminomethyl-6-(3-methoxybenzylidene)-cyclohexanol 2-dimethylaminomethyl-6-(3-methoxybenzylidene)-1-vinyl-cyclohexanol 2-dimethylaminomethyl-1-(4-fluoro-3-methylphenyl)-6-(3-methoxy-benzylidene)-cyclohexanol 1-benzyl-2-dimethylaminomethyl-6-(3-methoxybenzylidene)-cyclohexanol 2-dimethylaminomethyl-6-(3-methoxybenzylidene)-1-phenyl-cyclohexanol 1-benzyl-2-(2-chlorobenzylidene)-6-dimethylaminomethyl-cyclohexanol 5-dimethylaminomethyl-2,4-dimethyl-1,3-diphenyl-pent-1-en-3-ol 3-(4-chlorophenyl)-5-dimethylamino-2,4-dimethyl-1-phenyl-pent-1-en-3-ol 3-benzyl-5-dimethylamino-2,4-dimethyl-1-phenyl-pent-1-en-3-ol 5-dimethylamino-3-(4-fluoro-3-methylphenyl)-2,4-dimethyl-1-phenyl-pent-1-en-3-ol 5-dimethylamino-2,4-dimethyl-1-phenyl-3-o-tolyl-pent-1-en-3-ol 3-(2-dimethylamino-1-methylethyl)-2-methyl-1-phenylpenta-1,4-dien-3-ol 3-(4-tert.-butylphenyl)-5-dimethylamino-2,4-dimethyl-1-phenyl-pent-1-en-3-ol 3-cyclopentyl-5-dimethylamino-2,4-dimethyl-1-phenyl-pent-1-en-3-ol 5-dimethylamino-2,4-dimethyl-1-phenyl-3-m-tolyl-pent-1-en-3-ol 3-cyclohexyl-5-dimethylamino-2,4-dimethyl-1-phenyl-pent-1-en-3-ol 5-dimethylamino-3-(4-fluorophenyl)-2,4-dimethyl-1-phenyl-pent-1-en-3-ol 5-dimethylamino-2,4-dimethyl-3-phenethyl-1-phenyl-pent-1-en-3-ol 3-(2-dimethylamino-1-methylethyl)-2-methyl-1,5-diphenyl-pent-1-en-4-yn-3-ol 5-dimethylamino-2,4-dimethyl-1-phenyl-3-thiophen-2-yl-pent-1-en-3-ol 3-(2,4-dichlorophenyl)-5-dimethylamino-2,4-dimethyl-1-phenyl-pent-1-en-3-ol 5-dimethylamino-3-(3-methoxyphenyl)-2,4-dimethyl-1-phenyl-pent-1-en-3-ol 3-(2-dimethylamino-1-methylethyl)-2-methyl-1,6-diphenylhex-1-en-3-ol 3-(2,3-dichlorophenyl)-5-dimethylamino-2,4-dimethyl-1-phenyl-pent-1-en-3-ol 5-dimethylamino-2,4-dimethyl-1-phenyl-3-p-tolyl-pent-1-en-3-ol 5-dimethylamino-3-(4-methoxyphenyl)-2,4-dimethyl-1-phenyl-pent-1-en-3-ol 3-cyclohexylmethyl-5-dimethylamino-2,4-dimethyl-1-phenyl-pent-1-en-3-ol 5-dimethylamino-3-(5-fluoro-2-methoxyphenyl)-2,4-dimethyl-1-phenyl-pent-1-en-3-ol 5-dimethylamino-3-(3-fluorophenyl)-2,4-dimethyl-1-phenyl-pent-1-en-3-ol 3-(3-chlorophenyl)-5-dimethylamino-2,4-dimethyl-1-phenyl-pent-1-en-3-ol 3-(3,5-chlorophenyl)-5-dimethylamino-2,4-dimethyl-1-phenyl-pent-1-en-3-ol 3-(2-chlorobenzyl)-5-dimethylamino-2,4-dimethyl-1-phenyl-pent-1-en-3-ol 5-dimethylamino-3-(4-fluorobenzyl)-2,4-dimethyl-1-phenyl-pent-1-en-3-ol 3-(4-chloro-3-trifluoromethylphenyl)-5-dimethylamino-2,4-dimethyl-1-phenyl-pent-1-en-3-ol 5-dimethylamino-3-(2-methoxyphenyl)-2,4-dimethyl-1-phenyl-pent-1-en-3-ol 5-dimethylamino-2,4-dimethyl-3-(2-methylbenzyl)-1-phenyl-pent-1-en-3-ol 3-(3-chloro-4-fluorophenyl)-5-dimethylamino-2,4-dimethyl-1-phenyl-pent-1-en-3-ol 5-dimethylamino-2,4-dimethyl-1-phenyl-3-(3-trifluoromethyl-phenyl)-pent-1-en-3-ol 5-dimethylamino-2,4-dimethyl-3-(3-methylbenzyl)-1-phenyl-pent-1-en-3-ol 3-(4-chlorobenzyl)-5-dimethylamino-2,4-dimethyl-1-phenyl-pent-1-en-3-ol 3-(2-chloro-6-fluorobenzyl)-5-dimethylamino-2,4-dimethyl-1-phenyl-pent-1-en-3-ol 5-dimethylamino-3-(2,5-dimethylbenzyl)-2,4-dimethyl-1-phenyl-pent-1-en-3-ol 3-(3-chlorobenzyl)-5-dimethylamino-2,4-dimethyl-1-phenyl-pent-1-en-3-ol 3-(2,4-dichlorobenzyl)-5-dimethylamino-2,4-dimethyl-1-phenyl-pent-1-en-3-ol 5-dimethylamino-1-(4-fluorophenyl)-2,4-dimethyl-3-phenyl-pent-1-en-3-ol 3-benzyl-5-dimethylamino-1-(4-fluorophenyl)-2,4-dimethyl-pent-1-en-3-ol 5-dimethylamino-3-(4-fluoro-3-methylphenyl)-1-(4-fluorophenyl)-2,4-dimethyl-pent-1-en-3-ol 5-dimethylamino-1-(4-fluorophenyl)-2,4-dimethyl-3-o-tolyl-pent-1-en-3-ol 3-(2-dimethylamino-1-methylethyl)-1-(4-fluorophenyl)-2-methyl-pent-1,4-dien-3-ol 3-(4-tert.-butylphenyl)-5-dimethylamino-1-(4-fluorophenyl)-2,4-dimethyl-pent-1-en-3-ol 3-cyclopentyl-5-dimethylamino-1-(4-fluorophenyl)-2,4-dimethyl-pent-1-en-3-ol 5-dimethylamino-1-(4-fluorophenyl)-2,4-dimethyl-3-m-tolyl-pent-1-en-3-ol 3-cyclohexyl-5-dimethylamino-1-(4-fluorophenyl)-2,4-dimethyl-pent-1-en-3-ol 5-dimethylamino-1,3-bis-(4-fluorophenyl)-2,4-dimethyl-pent-1-en-3-ol 5-dimethylamino-1-(4-fluorophenyl)-2,4-dimethyl-3-phenethyl-pent-1-en-3-ol 3-(2-dimethylamino-1-methylethyl)-1-(4-fluorophenyl)-2-methyl-5-phenyl-pent-1-en-4-yn-3-ol 5-dimethylamino-1-(4-fluorophenyl)-2,4-dimethyl-3-thiophen-2-yl-pent-1-en-3-ol 3-(2,4-dichlorophenyl)-5-dimethylamino-1-(4-fluorophenyl)-2,4-dimethyl-pent-1-en-3-ol 5-dimethylamino-1-(4-fluorophenyl)-3-(3-methoxyphenyl)-2,4-dimethyl-pent-1-en-3-ol 3-(2-dimethylamino-1-methylethyl)-1-(4-fluorophenyl)-2-methyl-6-phenyl-hex-1-en-3-ol 3-(2,3-dichlorophenyl)-5-dimethylamino-1-(4-fluorophenyl)-2,4-dimethyl-pent-1-en-3-ol 5-dimethylamino-1-(4-fluorophenyl)-2,4-dimethyl-3-p-tolyl-pent-1-en-3-ol 5-dimethylamino-1-(4-fluorophenyl)-3-(4-methoxyphenyl)-2,4-dimethyl-pent-1-en-3-ol 3-cyclohexylmethyl-5-dimethylamino-1-(4-fluorophenyl)-2,4-dimethyl-pent-1-en-3-ol 5-dimethylamino-3-(5-fluoro-2-methoxyphenyl)-1-(4-fluorophenyl)-2,4-dimethyl-pent-1-en-3-ol 5-dimethylamino-3-(3-fluorophenyl)-1-(4-fluorophenyl)-2,4-dimethyl-pent-1-en-3-ol 3-(3-chlorophenyl)-5-dimethylamino-1-(4-fluorophenyl)-2,4-dimethyl-pent-1-en-3-ol 3-(3,5-dichlorophenyl)-5-dimethylamino-1-(4-fluorophenyl)-2,4-dimethyl-pent-1-en-3-ol 3-(2-chlorobenzyl)-5-dimethylamino-1-(4-fluorophenyl)-2,4-dimethyl-pent-1-en-3-ol 5-dimethylamino-3-(4-fluorobenzyl)-1-(4-fluorophenyl)-2,4-dimethyl-pent-1-en-3-ol 5-dimethylamino-1-(4-fluorophenyl)-3-(3-methoxybenzyl)-2,4-dimethyl-pent-1-en-3-ol 3-(4-chloro-3-trifluoromethylphenyl)-5-dimethylamino-1-(4-fluorophenyl)-2,4-dimethyl-pent-1-en-3-ol 5-dimethylamino-3-(3-fluorobenzyl)-1-(4-fluorophenyl)-2,4-dimethyl-pent-1-en-3-ol 5-dimethylamino-1-(4-fluorophenyl)-3-(2-methoxyphenyl)-2,4-dimethyl-pent-1-en-3-ol 5-dimethylamino-1-(4-fluorophenyl)-2,4-dimethyl-3-(2-methyl-benzyl)-pent-1-en-3-ol 3-(3-chloro-4-fluorophenyl)-5-dimethylamino-1-(4-fluorophenyl)-2,4-dimethyl-pent-1-en-3-ol 5-dimethylamino-1-(4-fluorophenyl)-2,4-dimethyl-3-(3-trifluoro-methylphenyl)-pent-1-en-3-ol 5-dimethylamino-1-(4-fluorophenyl)-2,4-dimethyl-3-(3-methyl-benzyl)-pent-1-en-3-ol 3-(4-chlorobenzyl)-5-dimethylamino-1-(4-fluorophenyl)-2,4-dimethyl-pent-1-en-3-ol 3-(2-chloro-6-fluorobenzyl)-5-dimethylamino-1-(4-fluorophenyl)-2,4-dimethyl-pent-1-en-3-ol 5-dimethylamino-3-(2,5-dimethylbenzyl)-1-(4-fluorophenyl)-2,4-dimethyl-pent-1-en-3-ol 3-(3-chlorobenzyl)-5-dimethylamino-1-(4-fluorophenyl)-2,4-dimethyl-pent-1-en-3-ol 3-(2,4-dichlorobenzyl)-5-dimethylamino-1-(4-fluorophenyl)-2,4-dimethyl-pent-1-en-3-ol 1-(4-chlorophenyl)-5-dimethylamino-2,4-dimethyl-3-phenyl-pent-1-en-3-ol 1,3-bis-(4-chlorophenyl)-5-dimethylamino-2,4-dimethyl-pent-1-en-3-ol 3-benzyl-1-(4-chlorophenyl)-5-dimethylamino-2,4-dimethyl-pent-1-en-3-ol 1-(4-chlorophenyl)-5-dimethylamino-3-(4-fluoro-3-methylphenyl)-2,4-dimethyl-pent-1-en-3-ol 1-(4-chlorophenyl)-5-dimethylamino-2,4-dimethyl-3-o-tolyl-pent-1-en-3-ol 1-(4-chlorophenyl)-3-(2-dimethylamino-1-methylethyl)-2-methyl-penta-1,4-dien-3-ol 3-(4-tert.-butylphenyl)-1-(4-chlorophenyl)-5-dimethylamino-2,4-dimethyl-pent-1-en-3-ol 1-(4-chlorophenyl)-3-cyclopentyl-5-dimethylamino-2,4-dimethyl-pent-1-en-3-ol 1-(4-chlorophenyl)-5-dimethylamino-2,4-dimethyl-3-m-tolyl-pent-1-en-3-ol 1-(4-chlorophenyl)-3-cyclohexyl-5-dimethylamino-2,4-dimethyl-pent-1-en-3-ol 1-(4-chlorophenyl)-5-dimethylamino-3-(4-fluorophenyl)-2,4-dimethyl-pent-1-en-3-ol 1-(4-chlorophenyl)-5-dimethylamino-2,4-dimethyl-3-phenethyl-pent-1-en-3-ol 1-(4-chlorophenyl)-5-dimethylamino-2,4-dimethyl-3-thiophen-2-yl-pent-1-en-3-ol 1-(4-chlorophenyl)-3-(2,4-dichlorophenyl)-5-dimethylamino-2,4-dimethyl-pent-1-en-3-ol 1-(4-chlorophenyl)-5-dimethylamino-3-(3-methoxyphenyl)-2,4-dimethyl-pent-1-en-3-ol 1-(4-chlorophenyl)-3-(2-dimethylamino-1-methylethyl)-2-methyl-6-phenyl-hex-1-en-3-ol 1-(4-chlorophenyl)-3-(2,3-dichlorophenyl)-5-dimethylamino-2,4-dimethyl-pent-1-en-3-ol 1-(4-chlorophenyl)-5-dimethylamino-2,4-dimethyl-3-p-tolyl-pent-1-en-3-ol 1-(4-chlorophenyl)-5-dimethylamino-3-(4-methoxyphenyl)-2,4-dimethyl-pent-1-en-3-ol 1-(4-chlorophenyl)-3-cyclohexylmethyl-5-dimethylamino-2,4-dimethyl-pent-1-en-3-ol 1-(4-chlorophenyl)-5-dimethylamino-3-(5-fluoro-2-methoxyphenyl)-2,4-dimethyl-pent-1-en-3-ol 1-(4-chlorophenyl)-5-dimethylamino-3-(3-fluorophenyl)-2,4-dimethyl-pent-1-en-3-ol 3-(3-chlorophenyl)-1-(4-chlorophenyl)-5-dimethylamino-2,4-dimethyl-pent-1-en-3-ol 1-(4-chlorophenyl)-3-(3,5-dichlorophenyl)-5-dimethylamino-2,4-dimethyl-pent-1-en-3-ol 3-(2-chlorobenzyl)-1-(4-chlorophenyl)-5-dimethylamino-2,4-dimethyl-pent-1-en-3-ol 1-(4-chlorophenyl)-5-dimethylamino-3-(4-fluorobenzyl)-2,4-dimethyl-pent-1-en-3-ol 1-(4-chlorophenyl)-5-dimethylamino-3-(3-methoxybenzyl)-2,4-dimethyl-pent-1-en-3-ol 1-(4-chlorophenyl)-3-(4-chloro-3-trifluoromethylphenyl)-5-dimethylamino-2,4-dimethyl-pent-1-en-3-ol 1-(4-chlorophenyl)-5-dimethylamino-3-[2-(3-fluorophenyl)-ethyl]-2,4-dimethyl-pent-1-en-3-ol 1-(4-chlorophenyl)-5-dimethylamino-3-(2-methoxyphenyl)-2,4-dimethyl-pent-1-en-3-ol 1-(4-chlorophenyl)-5-dimethylamino-2,4-dimethyl-3-(2-methyl-benzyl)-pent-1-en-3-ol 3-(3-chloro-4-fluorophenyl)-1-(4-chlorophenyl)-5-dimethylamino-2,4-dimethyl-pent-1-en-3-ol 1-(4-chlorophenyl)-5-dimethylamino-2,4-dimethyl-3-(3-trifluoro-methylphenyl)-pent-1-en-3-ol 1-(4-chlorophenyl)-5-dimethylamino-2,4-dimethyl-3-(3-methyl-benzyl)-pent-1-en-3-ol 3-(4-chlorobenzyl)-1-(4-chlorophenyl)-5-dimethylamino-2,4-dimethyl-pent-1-en-3-ol 3-(2-chloro-6-fluorobenzyl)-1-(4-chlorophenyl)-5-dimethylamino-2,4-dimethyl-pent-1-en-3-ol 1-(4-chlorophenyl)-5-dimethylamino-3-(2,5-dimethylbenzyl)-2,4-dimethyl-pent-1-en-3-ol 3-(3-chlorobenzyl)-1-(4-chlorophenyl)-5-dimethylamino-2,4-dimethyl-pent-1-en-3-ol 1-(4-chlorophenyl)-3-(2,4-dichlorobenzyl)-5-dimethylamino-2,4-dimethyl-pent-1-en-3-ol 5-dimethylamino-1-(4-methoxyphenyl)-2,4-dimethyl-3-phenyl-pent-1-en-3-ol 3-(4-chlorophenyl)-5-dimethylamino-1-(4-methoxyphenyl)-2,4-dimethyl-pent-1-en-3-ol 3-benzyl-5-dimethylamino-1-(4-methoxyphenyl)-2,4-dimethyl-pent-1-en-3-ol 5-dimethylamino-3-(4-fluoro-3-methylphenyl)-1-(4-methoxyphenyl)-2,4-dimethyl-pent-1-en-3-ol 5-dimethylamino-1-(4-methoxyphenyl)-2,4-dimethyl-3-o-tolyl-pent-1-en-3-ol 3-(2-dimethylamino-1-methylethyl)-1-(4-methoxyphenyl)-2-methyl-penta-1,4-dien-3-ol 3-(4-tert.-butylphenyl)-5-dimethylamino-1-(4-methoxyphenyl)-2,4-dimethyl-pent-1-en-3-ol 3-cyclopentyl-5-dimethylamino-1-(4-methoxyphenyl)-2,4-dimethyl-pent-1-en-3-ol 5-dimethylamino-1-(4-methoxyphenyl)-2,4-dimethyl-3-m-tolyl-pent-1-en-3-ol 3-cyclohexyl-5-dimethylamino-1-(4-methoxyphenyl)-2,4-dimethyl-pent-1-en-3-ol 5-dimethylamino-3-(4-fluorophenyl)-1-(4-methoxyphenyl)-2,4-dimethyl-pent-1-en-3-ol 5-dimethylamino-1-(4-methoxyphenyl)-2,4-dimethyl-3-phenethyl-pent-1-en-3-ol 3-(2-dimethylamino-1-methylethyl)-1-(4-methoxyphenyl)-2-methyl-5-phenyl-pent-1-en-4-yn-3-ol 5-dimethylamino-1-(4-methoxyphenyl)-2,4-dimethyl-3-thiophen-2-yl-pent-1-en-3-ol 3-(2,4-dichlorophenyl)-5-dimethylamino-1-(4-methoxyphenyl)-2,4-dimethyl-pent-1-en-3-ol 5-dimethylamino-3-(3-methoxyphenyl)-1-(4-methoxyphenyl)-2,4-dimethyl-pent-1-en-3-ol 3-(2-dimethylamino-1-methylethyl)-1-(4-methoxyphenyl)-2-methyl-6-phenyl-hex-1-en-3-ol 3-(2,3-dichlorophenyl)-5-dimethylamino-1-(4-methoxyphenyl)-2,4-dimethyl-pent-1-en-3-ol 5-dimethylamino-1-(4-methoxyphenyl)-2,4-dimethyl-3-p-tolyl-pent-1-en-3-ol 5-dimethylamino-1,3-bis-(4-methoxyphenyl)-2,4-dimethyl-pent-1-en-3-ol 3-cyclohexylmethyl-5-dimethylamino-1-(4-methoxyphenyl)-2,4-dimethyl-pent-1-en-3-ol 5-dimethylamino-3-(5-fluoro-2-methoxyphenyl)-1-(4-methoxy-phenyl)-2,4-dimethyl-pent-1-en-3-ol 5-dimethylamino-3-(3-fluorophenyl)-1-(4-methoxyphenyl)-2,4-dimethyl-pent-1-en-3-ol 3-(3-chlorophenyl)-5-dimethylamino-1-(4-methoxyphenyl)-2,4-dimethyl-pent-1-en-3-ol 3-(3,5-dichlorophenyl)-5-dimethylamino-1-(4-methoxyphenyl)-2,4-dimethyl-pent-1-en-3-ol 3-(2-chlorobenzyl)-5-dimethylamino-1-(4-methoxyphenyl)-2,4-dimethyl-pent-1-en-3-ol 5-dimethylamino-3-(4-fluorobenzyl)-1-(4-methoxyphenyl)-2,4-dimethyl-pent-1-en-3-ol 5-dimethylamino-3-(3-fluorobenzyl)-1-(4-methoxyphenyl)-2,4-dimethyl-pent-1-en-3-ol 5-dimethylamino-3-(2-methoxyphenyl)-1-(4-methoxyphenyl)-2,4-dimethyl-pent-1-en-3-ol 5-dimethylamino-1-(4-methoxyphenyl)-2,4-dimethyl-3-(2-methyl-benzyl)-pent-1-en-3-ol 3-(3-chloro-4-fluorophenyl)-5-dimethylamino-1-(4-methoxyphenyl)-2,4-dimethyl-pent-1-en-3-ol 5-dimethylamino-1-(4-methoxyphenyl)-2,4-dimethyl-3-(3-trifluoro-methylphenyl)-pent-1-en-3-ol 3-(4-chlorobenzyl)-5-dimethylamino-1-(4-methoxyphenyl)-2,4-dimethyl-pent-1-en-3-ol 3-(2-chloro-6-fluorobenzyl)-5-dimethylamino-1-(4-methoxyphenyl)-2,4-dimethyl-pent-1-en-3-ol 3-(3-chlorobenzyl)-5-dimethylamino-1-(4-methoxyphenyl)-2,4-dimethyl-pent-1-en-3-ol 2-benzylidene-1-(4-tert.-butylphenyl)-5-dimethylaminomethyl-cyclopentanol 2-benzylidene-1-cyclohexyl-5-dimethylaminomethyl-cyclopentanol 2-benzylidene-5-dimethylaminomethyl-1-phenethyl-cyclopentanol 2-benzylidene-5-dimethylaminomethyl-1-(4-fluorobenzyl)-cyclopentanol 2-benzylidene-5-dimethylaminomethyl-1-(3-fluorobenzyl)-cyclopentanol 2-benzylidene-5-dimethylaminomethyl-1-(2-methoxyphenyl)-cyclopentanol 2-benzylidene-5-dimethylaminomethyl-1-(2-methylbenzyl)-cyclopentanol 2-benzylidene-5-dimethylaminomethyl-1-(3-methylbenzyl)-cyclopentanol 2-benzylidene-1-(4-chlorobenzyl)-5-dimethylaminomethyl-cyclopentanol 2-benzylidene-1-(2-chloro-6-fluorobenzyl)-5-dimethylaminomethyl-cyclopentanol 2-benzylidene-5-dimethylaminomethyl-1-(2,5-dimethylbenzyl)-cyclo-pentanol 2-benzylidene-1-(3-chlorobenzyl)-5-dimethylaminomethyl-cyclopentanol 2-dimethylaminomethyl-5-(3-methoxybenzyl)-bicyclopentyl-1-ol 2-dimethylaminomethyl-5-(3-methoxybenzyl)-1-m-tolyl-cyclopentanol 1-cyclohexyl-2-dimethylaminomethyl-5-(3-methoxybenzyl)-cyclopentanol 2-dimethylaminomethyl-5-(3-methoxybenzyl)-1-phenethyl-cyclopentanol 2-dimethylaminomethyl-5-(3-methoxybenzyl)-1-phenylethynyl-cyclo-pentanol 2-dimethylaminomethyl-5-(3-methoxybenzyl)-1-thiophen-2-yl-cyclo-pentanol 2-dimethylaminomethyl-5-(3-methoxybenzyl)-1-(3-methoxyphenyl)-cyclopentanol 2-dimethylaminomethyl-5-(3-methoxybenzyl)-1-(3-phenylpropyl)-cyclopentanol 2-dimethylaminomethyl-5-(3-methoxybenzyl)-1-(4-methoxyphenyl)-cyclopentanol 2-dimethylaminomethyl-1-(3-fluorobenzyl)-5-(3-methoxy-benzylidene)-cyclopentanol 2-dimethylaminomethyl-5-(3-methoxybenzylidene)-1-(2-methoxy-phenyl)-cyclopentanol 2-dimethylaminomethyl-5-(3-methoxybenzylidene)-1-(2-methyl-benzyl)-cyclopentanol 2-dimethylaminomethyl-5-(3-methoxybenzylidene)-1-(3-methyl-benzyl)-cyclopentanol 2-dimethylaminomethyl-1-(2,5-dimethylbenzyl)-5-(3-methoxy-benzylidene)-cyclopentanol 1-(3-chlorobenzyl)-2-dimethylaminomethyl-5-(3-methoxy-benzylidene)-cyclopentanol 1-benzyl-2-dimethylaminomethyl-5-(3-methoxybenzylidene)-cyclopentanol 2-dimethylaminomethyl-5-(3-methoxybenzylidene)-1-o-tolyl-cyclopentanol 2-dimethylaminomethyl-5-(3-methoxybenzylidene)-1-vinyl-cyclopentanol 1-(4-tert.-butylphenyl)-2-dimethylaminomethyl-5-(3-methoxy-benzylidene)-cyclopentanol 2-dimethylaminomethyl-5-(3-methoxybenzylidene)-bicyclopentyl-1-ol 1-cyclohexyl-2-dimethylaminomethyl-5-(3-methoxybenzylidene)-cyclopentanol 2-dimethylaminomethyl-1-(4-fluorophenyl)-5-(3-methoxy-benzylidene)-cyclopentanol 2-dimethylaminomethyl-5-(3-methoxybenzylidene)-1-phenethyl-cyclopentanol 2-dimethylaminomethyl-5-(3-methoxybenzylidene)-1-phenylethynyl-cyclopentanol 2-dimethylaminomethyl-5-(3-methoxybenzylidene)-1-thiophen-2-yl-cyclopentanol 2-dimethylaminomethyl-5-(3-methoxybenzylidene)-1-(3-methoxy-phenyl)-cyclopentanol 2-dimethylaminomethyl-5-(3-methoxybenzylidene)-1-(3-phenyl-propyl)-cyclopentanol 2-dimethylaminomethyl-5-(3-methoxybenzylidene)-1-p-tolyl-cyclopentanol 2-dimethylaminomethyl-5-(3-methoxybenzylidene)-1-(4-methoxy-phenyl)-cyclopentanol 1-(2-chlorobenzyl)-2-dimethylaminomethyl-5-(4-methoxy-benzylidene)-cyclopentanol 2-dimethylaminomethyl-1-(3-methoxybenzyl)-5-(4-methoxy-benzylidene)-cyclopentanol 2-dimethylaminomethyl-1-(3-fluorobenzyl)-5-(4-methoxy-benzylidene)-cyclopentanol 2-dimethylaminomethyl-5-(4-methoxybenzylidene)-1-(2-methoxy-phenyl)-cyclopentanol 2-dimethylaminomethyl-5-(4-methoxybenzylidene)-1-(3-methyl-benzyl)-cyclopentanol 1-(4-chlorobenzyl)-2-dimethylaminomethyl-5-(4-methoxy-benzylidene)-cyclopentanol 1-(2-chloro-6-fluorobenzyl)-2-dimethylaminomethyl-5-(4-methoxy-benzylidene)-cyclopentanol 1-(3-chlorobenzyl)-2-dimethylaminomethyl-5-(4-methoxy-benzylidene)-cyclopentanol 1-(2,4-dichlorobenzyl)-2-dimethylaminomethyl-5-(4-methoxy-benzylidene)-cyclopentanol 2-benzylidene-7-dimethylaminomethyl-1-phenyl-cycloheptanol 2-benzylidene-1-(4-chlorophenyl)-7-dimethylaminomethyl-cycloheptanol 1-benzyl-2-benzylidene-7-dimethylaminomethyl-cycloheptanol 2-benzylidene-7-dimethylaminomethyl-1-(4-fluoro-3-methylphenyl)-cycloheptanol 2-benzylidene-7-dimethylaminomethyl-1-o-tolyl-cycloheptanol 2-benzylidene-7-dimethylaminomethyl-1-vinyl-cycloheptanol 2-benzylidene-1-(4-tert.-butylphenyl)-7-dimethylaminomethyl-cycloheptanol 2-benzylidene-1-cyclopentyl-7-dimethylaminomethyl-cycloheptanol 2-benzylidene-7-dimethylaminomethyl-1-m-tolyl-cycloheptanol 2-benzylidene-1-cyclohexyl-7-dimethylaminomethyl-cycloheptanol 2-benzylidene-7-dimethylaminomethyl-1-(4-fluorophenyl)-cycloheptanol 2-benzylidene-7-dimethylaminomethyl-1-phenylethynyl-cycloheptanol 2-benzylidene-7-dimethylaminomethyl-1-thiophen-2-yl-cycloheptanol 2-benzylidene-7-dimethylaminomethyl-1-(3-methoxyphenyl)-cycloheptanol 2-benzylidene-1-cyclohexylmethyl-7-dimethylaminomethyl-cycloheptanol 2-benzylidene-7-dimethylaminomethyl-1-(3-fluoro-4-methoxy-phenyl)-cycloheptanol 2-benzylidene-7-dimethylaminomethyl-1-(3-fluorophenyl)-cycloheptanol 2-benzylidene-1-(3-chlorophenyl)-7-dimethylaminomethyl-cycloheptanol 2-benzylidene-1-(3,5-dichlorophenyl)-7-dimethylaminomethyl-cyclo-heptanol 2-benzylidene-7-dimethylaminomethyl-1-(4-fluorobenzyl)-cycloheptanol 2-benzylidene-7-dimethylaminomethyl-1-(4-methoxybenzyl)-cycloheptanol 2-benzylidene-7-dimethylaminomethyl-1-(3-fluorobenzyl)-cycloheptanol 2-benzylidene-7-dimethylaminomethyl-1-(2-methoxyphenyl)-cycloheptanol 2-benzylidene-7-dimethylaminomethyl-1-(2-methylbenzyl)-cycloheptanol 2-benzylidene-1-(3-chloro-4-fluorophenyl)-7-dimethylaminomethyl-cyclo-heptanol 2-benzylidene-7-dimethylaminomethyl-1-(3-trifluoromethylphenyl)-cycloheptanol 2-benzylidene-7-dimethylaminomethyl-1-(3-methylbenzyl)-cycloheptanol 2-benzylidene-1-(4-chlorobenzyl)-7-dimethylaminomethyl-cycloheptanol 2-benzylidene-1-(2-chloro-6-fluorobenzyl)-7-dimethylaminomethyl-cyclo-heptanol 2-benzylidene-7-dimethylaminomethyl-1-(2,5-dimethylbenzyl)-cyclo-heptanol 2-benzylidene-1-(3-chlorobenzyl)-7-dimethylaminomethyl-cycloheptanol 2-dimethylaminomethyl-7-(3-methoxybenzylidene)-1-phenyl-cycloheptanol 1-(4-chlorophenyl)-2-dimethylaminomethyl-7-(3-methoxy-benzylidene)-cycloheptanol 1-benzyl-2-dimethylaminomethyl-7-(3-methoxybenzylidene)-cycloheptanol 2-dimethylaminomethyl-1-(4-fluoro-3-methylphenyl)-7-(3-methoxy-benzylidene)-cycloheptanol 2-dimethylaminomethyl-7-(3-methoxybenzylidene)-1-o-tolyl-cycloheptanol 2-dimethylaminomethyl-7-(3-methoxybenzylidene)-1-vinyl-cycloheptanol 1-(4-tert.-butylphenyl)-2-dimethylaminomethyl-7-(3-methoxy-benzylidene)-cycloheptanol 1-cyclopentyl-2-dimethylaminomethyl-7-(3-methoxybenzylidene)-cycloheptanol 2-dimethylaminomethyl-7-(3-methoxybenzylidene)-1-m-tolyl-cycloheptanol 1-cyclohexyl-2-dimethylaminomethyl-7-(3-methoxybenzylidene)-cycloheptanol 2-dimethylaminomethyl-1-(4-fluorophenyl)-7-(3-methoxy-benzylidene)-cycloheptanol 2-dimethylaminomethyl-7-(3-methoxybenzylidene)-1-phenethyl-cycloheptanol 2-dimethylaminomethyl-7-(3-methoxybenzylidene)-1-phenylethynyl-cycloheptanol 2-dimethylaminomethyl-7-(3-methoxybenzylidene)-1-thiophen-2-yl-cycloheptanol 2-dimethylaminomethyl-7-(3-methoxybenzylidene)-1-(3-methoxy-phenyl)-cycloheptanol 2-dimethylaminomethyl-7-(3-methoxybenzylidene)-1-(3-phenyl-propyl)-cycloheptanol 2-dimethylaminomethyl-7-(3-methoxybenzylidene)-1-p-tolyl-cycloheptanol 2-dimethylaminomethyl-7-(3-methoxybenzylidene)-1-(4-methoxy-phenyl)-cycloheptanol 1-cyclohexylmethyl-2-dimethylaminomethyl-7-(3-methoxy-benzylidene)-cycloheptanol 1-(3-chlorophenyl)-2-dimethylaminomethyl-7-(3-methoxy-benzylidene)-cycloheptanol 1-(3,5-dichlorophenyl)-2-dimethylaminomethyl-7-(3-methoxy-benzylidene)-cycloheptanol 1-(2-chlorobenzyl)-2-dimethylaminomethyl-7-(3-methoxy-benzylidene)-cycloheptanol 1-(4-chloro-3-trifluoromethylphenyl)-2-dimethylaminomethyl-7-(3-methoxybenzylidene)-cycloheptanol 2-dimethylaminomethyl-1-(3-fluorophenyl)-7-(3-methoxy-benzylidene)-cycloheptanol 2-dimethylaminomethyl-7-(3-methoxybenzylidene)-1-(2-methoxy-phenyl)-cycloheptanol 2-dimethylaminomethyl-7-(3-methoxybenzylidene)-1-(2-methyl-benzyl)-cycloheptanol 2-dimethylaminomethyl-7-(3-methoxybenzylidene)-1-(3-trifluoro-methylphenyl)-cycloheptanol 2-dimethylaminomethyl-7-(3-methoxybenzylidene)-1-(3-methyl-benzyl)-cycloheptanol 2-dimethylaminomethyl-1-(2,5-dimethylbenzyl)-7-(3-methoxy-benzylidene)-cycloheptanol 1-(3-chlorobenzyl)-2-dimethylaminomethyl-7-(3-methoxy-benzylidene)-cycloheptanol 1-benzyl-2-dimethylaminomethyl-7-(4-methoxybenzylidene)-cycloheptanol 2-dimethylaminomethyl-1-(4-fluoro-3-methylphenyl)-7-(4-methoxy-benzylidene)-cycloheptanol 2-dimethylaminomethyl-7-(4-methoxybenzylidene)-1-o-tolyl-cycloheptanol 2-dimethylaminomethyl-7-(4-methoxybenzylidene)-1-vinyl-cycloheptanol 1-(4-tert.-butylphenyl)-2-dimethylaminomethyl-7-(4-methoxy-benzylidene)-cycloheptanol 1-cyclopentyl-2-dimethylaminomethyl-7-(4-methoxybenzylidene)-cycloheptanol 2-dimethylaminomethyl-7-(4-methoxybenzylidene)-1-m-tolyl-cycloheptanol 1-cyclohexyl-2-dimethylaminomethyl-7-(4-methoxybenzylidene)-cycloheptanol 2-dimethylaminomethyl-1-(4-fluorophenyl)-7-(4-methoxy-benzylidene)-cycloheptanol 2-dimethylaminomethyl-7-(4-methoxybenzylidene)-1-phenethyl-cycloheptanol 2-dimethylaminomethyl-7-(4-methoxybenzylidene)-1-phenethynyl-cycloheptanol 2-dimethylaminomethyl-7-(4-methoxybenzylidene)-1-thiophen-2-yl-cycloheptanol 2-dimethylaminomethyl-7-(4-methoxybenzylidene)-1-(3-methoxy-phenyl)-cycloheptanol 2-dimethylaminomethyl-7-(4-methoxybenzylidene)-1-(3-phenyl-propyl)-cycloheptanol 2-dimethylaminomethyl-7-(4-methoxybenzylidene)-1-p-tolyl-cycloheptanol 2-dimethylaminomethyl-7-(4-methoxybenzylidene)-1-(4-methoxy-phenyl)-cycloheptanol 1-cyclohexylmethyl-2-dimethylaminomethyl-7-(4-methoxy-benzylidene)-cycloheptanol 1-(3-chlorophenyl)-2-dimethylaminomethyl-7-(4-methoxy-benzylidene)-cycloheptanol 1-(2-chlorobenzyl)-2-dimethylaminomethyl-7-(4-methoxy-benzylidene)-cycloheptanol 2-dimethylaminomethyl-7-(4-methoxybenzylidene)-1-(2-methoxyphenyl)-cycloheptanol 2-dimethylaminomethyl-7-(4-methoxybenzylidene)-1-(2-methylbenzyl)-cycloheptanol 2-dimethylaminomethyl-7-(4-methoxybenzylidene)-1-(3-trifluoro-methylphenyl)-cycloheptanol 2-dimethylaminomethyl-7-(4-methoxybenzylidene)-1-(3-methyl-benzyl)-cycloheptanol 1-(3-chlorobenzyl)-2-dimethylaminomethyl-7-(4-methoxy-benzylidene)-cycloheptanol 1-(3,5-dichlorophenyl)-2-dimethylaminomethyl-7-(4-methoxy-benzylidene)-cycloheptanol 2-benzylidene-7-dimethylaminomethyl-1-(3-hydroxyphenyl)-cycloheptanol 2-dimethylaminomethyl-1-(3-hydroxyphenyl)-7-(3-methoxy-benzylidene)-cycloheptanol 2-benzylidene-7-dimethylaminomethyl-1-(3-methoxyphenyl)-cycloheptanol 3-[1-(2-dimethylaminomethyl-1-methylethyl)-1-hydroxy-2-methyl-3-phenyl-allyl]-phenol 3-(4-chlorobenzyl)-5-dimethylamino-2,4-dimethyl-1-phenyl-pent-1-en-3-ol 5-dimethylamino-3-(3-methoxyphenyl)-2,4-dimethyl-1-phenyl-pent-1-en-3-ol 3-(2-benzylidene-6-dimethylaminomethyl-1-hydroxycyclohexyl)-phenol 1-benzyl-2-benzylidene-7-(4-methylpiperazin-1-ylmethyl)-cycloheptanol 2-benzylidene-1-(2-chlorobenzyl)-7-(4-methylpiperazin-1-ylmethyl)-cycloheptanol 2-benzylidene-1-(3-chlorobenzyl)-7-(4-methylpiperazin-1-ylmethyl)-cycloheptanol 2-benzylidene-1-(4-chlorobenzyl)-7-(4-methylpiperazin-1-ylmethyl)-cycloheptanol 2-benzylidene-1-(2-fluorobenzyl)-7-(4-methylpiperazin-1-ylmethyl)-cycloheptanol 2-benzylidene-1-(3-fluorobenzyl)-7-(4-methylpiperazin-1-ylmethyl)-cycloheptanol 2-benzylidene-1-(4-fluorobenzyl)-7-(4-methylpiperazin-1-ylmethyl)-cycloheptanol 2-benzylidene-1-(2-methylbenzyl)-7-(4-methylpiperazin-1-ylmethyl)-cycloheptanol 2-benzylidene-1-(3-methylbenzyl)-7-(4-methylpiperazin-1-ylmethyl)-cycloheptanol 2-benzylidene-1-(4-methylbenzyl)-7-(4-methylpiperazin-1-ylmethyl)-cycloheptanol 2-benzylidene-1-(2-methoxybenzyl)-7-(4-methylpiperazin-1-ylmethyl)-cycloheptanol 2-benzylidene-1-(3-methoxybenzyl)-7-(4-methylpiperazin-1-ylmethyl)-cycloheptanol 2-benzylidene-1-(4-methoxybenzyl)-7-(4-methylpiperazin-1-ylmethyl)-cycloheptanol 2-benzylidene-1-(2,6-dichlorobenzyl)-7-(4-methylpiperazin-1-ylmethyl)-cycloheptanol 2-benzylidene-1-(2-chloro-6-fluorobenzyl)-7-(4-methylpiperazin-1-ylmethyl)-cycloheptanol 2-benzylidene-1-(2,6-difluorobenzyl)-7-(4-methylpiperazin-1-ylmethyl)-cycloheptanol 1-benzyl-2-(4-chlorobenzylidene)-7-(4-methylpiperazin-1-ylmethyl)-cycloheptanol 1-(2-chlorobenzyl)-2-(4-chlorobenzylidene)-7-(4-methylpiperazin-1-ylmethyl)-cycloheptanol 1-(3-chlorobenzyl)-2-(4-chlorobenzylidene)-7-(4-methylpiperazin-1-ylmethyl)-cycloheptanol 1-(4-chlorobenzyl)-2-(4-chlorobenzylidene)-7-(4-methylpiperazin-1-ylmethyl)-cycloheptanol 2-(4-chlorobenzylidene)-1-(2-fluorobenzyl)-7-(4-methylpiperazin-1-ylmethyl)-cycloheptanol 2-(4-chlorobenzylidene)-1-(3-fluorobenzyl)-7-(4-methylpiperazin-1-ylmethyl)-cycloheptanol 2-(4-chlorobenzylidene)-1-(4-fluorobenzyl)-7-(4-methylpiperazin-1-ylmethyl)-cycloheptanol 2-(4-chlorobenzylidene)-1-(2-methylbenzyl)-7-(4-methylpiperazin-1-ylmethyl)-cycloheptanol 2-(4-chlorobenzylidene)-1-(3-methylbenzyl)-7-(4-methylpiperazin-1-ylmethyl)-cycloheptanol 2-(4-chlorobenzylidene)-1-(4-methylbenzyl)-7-(4-methylpiperazin-1-ylmethyl)-cycloheptanol 2-(4-chlorobenzylidene)-1-(2-methoxybenzyl)-7-(4-methylpiperazin-1-ylmethyl)-cycloheptanol 2-(4-chlorobenzylidene)-1-(3-methoxybenzyl)-7-(4-methylpiperazin-1-ylmethyl)-cycloheptanol 2-(4-chlorobenzylidene)-1-(4-methoxybenzyl)-7-(4-methylpiperazin-1-ylmethyl)-cycloheptanol 2-(4-chlorobenzylidene)-1-(2,6-dichlorobenzyl)-7-(4-methyl-piperazin-1-ylmethyl)-cycloheptanol 2-(4-chlorobenzylidene)-1-(2,6-difluorobenzyl)-7-(4-methyl-piperazin-1-ylmethyl)-cycloheptanol 2-(4-chlorobenzylidene)-1-(2-chloro-6-fluorobenzyl)-7-(4-methyl-piperazin-1-ylmethyl)-cycloheptanol 1-benzyl-2-(4-fluorobenzylidene)-7-(4-methylpiperazin-1-ylmethyl)-cycloheptanol 1-(2-chlorobenzyl)-2-(4-fluorobenzylidene)-7-(4-methylpiperazin-1-ylmethyl)-cycloheptanol 1-(3-chlorobenzyl)-2-(4-fluorobenzylidene)-7-(4-methylpiperazin-1-ylmethyl)-cycloheptanol 1-(4-chlorobenzyl)-2-(4-fluorobenzylidene)-7-(4-methylpiperazin-1-ylmethyl)-cycloheptanol 1-(2-fluorobenzyl)-2-(4-fluorobenzylidene)-7-(4-methylpiperazin-1-ylmethyl)-cycloheptanol 1-(3-fluorobenzyl)-2-(4-fluorobenzylidene)-7-(4-methylpiperazin-1-ylmethyl)-cycloheptanol 1-(4-fluorobenzyl)-2-(4-fluorobenzylidene)-7-(4-methylpiperazin-1-ylmethyl)-cycloheptanol 2-(4-fluorobenzylidene)-1-(2-methylbenzyl)-7-(4-methylpiperazin-1-ylmethyl)-cycloheptanol 2-(4-fluorobenzylidene)-1-(3-methylbenzyl)-7-(4-methylpiperazin-1-ylmethyl)-cycloheptanol 2-(4-fluorobenzylidene)-1-(4-methylbenzyl)-7-(4-methylpiperazin-1-ylmethyl)-cycloheptanol 2-(4-fluorobenzylidene)-1-(2-methoxybenzyl)-7-(4-methylpiperazin-1-ylmethyl)-cycloheptanol 2-(4-fluorobenzylidene)-1-(3-methoxybenzyl)-7-(4-methylpiperazin-1-ylmethyl)-cycloheptanol 2-(4-fluorobenzylidene)-1-(4-methoxybenzyl)-7-(4-methylpiperazin-1-ylmethyl)-cycloheptanol 1-(2,6-dichlorobenzyl)-2-(4-fluorobenzylidene)-7-(4-methyl-piperazin-1-ylmethyl)-cycloheptanol 1-(2,6-difluorobenzyl)-2-(4-fluorobenzylidene)-7-(4-methyl-piperazin-1-ylmethyl)-cycloheptanol 1-(2-chloro-6-fluorobenzyl)-2-(4-fluorobenzylidene)-7-(4-methyl-piperazin-1-ylmethyl)-cycloheptanol 1-benzyl-2-furan-2-ylmethylene-7-(4-methylpiperazin-1-ylmethyl)-cycloheptanol 1-(2-chlorobenzyl)-2-furan-2-ylmethylene-7-(4-methylpiperazin-1-ylmethyl)-cycloheptanol 1-(3-chlorobenzyl)-2-furan-2-ylmethylene-7-(4-methylpiperazin-1-ylmethyl)-cycloheptanol 1-(4-chlorobenzyl)-2-furan-2-ylmethylene-7-(4-methylpiperazin-1-ylmethyl)-cycloheptanol 1-(2-fluorobenzyl)-2-furan-2-ylmethylene-7-(4-methylpiperazin-1-ylmethyl)-cycloheptanol 1-(3-fluorobenzyl)-2-furan-2-ylmethylene-7-(4-methylpiperazin-1-ylmethyl)-cycloheptanol 1-(4-fluorobenzyl)-2-furan-2-ylmethylene-7-(4-methylpiperazin-1-ylmethyl)-cycloheptanol 2-furan-2-ylmethylene-1-(2-methylbenzyl)-7-(4-methylpiperazin-1-ylmethyl)-cycloheptanol 2-furan-2-ylmethylene-1-(3-methylbenzyl)-7-(4-methylpiperazin-1-ylmethyl)-cycloheptanol 2-furan-2-ylmethylene-1-(4-methylbenzyl)-7-(4-methylpiperazin-1-ylmethyl)-cycloheptanol 2-furan-2-ylmethylene-1-(2-methoxybenzyl)-7-(4-methylpiperazin-1-ylmethyl)-cycloheptanol 2-furan-2-ylmethylene-1-(3-methoxybenzyl)-7-(4-methylpiperazin-1-ylmethyl)-cycloheptanol 2-furan-2-ylmethylene-1-(4-methoxybenzyl)-7-(4-methylpiperazin-1-ylmethyl)-cycloheptanol 1-(2,6-dichlorobenzyl)-2-furan-2-ylmethylene-7-(4-methylpiperazin-1-ylmethyl)-cycloheptanol 1-(2,6-difluorobenzyl)-2-furan-2-ylmethylene-7-(4-methylpiperazin-1-ylmethyl)-cycloheptanol 1-(2-chloro-6-fluorobenzyl)-2-furan-2-ylmethylene-7-(4-methyl-piperazin-1-ylmethyl)-cycloheptanol 1-benzyl-3-furan-2-ylmethylene-7-(4-methylpiperazin-1-ylmethyl)-cycloheptanol 1-(2-chlorobenzyl)-3-furan-2-ylmethylene-7-(4-methylpiperazin-1-ylmethyl)-cycloheptanol 1-(3-chlorobenzyl)-3-furan-2-ylmethylene-7-(4-methylpiperazin-1-ylmethyl)-cycloheptanol 1-(4-chlorobenzyl)-3-furan-2-ylmethylene-7-(4-methylpiperazin-1-ylmethyl)-cycloheptanol 1-(2-fluorobenzyl)-3-furan-2-ylmethylene-7-(4-methylpiperazin-1-ylmethyl)-cycloheptanol 1-(3-fluorobenzyl)-3-furan-2-ylmethylene-7-(4-methylpiperazin-1-ylmethyl)-cycloheptanol 1-(4-fluorobenzyl)-3-furan-2-ylmethylene-7-(4-methylpiperazin-1-ylmethyl)-cycloheptanol 3-furan-2-ylmethylene-1-(2-methylbenzyl)-7-(4-methylpiperazin-1-ylmethyl)-cycloheptanol 3-furan-2-ylmethylene-1-(3-methylbenzyl)-7-(4-methylpiperazin-1-ylmethyl)-cycloheptanol 3-furan-2-ylmethylene-1-(4-methylbenzyl)-7-(4-methylpiperazin-1-ylmethyl)-cycloheptanol 3-furan-2-ylmethylene-1-(2-methoxybenzyl)-7-(4-methylpiperazin-1-ylmethyl)-cycloheptanol 3-furan-2-ylmethylene-1-(3-methoxybenzyl)-7-(4-methylpiperazin-1-ylmethyl)-cycloheptanol 3-furan-2-ylmethylene-1-(4-methoxybenzyl)-7-(4-methylpiperazin-1-ylmethyl)-cycloheptanol 1-(2,6-dichlorobenzyl)-3-furan-2-ylmethylene-7-(4-methylpiperazin-1-ylmethyl)-cycloheptanol 1-(2,6-difluorobenzyl)-3-furan-2-ylmethylene-7-(4-methylpiperazin-1-ylmethyl)-cycloheptanol, and 1-(2-chloro-6-fluorobenzyl)-3-furan-2-ylmethylene-7-(4-methyl-piperazin-1-ylmethyl)-cycloheptanol optionally in the form of their racemates, their pure stereoisomers, in particular enantiomers or diastereomers, or in the form of mixtures of the stereoisomers, in particular of the enantiomers or diastereomers, in an arbitrary mixture ratio; in the specified form or in the form of their acids or their bases or in the form of their salts, in particular of physiologically acceptable salts or in the form of their solvates, in particular hydrates, preferably the hydrochloride or dihydrochloride.

In a preferred embodiment of the invention, the substituted 5-amino-1-penten-3-ol derivatives of formula I are the E isomers as shown in formula I':

I'

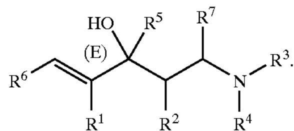

In a further preferred embodiment of the invention, in the substituted 5-amino-1-penten-3-ol derivatives of formula 1, if $R^7$ is hydrogen and $R^1$ and $R^2$ together form a ring, then the OH group and the aminomethylene group $CHR^7$—$NR^3R^4$ according to formula I are in the cis position relative to one another, as shown in formula I":

I"

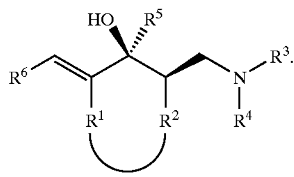

The substances according to the invention are toxicologically harmless, with the result that they are suitable as pharmaceutical active constituents in medicaments. The present invention accordingly also provides medicaments containing at least one substituted 5-amino-1-penten-3-ol derivative according to the invention, as well as optionally suitable additives and/or auxiliary substances and/or optionally further active constituents.

The medicaments according to the invention contain, in addition to at least one substituted 5-amino-1-penten-3-ol derivative according to the invention, optionally suitable additives and/or auxiliary substances, for example also carrier materials, fillers, solvents, diluents, coloring agents and/or binders, and may be administered as liquid medicament preparations in the form of injectable solutions, drops or syrups, as semi-solid medicament preparations in the form of granules, tablets, pellets, patches, capsules, or plasters, or aerosols. The choice of the auxiliary substances, etc., as well as the amounts thereof to be used depend on whether the medicament is to be administered orally, perorally, parenterally, intravenously, intraperitoneally, intradermally, intramuscularly, intranasally, buccally, rectally or topically, for example to the skin, the mucous membranes or the eyes. For oral application suitable preparations are in the form of tablets, sugar-coated pills, capsules, granules, droplets, juices and syrups, while for parenteral, topical and inhalative application suitable forms are solutions, suspensions, readily reconstitutable dry preparations, as well as sprays. Substituted 5-amino-1-penten-3-ol derivatives according to the invention in a depôt form, in dissolved form or in a plaster, optionally with the addition of agents promoting skin penetration, are suitable percutaneous application preparations. Preparation forms that can be administered orally or percutaneously can provide delayed release of the substituted 5-amino-1-penten-3-ol derivatives according to the invention. In principle further active constituents known to the person skilled in the art may be added to the medicaments according to the invention.

The amount of active constituent to be administered to the patient varies depending on the patient's weight, on the type of application, medical indication and severity of the condition. Normally 0.005 to 1000 mg/kg, preferably 0.05 to 5 mg/kg of at least one substituted 5-amino-1-penten-3-ol derivative according to the invention are administered.

In a preferred form of the medicament, the substituted 5-amino-1-penten-3-ol derivative according to the invention is present as pure diastereomer and/or enantiomer, as racemate, or as a non-equimolar or equimolar mixture of the diastereomers and/or enantiomers.

Gabapentin is a known antiepileptic having an anticonvulsive action. Apart from this gabapentin is also used in various other medical conditions, and is prescribed inter alia by physicians to treat migraine and bipolar dysfunctions as well as hot flashes (for example in the post-menopause) (M. Schrope, Modern Drug Discovery, September 2000, p. 11). Other medical conditions in which gabapentin exhibits a potential therapeutic effect have been identified in human studies and in clinical practice (J. S. Bryans, D. J. Wustrow; "3-Substituted GABA Analogs with Central Nervous System Activity: A Review" in Med. Res. Rev. (1999), pp. 149–177). This review article lists the action of gabapentin in detail. For example, gabapentin is effective in the treatment of chronic pain and behavioral disturbances. In particular the following properties of gabapentin are listed: anticonvulsive and antiepileptic actions, the use to treat chronic, neuropathic pain, in particular thermal hyperalgesia, mechanical allodynia, and cold-induced allodynia. In addition gabapentin is effective against neuropathy triggered by nerve damage, in particular neuropathic pain as well as inflammatory and post-operative pain. Gabapentin is also successful in treating antipsychotic conditions, in particular as an anxiolytic. Further investigated conditions include: amyotrophic lateral sclerosis (ALS), reflex sympathetic dystrophy (RSD), spastic palsy, restless leg syndrome, treatment of symptoms and pain caused by multiple sclerosis, acquired nystagmus, treatment of the symptoms of Parkinson's disease, painful diabetic neuropathy and psychiatric disorders, for example bipolar dysfunctions, mood fluctuations and manic behavior. Gabapentin has also been successfully used to treat erythromelagic pain, post-poliomyelitic pain, trigeminal neuralgia and post-herpes neuralgia (Bryans and Wustrow (1999), etc.). The general efficacy of gabapentin in neurodegenerative conditions is also generally known and is also demonstrated by the examples given in the aforementioned review article. Such neurodegenerative conditions include Alzheimer's disease, Huntington's disease, Parkinson's disease and epilepsy. The effectiveness of gabapentin in gastrointestinal damage is also known.

All substances according to the invention displace gabapentin from its binding site, which is up to now still unknown. The substances according to the invention thus bind to the same binding site as gabapentin and become physiologically active through the receptor or the binding site, presumably with the same action profile as gabapentin. This is demonstrated by the analgesic effect, as the compounds according to the invention not only displace gabapentin from its binding site but also, like gabapentin, have a marked analgesic effect.

The present invention accordingly also provides for the use of a substituted 5-amino-1-penten-3-ol derivative according to the invention to produce a medicament to treat pain, in particular neuropathic, chronic or acute pain.

The substances according to the invention may also be used to treat symptoms associated in particular with neuropathic pain, as well as other related medical indications. The present invention furthermore also provides for the use of a substituted 5-amino-1-penten-3-ol derivative according to the invention to produce a medicament to treat migraine, hyperalgesia and allodynia, in particular thermal hyperalgesia, mechanical hyperalgesia and allodynia and cold-induced allodynia, or inflammatory or post-operative pain.

The compounds according to the invention may also be used for other medical conditions. Accordingly, the present invention also provides for the use of a substituted 5-amino-1-penten-3-ol derivative according to the invention to produce a medicament for the treatment of epilepsy, hot flashes, post-menopausal discomfort, amyotropic lateral sclerosis (ALS), reflex sympathetic dystrophy (RSD), spastic palsy, restless leg syndrome, acquired nystagmus; psychiatric or neuropathological disorders, such as bipolar dysfunctions, anxiety, panic attacks, mood fluctuations, manic behavior, depression, manic depressive behavior; painful diabetic neuropathy, symptoms and pain caused by multiple sclerosis or Parkinson's disease, neurodegenerative diseases such as Alzheimer's disease, Huntington's disease, Parkinson's disease and epilepsy; gastrointestinal damage; erythromelalgic or post-poliomyelitic pain, trigeminal or post-herpes neuralgia; or as an anticonvulsive, analgesic or anxiolytic.

In this connection it may be preferable if a substituted 5-amino-1-penten-3-ol derivative according to the invention is present as a pure diastereomer and/or enantiomer, as a racemate or as a non-equimolar or equimolar mixture of the diastereomers and/or enantiomers.

The present invention also provides a process for treating certain symptoms in mammalian or human patients, by administration of a therapeutically active dose of a substituted 5-amino-1-penten-3-ol derivative according to the invention or of a medicament according to the invention. The invention relates in particular to appropriate methods for treating pain, in particular neuropathic, chronic or acute pain; migraine, hyperalgesia and allodynia, in particular thermal hyperalgesia, mechanical hyperalgesia and allodynia and cold-induced allodynia, or inflammatory or post-operative pain; epilepsy, hot flashes, post-menopausal discomfort, amyotrophic lateral sclerosis (ALS), reflex sympathetic dystrophy (RSD), spastic palsy, restless leg syndrome, acquired nystagmus; psychiatric and neuropathic disorders such as bipolar dysfunctions, anxiety, panic attacks, mood fluctuations, manic behavior, depression, manic depressive behavior; painful diabetic neuropathy, symptoms and pain caused by multiple sclerosis or Parkinson's disease, neurodegenerative conditions such as Alzheimer's disease, Huntington's disease, Parkinson's disease and epilepsy; erythromelalgic or post-poliomyelitic disease, trigeminal or post-herpes neuralgia.

The invention furthermore provides a process for the production of a substituted 5-amino-1-penten-3-ol derivative according to the invention as exemplified in the following description and examples.

General Preparation Procedure

Reactions described in the literature (e.g. R. C. Larock, Comprehensive Organic Transformations, $2^{nd}$ Edition, Wiley, N.Y. 1999 and literature cited therein) have been employed for the chemical synthesis work.

5-amino-1-penten-3-ol derivatives of the general formula I

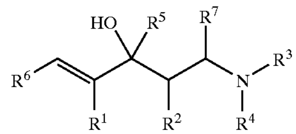

I can be produced by a process in which a β-aminoketone (hereinafter also termed Mannich bases) of formula IA, in which the radicals $R^1$ to $R^4$, $R^6$ and $R^7$ have one of the meanings given above for formula I

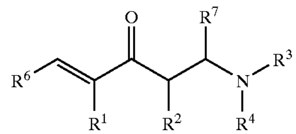

IA is reacted with an organometallic compound of formula III $$R^5—Z \quad \text{III}$$

in which Z denotes MgCl, MgBr, MgI or Li and $R^5$ has one of the meanings given above for formula I, to form a compound of formula I.

The reaction of a β-aminoketone IA with a Grignard compound of formula III in which Z denotes MgCl, MgBr or Mgl, or with an organolithium compound of formula III may be carried out in an aliphatic ether, for example diethyl ether and/or tetrahydrofuran, at temperatures between −70° C. and +60° C. Organolithium compounds of formula III in which Z denotes Cl, Br or I can be obtained by halogen-lithium exchange by reaction with, for example, an n-butyllithium/hexane solution.

β-aminoketones of the general formula IA can be obtained by processes known in the literature (Houben-Weyl—Methoden der Organischen Chemie, E21b, 1995, pp. 1925–1929; M. Tramontini, L. Angiolini, Mannich Bases, Chemistry and Uses, CRS Press, 1994 and literature cited therein).

β-aminoketones of the general formula IA in which $R^7$ is selected from aryl or heteroaryl, in each case unsubstituted or singly or multiply substituted, can be obtained by reacting Mannich bases of formula IV by aldol condensation with aromatic or heteroaromatic aldehydes of the general formula V.

IV

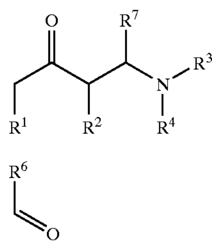

V

Preferably compounds of formula IA can be obtained by reacting enamines of the structure IVa by aldol condensation with aromatic or heteroaromatic aldehydes of the general formula V, $R^a$ and $R^b$ in formula IVa preferably jointly denote —$(CH_2)_2$—O—$(CH_2)_2$—(Hünig, Märkl, Sauer, Integriertes Organisches Pracktikum, Verlag Chemie, Weinheim, 1979).

IVa

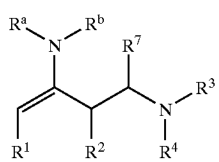

Preferably β-aminoketones of the general formula IV can be obtained by reacting enamines of the general formula VI, this reaction being particularly preferred for compounds in which $R^7 \neq H$,

VI

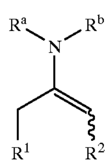

with an iminium salt of the general formula VII

VII

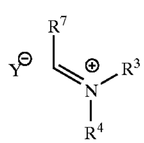

wherein Y preferably denotes $Cl^-$, $AlCl_4^-$, $Br^-$ or $I^-$.

Compounds in which $R^6$ corresponds to H may be prepared similarly to the processes of the conventional Mannich reaction known in the literature via the Eschnmoser salt or BuLi.

The enamines of the general formula VI are obtained by processes known in the literature by reacting ketones of the general formula VIII

VIII

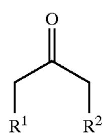

with secondary amines, preferably dimethylamine, pyrrolidine, piperidine or morpholine (Acta Chem. Scand. B 38, 1984, pp. 49–53).

Ketones of formula VIII were either obtained commercially or synthesized according to processes known in the literature.

The iminium salts of the general formula VII are prepared by processes known in the literature by reacting animals of the general formula IX

IX

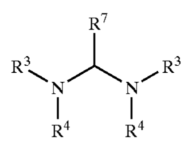

with acid chlorides, for example acetyl chloride or thionyl chloride (Houben-Weyl-Methoden der Organischen Chemie, E21 b, 1995, pp. 1925–1929).

The iminium salts of the general formula VII do not have to be isolated, but can be produced in situ and reacted with enamines of the general formula VI to form Mannich bases of the general formula IV (Angew. Chem. 106, 1994, pp. 2531–2533). On account of the enamine-imine tautomery similar to the keto-enol-tautomery, instead of the enamines of the general formula VI there may also be used imines of the general formula X.

X

Alternatively, ketones of the general formula IV may also be reacted directly with iminium salts of the general formula VII.

Mannich bases of formula IV may also be prepared directly by reacting enamines of the general formula VI with an aromatic or heteroaromatic aldehyde of the general formula XI

XI and a secondary amine of the general formula $HNR^3R^4$ XII also in the form of the corresponding hydrochloride $HNR^3R^4$.HCl, preferably in the presence of triethylamine, chlorotrimethylsilane and sodium iodide (Synlett 1997, pp. 974–976). The Mannich bases of the general formula IV are obtained by the aforedescribed processes and, depending on the reaction conditions, preferably with the relative configuration of the general formula IVa IVa

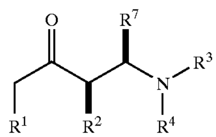

in which the amino group is arranged anti to $R^2$. The compounds of formula IVa can be obtained in diastereomer pure form by crystallization also of their salts, for example the hydrochlorides, or by chromatographic separation.

The preparation of Mannich bases of the general formula IV by 1,4-addition of secondary amines of the general formula XII to enones of the general formula XIII,

XIII

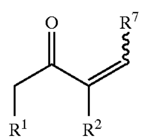

which are obtained by the aldol condensation of ketones of the general formula IV with aromatic or heteroaromatic aldehydes of the general formula XI, proceeds on the other hand less stereoselectively (U.S. Pat. No. 4,017,637). This procedure is therefore suitable for obtaining the other possible stereoisomers.

If chiral amines are used for the preparation of enamines of the general formula VI or imines of the general formula X, then enantiomer-enriched to enantiomer-pure Mannich bases of the general formula IV may be obtained in the subsequent Mannich reaction (Houben-Weyl-Methoden der Organischen Chemie, E21 b, 1995, pp. 1925–1929).

As an alternative to the aforedescribed synthesis sequence, compounds of formula IA in which $R^7$ is hydrogen may also be obtained by reacting ketones of formula VIII with aromatic or heteroaromatic aldehydes of formula V in an aldol condensation to form compounds of formula XIV.

XIV

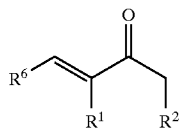

Preferably compounds of formula XIV can be prepared by reacting enamines of the structure VIa by aldol condensation with aromatic or heteroaromatic aldehydes of the general formula V, wherein $R^a$ and $R^b$ in formula VIa preferably jointly denote —$(CH_2)_2$—O—$(CH_2)_2$—(Hünig, Märkl, Sauer, Integriertes Organisches Pracktikum, Verlag Chemie, Weinheim, 1979).

VIa

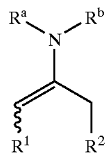

Compounds of formula IX may be reacted directly with iminium salts of formula VII to form the Mannich bases of formula IA.

The diastereomer Mannich bases of formulae IA and IV formed in the aminomethylation reaction can be obtained in diastereomer-pure form either by column chromatography separation or by fractional crystallization of their hydrochlorides from an organic solvent, such as 2-butanone or acetone.

Enantiomer-pure Mannich bases of formulae IA and IV may also be obtained by an aminomethylation using enantiomer-pure ketones of formula IA and VI, or are prepared by racemate resolution via the crystallization of diastereomer salts using chiral acids, preferably tartaric acid, tartaric acid derivatives or mandelic acid (J. Gawroηski, K. Gawroηska, Tartaric and Malic Acids in Synthesis, Wiley, N.Y. 1999, and literature cited therein). These references are explicitly incorporated herein in their entirety by reference.

Salt Formation

The compounds of formula I can be converted into their salts in a manner well-known to those ordinarily skilled in the art with physiologically acceptable acids, for example hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydro1$\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, $\alpha$-liponic acid, acetylglycine, acetylsalicylic acid, hippuric acid and/or aspartic acid. Preferably the salt formation is carried out in a solvent, for example diethyl ether, diisopropyl ether, acetic acid alkyl esters, acetone and/or 2-butanone, or also water. Trimethylchlorosilane in aqueous solution is moreover suitable for the preparation of the hydrochlorides.

The invention is illustrated in more detail hereinafter by means of examples, without however being restricted thereto.

EXAMPLES

The following examples illustrate compounds according to the invention as well as their formation and efficacy investigations carried out with these compounds.

The following remarks generally apply:

The chemicals and solvents used were obtained commercially (Acros, Avocado, Aldrich, Fluka, Lancaster, Maybridge, Merck, Sigma, TCI etc.) or were synthesized).

The analyses were carried out by ESI mass spectrometry and/or HPLC and/or NMR spectroscopy.

Preparation of the Mannich Bases 2-benzylidene-6-dimethylaminomethyl-cyclohexanone

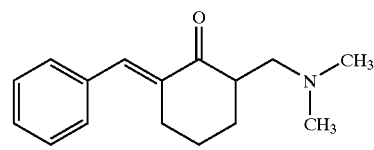

$1^{st}$ Stage: 4-cyclohex-1-enyl-morpholine

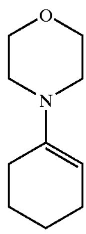

98.2 g (1 mole) of cyclohexanone and 87.7 g (1.2 mole) of morpholine were heated in 400 ml of dry toluene with the addition of 1 g of p-toluenesulfonic acid under reflux in a water separator. After the separation of 18.7 ml of water (after ca. four hours) 4 g of powdered calcium hydride were added and the reaction mixture was heated for a further 30 minutes under reflux. After removal of the solvent by distillation the residue was distilled. The fraction passing over at 70°–73° C. at 0.1 bar was reacted further without purification (yield 108 g, 65% of theory).

$2^{nd}$ Stage: 2-benzylidene-cyclohexanone

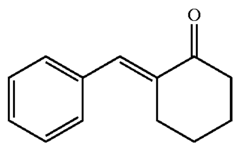

108 g (0.65 mole) of 4-cyclohex-1-enyl-morpholine from stage 1 and 58.0 g (0.55 mole) of benzaldehyde were dissolved in 110 ml of dry toluene and heated for 48 hours under reflux in a water separator. 9 ml of water were separated. After cooling to room temperature, 170 ml of 18 m % hydrochloric acid and 60 ml of toluene were added dropwise while stirring and cooling in an ice bath. The reaction mixture was stirred for a further hour at room temperature. After phase separation the aqueous phase was extracted twice with 100 ml of toluene. The combined organic phases were washed once with 150 ml of water and then with 100 ml of saturated sodium carbonate solution. After drying the reaction mixture over sodium sulfate, the solvent was removed by distillation. The residue was distilled and the fraction that passed over at 120°–125° C. and 0.2 bar was recrystallized from n-hexane. 48.1 g (47% of theory) of pale yellow, waxy crystals having a melting point of 53°–55° C. were obtained.

$3^{rd}$ Stage: 2-benzylidene-6-dimethylaminomethyl-cyclohexanone 43 g (0.23 mole) of 2-benzylidene-cyclohexanone obtained from Stage 2, and 21.6 g (0.23 mole) of dimethylammonium methylene chloride were stirred in 200 ml of dry acetonitrile at room temperature. After adding 0.2 ml of acetyl chloride the reaction mixture was stirred for a further 3 hours at room temperature, a colorless clear solution being formed. 200 ml of dry ether were then added dropwise to the reaction mixture, whereupon the hydrochloride crystallized out. 56.1 g (87% of theory) of colorless crystals were obtained. The base was released from the hydrochloride with dichloromethane/sodium hydroxide and, after drying the solution, the dichloromethane was removed by distillation.

The following Mannich bases of formula II were prepared in a similar way as described in the above example:

2-dimethylaminomethyl-6-(2-methoxybenzylidene)-cyclohexanone 2-dimethylaminomethyl-6-(3-methoxybenzylidene)-cyclohexanone 2-dimethylaminomethyl-6-(4-methoxybenzylidene)-cyclohexanone 2-(2-chlorobenzylidene)-6-dimethylaminomethyl-cyclohexanone 2-(3-chlorobenzylidene)-6-dimethylaminomethyl-cyclohexanone 2-(4-chlorobenzylidene)-6-dimethylaminomethyl-cyclohexanone 2-dimethylaminomethyl-6-(2-fluorobenzylidene)-cyclohexanone 2-dimethylaminomethyl-6-(3-fluorobenzylidene)-cyclohexanone 2-dimethylaminomethyl-6-(4-fluorobenzylidene)-cyclohexanone 2-dimethylaminomethyl-6-(2-methylbenzylidene)-cyclohexanone 2-dimethylaminomethyl-6-(3-methylbenzylidene)-cyclohexanone 2-dimethylaminomethyl-6-(4-methylbenzylidene)-cyclohexanone 2-(3,4-dichlorobenzylidene)-6-dimethylaminomethyl-cyclohexanone 2-biphenyl-4-ylmethylene-6-dimethylaminomethyl-cyclohexanone 2-(4-tert.butylbenzylidene)-6-dimethylaminomethyl-cyclohexanone 2-dimethylaminomethyl-6-naphthalen-1-ylmethylene-cyclohexanone 2-dimethylaminomethyl-6-naphthalen-2-ylmethylene-cyclohexanone 2-benzylidene-6-dimethylaminomethyl-4-phenyl-cyclohexanone 2-(2-chlorobenzylidene)-6-dimethylaminomethyl-4-phenyl-cyclohexanone 2-(3-chlorobenzylidene)-6-dimethylaminomethyl-4-phenyl-cyclohexanone 2-(4-chlorobenzylidene)-6-dimethylaminomethyl-4-phenyl-cyclohexanone 2-dimethylaminomethyl-6-(2-fluorobenzylidene)-4-phenyl-cyclohexanone 2-dimethylaminomethyl-6-(3-fluorobenzylidene)-4-phenyl-cyclohexanone 2-dimethylaminomethyl-6-(4-fluorobenzylidene)-4-phenyl-cyclohexanone 2-dimethylaminomethyl-6-(2-methoxybenzylidene)-4-phenyl-cyclohexanone 2-dimethylaminomethyl-6-(3-methoxybenzylidene)-4-phenyl-cyclohexanone 2-dimethylaminomethyl-6-(4-methoxybenzylidene)-4-phenyl-cyclohexanone 2-dimethylaminomethyl-5-(2-methoxybenzylidene)-cyclopentanone 2-dimethylaminomethyl-5-(3-methoxybenzylidene)-cyclopentanone 2-dimethylaminomethyl-5-(4-methoxybenzylidene)-cyclopentanone 2-(2-chlorobenzylidene)-5-dimethylaminomethyl-cyclopentanone 2-(3-chlorobenzylidene)-5-dimethylaminomethyl-cyclopentanone 2-(4-chlorobenzylidene)-5-dimethylaminomethyl-cyclopentanone 2-dimethylaminomethyl-5-(2-fluorobenzylidene)-cyclopentanone 2-dimethylaminomethyl-5-(3-fluorobenzylidene)-cyclopentanone 2-dimethylaminomethyl-5-(4-fluorobenzylidene)-cyclopentanone 2-dimethylaminomethyl-5-(2-methylbenzylidene)-cyclopentanone 2-dimethylaminomethyl-5-(3-methylbenzylidene)-cyclopentanone 2-dimethylaminomethyl-5-(4-methylbenzylidene)-cyclopentanone 2-(3,4-dichlorobenzylidene)-5-dimethylaminomethyl-cyclopentanone 2-biphenyl-4-ylmethylene-5-dimethylaminomethyl-cyclopentanone 2-(4-tert.butylbenzylidene)-5-dimethylaminomethyl-cyclopentanone 2-dimethylaminomethyl-5-naphthalen-1-ylmethylene-cyclopentanone 2-dimethylaminomethyl-5-naphthalen-2-ylmethylene-cyclopentanone 2-dimethylaminomethyl-7-(2-methoxybenzylidene)-cycloheptanone 2-dimethylaminomethyl-7-(3-methoxybenzylidene)-cycloheptanone 2-dimethylaminomethyl-7-(4-methoxybenzylidene)-cycloheptanone 2-(2-chlorobenzylidene)-7-dimethylaminomethyl-cycloheptanone 2-(3-chlorobenzylidene)-7-dimethylaminomethyl-cycloheptanone 2-(4-chlorobenzylidene)-7-dimethylaminomethyl-cycloheptanone 2-dimethylaminomethyl-7-(2-fluorobenzylidene)-cycloheptanone 2-dimethylaminomethyl-7-(3-fluorobenzylidene)-cycloheptanone 2-dimethylaminomethyl-7-(4-fluorobenzylidene)-cycloheptanone 2-dimethylaminomethyl-7-(2-methylbenzylidene)-cycloheptanone 2-dimethylaminomethyl-7-(3-methylbenzylidene)-cycloheptanone 2-dimethylaminomethyl-7-(4-methylbenzyiidene)-cycloheptanone 2-(3,4-dichlorobenzylidene)-7-dimethylaminomethyl-cycloheptanone 2-biphenyl-4-ylmethylene-7-dimethylaminomethyl-cycloheptanone 2-(4-tert.butylbenzylidene)-7-dimethylaminomethyl-cycloheptanone 2-dimethylaminomethyl-7-naphthalen-1-ylmethylene-cycloheptanone 2-dimethylaminomethyl-7-naphthalen-2-ylmethylene-cycloheptanone 5-dimethylamino-2,4-dimethyl-1-phenyl-pent-1-en-3-one 5-dimethylamino-1-(2-methoxyphenyl)-2,4-dimethyl-pent-1-en-3-one 5-dimethylamino-1-(3-methoxyphenyl)-2,4-dimethyl-pent-1-en-3-one 5-dimethylamino-1-(4-methoxyphenyl)-2,4-dimethyl-pent-1-en-3-one 1-(2-chlorophenyl)-5-dimethylamino-2,4-dimethyl-pent-1-en-3-one 1-(3-chlorophenyl)-5-dimethylamino-2,4-dimethyl-pent-1-en-3-one 1-(4-chlorophenyl)-5-dimethylamino-2,4-dimethyl-pent-1-en-3-one 5-dimethylamino-1-(2-fluorophenyl)-2,4-dimethyl-pent-1-en-3-one 5-dimethylamino-1-(3-fluorophenyl)-2,4-dimethyl-pent-1-en-3-one 5-dimethylamino-1-(4-fluorophenyl)-2,4-dimethyl-pent-1-en-3-one 5-dimethylamino-2,4-dimethyl-1-o-tolyl-pent-1-en-3-one 5-dimethylamino-2,4-dimethyl-1-m-tolyl-pent-1-en-3-one 5-dimethylamino-2,4-dimethyl-1-p-tolyl-pent-1-en-3-one 1-(3,4-dichlorophenyl)-5-dimethylamino-2,4-dimethyl-pent-1-en-3-one 1-biphenyl-4-yl-5-dimethylamino-2,4-dimethyl-pent-1-en-3-one General Operating Instructions 1

The Mannich base (400 μl, 0.5 mol/l) dissolved in THF was added to a baked-out reaction vessel cooled under inert gas to −10° C. 2 equivalents of the prepared Grignard or organolithium reagent were added (0.5 mol/l in THF or diethyl ether, 800 μl) thereto while stirring. The reaction mixture was stirred at room temperature. After three hours the reaction mixture was recooled to −10° C. and hydrolized with ammonium chloride solution.

The reaction mixture was extracted twice with ethyl acetate and concentrated by evaporation in vacuo at 40° C.

An ESI-MS record was taken in each case for purposes of characterization of most of the chlorinated compounds. An NMR spectrum record was also taken in each case for purposes of characterization.

EXAMPLE SUBSTANCES

Example 1

2-benzylidene-1-(3-chlorobenzyl)-6-dimethylaminomethyl-cyclohexanol

Example 2

2-benzylidene-6-dimethylaminomethyl-1-(2,5-dimethylbenzyl)-cyclohexanol

Example 3

2-benzylidene-1-(2-chloro-6-fluorobenzyl)-6-dimethylaminomethyl-cyclohexanol

Example 4

2-benzylidene-1-(4-chlorobenzyl-6-dimethylaminomethyl-cyclohexanol

Example 5

2-benzylidene-6-dimethylaminomethyl-1-(3-methylbenzyl)-cyclohexanol

Example 6

2-benzylidene-6-dimethylaminomethyl-1-(3-trifluoromethylphenyl)-cyclohexanol

Example 7

2-benzylidene-1-(3-chloro-4-fluorophenyl)-6-dimethylaminomethyl-cyclohexanol

Example 8

2-benzylidene-6-dimethylaminomethyl-1-(2-methylbenzyl)-cyclohexanol

Example 9

2-benzylidene-6-dimethylaminomethyl-1-(2-methoxyphenyl)-cyclohexanol

Example 10

2-benzylidene-6-dimethylaminomethyl-1-(3-fluorobenzyl)-cyclohexanol

Example 11

2-benzylidene-1-(4-chloro-3-trifluoromethylphenyl)-6-dimethylaminomethyl-cyclohexanol Example 12

2-benzylidene-6-dimethylaminomethyl-1-(3-methoxybenzyl)-cyclohexanol

Example 13

2-benzylidene-6-dimethylaminomethyl-1-(4-fluorobenzyl)-cyclohexanol

Example 14

2-benzylidene-1-(2-chlorobenzyl)-6-dimethylaminomethyl-cyclohexanol

Example 15

2-benzylidene-1-(3,5-dichlorophenyl)-6-dimethylaminomethyl-cyclohexanol

Example 16

2-benzylidene-1-(3-chlorophenyl)-6-dimethylaminomethyl-cyclohexanol

Example 17

2-benzylidene-6-dimethylaminomethyl-1-(3-fluorophenyl)-cyclohexanol

Example 18

2-benzylidene-6-dimethylaminomethyl-1-(5-fluoro-2-methoxy-phenyl)-cyclohexanol

Example 19

2-benzylidene-1-cyclohexylmethyl-6-dimethylaminomethyl-cyclohexanol

Example 20

2-benzylidene-6-dimethylaminomethyl-1-(4-methoxyphenyl)-cyclohexanol

Example 21

2-benzylidene-6-dimethylaminomethyl-1-p-tolyl-cyclohexanol

Example 22

2-benzylidene-6-dimethylaminomethyl-1-(3-phenylpropyl)-cyclohexanol

Example 23

2-benzylidene-6-dimethylaminomethyl-1-(3-methoxyphenyl)-cyclohexanol

Example 24

2-benzylidene-6-dimethylaminomethyl-1-thiophen-2-yl-cyclohexanol

Example 25

2-benzylidene-6-dimethylaminomethyl-1-phenylethynyl-cyclohexanol

Example 26

2-benzylidene-6-dimethylaminomethyl-1-phenethyl-cyclohexanol

Example 27

2-benzylidene-6-dimethylaminomethyl-1-(4-fluorophenyl)-cyclohexanol

Example 28

2-benzylidene-6-dimethylaminomethyl-bicyclohexyl-1-ol

Example 29

2-benzylidene-6-dimethylaminomethyl-1-m-tolyl-cyclohexanol

Example 30

2-benzylidene-1-cyclopentyl-6-dimethylaminomethyl-cyclohexanol

Example 31

2-benzylidene-1-(4-tert.-butylphenyl)-6-dimethylaminomethyl-cyclohexanol

Example 32

2-benzylidene-6-dimethylaminomethyl-1-vinyl-cyclohexanol

Example 33

2-benzylidene-6-dimethylaminomethyl-1-o-tolyl-cyclohexanol

Example 34

2-benzylidene-6-dimethylaminomethyl-1-(4-fluoro-3-methyl-phenyl)-cyclohexanol

Example 35

1-benzyl-2-benzylidene-6-dimethylaminomethyl-cyclohexanol

Example 36

2-benzylidene-1-(4-chlorophenyl)-6-dimethylaminomethyl-cyclohexanol

Example 37

2-benzylidene-6-dimethylaminomethyl-1-phenyl-cyclohexanol

Example 38

1-(3-chlorobenzyl)-2-(4-chlorobenzylidene)-6-dimethylamino-methyl-cyclohexanol

Example 39

2-(4-chlorobenzylidene)-6-dimethylaminomethyl-1-(2,5-dimethyl-benzyl)-cyclohexanol Example 40

2-(4-chlorobenzylidene)-1-(2-chloro-6-fluorobenzyl)-6-dimethylaminomethyl-cyclohexanol Example 41

1-(4-chlorobenzyl)-2-(4-chlorobenzylidene)-6-dimethylamino-methyl-cyclohexanol

Example 42

2-(4-chlorobenzylidene)-6-dimethylaminomethyl-1-(3-trifluoro-methylphenyl)-cyclohexanol Example 43

2-(4-chlorobenzylidene)-1-(3-chloro-4-fluorophenyl)-6-dimethylaminomethyl-cyclohexanol Example 44

2-(4-chlorobenzylidene)-6-dimethylaminomethyl-1-(2-methyl-benzyl)-cyclohexanol

Example 45

2-(4-chlorobenzylidene)-6-dimethylaminomethyl-1-(2-methoxyphenyl)-cyclohexanol

Example 46

2-(4-chlorobenzylidene)-6-dimethylaminomethyl-1-(3-fluoro-benzyl)-cyclohexanol

Example 47

2-(4-chlorobenzylidene)-1-(4-chloro-3-trifluoromethylphenyl)-6-dimethylaminomethyl-cyclohexanol Example 48

2-(4-chlorobenzylidene)-6-dimethylaminomethyl-1-(3-methoxy-benzyl)-cyclohexanol

Example 49

2-(4-chlorobenzylidene)-6-dimethylaminomethyl-1-(4-fluoro-benzyl)-cyclohexanol

Example 50

1-(2-chlorobenzyl)-2-(4-chlorobenzylidene)-6-dimethylamino-methyl-cyclohexanol

Example 51

2-(4-chlorobenzylidene)-1-(3,5-dichlorophenyl)-6-dimethylaminomethyl-cyclohexanol Example 52

2-(4-chlorobenzylidene)-1-(3-chlorophenyl)-6-dimethylamino-methyl-cyclohexanol

Example 53

2-(4-chlorobenzylidene)-6-dimethylaminomethyl-1-(3-fluoro-phenyl)-cyclohexanol

Example 54

2-(4-chlorobenzylidene)-6-dimethylaminomethyl-1-(5-fluoro-2-methoxyphenyl)-cyclohexanol Example 55

2-(4-chlorobenzylidene)-1-cyclohexylmethyl-6-dimethylamino-methyl-cyclohexanol

Example 56

2-(4-chlorobenzylidene)-6-dimethylaminomethyl-1-(4-methoxy-phenyl)-cyclohexanol

Example 57

2-(4-chlorobenzylidene)-6-dimethylaminomethyl-1-p-tolyl-cyclohexanol

Example 58

2-(4-chlorobenzylidene)-6-dimethylaminomethyl-1-(3-phenyl-propyl)-cyclohexanol

Example 59

2-(4-chlorobenzylidene)-6-dimethylaminomethyl-1-(3-methoxy-phenyl)-cyclohexanol

Example 60

2-(4-chlorobenzylidene)-6-dimethylaminomethyl-1-thiophen-2-yl-cyclohexanol

Example 61

2-(4-chlorobenzylidene)-6-dimethylaminomethyl-1-phenylethynyl-cyclohexanol

Example 62

2-(4-chlorobenzylidene)-6-dimethylaminomethyl-1-phenylethyl-cyclohexanol

Example 63

2-(4-chlorobenzylidene)-6-dimethylaminomethyl-1-(4-fluoro-phenyl)-cyclohexanol

Example 64

2-(4-chlorobenzylidene)-6-dimethylaminomethyl-bicylcohexyl-1-ol

Example 65

2-(4-chlorobenzylidene)-6-dimethylaminomethyl-1-m-tolyl-cyclohexanol

Example 66

2-(4-chlorobenzylidene)-1-cyclopentyl-6-dimethylaminomethyl-cyclohexanol

Example 67

1-(4-tert.-butylphenyl)-2-(4-chlorobenzylidene-6-dimethylamino-methyl-cyclohexanol Example 68

2-(4-chlorobenzylidene)-6-dimethylaminomethyl-1-vinyl-cyclohexanol

Example 69

2-(4-chlorobenzylidene)-6-dimethylaminomethyl-1-o-tolyl-cyclohexanol

Example 70

2-(4-chlorobenzylidene)-6-dimethylaminomethyl-1-(4-fluoro-3-methylphenyl)-cyclohexanol Example 71

1-benzyl-2-(4-chlorobenzylidene)-6-dimethylaminomethyl-cyclohexanol

Example 72

2-(4-chlorobenzylidene)-1-(4-chlorophenyl)-6-dimethylamino-methyl-cyclohexanol

Example 73

2-(4-chlorobenzylidene)-6-dimethylaminomethyl-1-phenyl-cyclohexanol

Example 74

1-(3-chlorobenzyl)-2-dimethylaminomethyl-6-(4-methoxy-benzylidene)-cyclohexanol

Example 75

2-dimethylaminomethyl-1-(2,5-dimethylbenzyl)-6-(4-methyl-benzylidene)-cyclohexanol Example 76

1-(2-chloro-6-fluorobenzyl)-2-dimethylaminomethyl-6-(4-methyl-benzylidene)-cyclohexanol Example 77

2-dimethylaminomethyl-6-(4-methoxybenzylidene)-1-(3-methyl-benzyl)-cyclohexanol

Example 78

2-dimethylaminomethyl-6-(4-methoxybenzylidene)-1-(3-trifluoro-methylphenyl)-cyclohexanol Example 79

1-(3-chloro-4-fluorophenyl)-2-dimethylaminomethyl-6-(4-methoxybenzylidene)-cyclohexanol Example 80

2-dimethylaminomethyl-6-(4-methoxybenzylidene)-1-(2-methoxy-phenyl)-cyclohexanol Example 81

1-(4-chloro-3-trifluoromethylphenyl)-2-dimethylaminomethyl-6-(4-methoxybenzylidene)-cyclohexanol Example 82

2-dimethylaminomethyl-1-(4-fluorobenzyl)-6-(4-methoxybenzylidene)-cyclohexanol

Example 83

1-(2-chlorobenzyl)-2-dimethylaminomethyl-6-(4-methoxybenzylidene)-cyclohexanol

Example 84

1-(3,5-dichlorophenyl)-2-dimethylaminomethyl-6-(4-methoxy-benzylidene)-cyclohexanol Example 85

1-(3-chlorophenyl)-2-dimethylaminomethyl-6-(4-methoxy-benzylidene)-cyclohexanol

Example 86

2-dimethylaminomethyl-1-(5-fluoro-2-methoxyphenyl)-6-(4-methoxybenzylidene)-cyclohexanol Example 87

1-cyclohexylmethyl-2-dimethylaminomethyl-6-(4-methoxy-benzylidene)-cyclohexanol

Example 88

2-dimethylaminomethyl-6-(4-methoxybenzylidene)-1-(4-methoxyphenyl)-cyclohexanol

Example 89

2-dimethylaminomethyl-6-(4-methoxybenzylidene)-1-p-tolyl-cyclohexanol

Example 90

1-(2,3-dichlorophenyl)-2-dimethylaminomethy-6-(4-methoxy-benzylidene)-cyclohexanol Example 91

2-dimethylaminomethyl-6-(4-methoxybenzylidene)-1-(3-phenyl-propyl)-cyclohexanol

Example 92

2-dimethylaminomethyl-6-(4-methoxybenzylidene)-1-(3-methoxy-phenyl)-cyclohexanol Example 93

2-dimethylaminomethyl-6-(4-methoxybenzylidene)-1-thiophen-2-yl-cyclohexanol

Example 94

2-dimethylaminomethyl-6-(4-methoxybenzylidene)-1-phenyl-ethynyl-cyclohexanol

Example 95

2-dimethylaminomethyl-6-(4-methoxybenzylidene)-1-phenethyl-cyclohexanol

Example 96

2-dimethylaminomethyl-1-(4-fluorophenyl)-6-(4-methoxy-benzylidene)-cyclohexanol

Example 97

6-dimethylaminomethyl-2-(4-methoxybenzylidene)-bicyclohexyl-1-ol

Example 98

2-dimethylaminomethyl-6-(4-methoxybenzylidene)-1-m-tolyl-cyclohexanol

Example 99

1-cyclopentyl-2-dimethylaminomethyl-6-(4-methoxybenzylidene)-cyclohexanol

Example 100

1-(4-tert.-butylphenyl)-2-dimethylaminomethyl-6-(4-methyl-benzylidene)-cyclohexanol Example 101

2-dimethylaminomethyl-6-(4-methoxybenzylidene)-1-vinyl-cyclohexanol

Example 102

2-dimethylaminomethyl-6-(4-methoxybenzylidene)-1-o-tolyl-cyclohexanol

Example 103

2-dimethylaminomethyl-1-(4-fluoro-3-methylphenyl)-6-(4-methoxybenzylidene)-cyclohexanol Example 104

1-benzyl-2-dimethylaminomethyl-6-(4-methoxybenzylidene)-cyclohexanol

Example 105

1-(4-chlorophenyl)-2-dimethylaminomethyl-6-(4-methoxy-benzylidene)-cyclohexanol

Example 106

2-dimethylaminomethyl-6-(4-methoxybenzylidene)-1-phenyl-cyclohexanol

Example 107

1-(3-chlorobenzyl)-2-dimethylaminomethyl-6-(3-methoxy-benzylidene)-cyclohexanol

Example 108

2-dimethylaminomethyl-1-(2,5-dimethylbenzyl)-6-(3-methoxy-benzylidene)-cyclohexanol Example 109

2-dimethylaminomethyl-6-(3-methoxybenzylidene)-1-(2-methylbenzyl)-cyclohexanol

Example 110

2-dimethylaminomethyl-6-(3-methoxybenzylidene)-1-(2-methoxyphenyl)-cyclohexanol

Example 111

1-(4-chloro-3-trifluoromethylphenyl)-2-dimethylaminomethyl-6-(3-methoxybenzylidene)-cyclohexanol Example 112

1-(2-chlorobenzyl)-2-dimethylaminomethyl-6-(3-methoxy-benzylidene)-cyclohexanol

Example 113

6-dimethylaminomethyl-2-(3-methoxybenzylidene)-bicyclohexyl-1-ol

Example 114

1-cyclopentyl-2-dimethylaminomethyl-6-(3-methoxybenzylidene)-cyclohexanol

Example 115

2-dimethylaminomethyl-6-(3-methoxybenzylidene)-1-vinyl-cyclohexanol

Example 116

2-dimethylaminomethyl-1-(4-fluoro-3-methylphenyl)-6-(3-methoxybenzylidene)-cyclohexanol Example 117

1-benzyl-2-dimethylaminomethyl-6-(3-methoxybenzylidene)-cyclohexanol

Example 118

2-dimethylaminomethyl-6-(3-methoxybenzylidene)-1-phenyl-cyclohexanol

Example 119

1-benzyl-2-(2-chlorobenzylidene)-6-dimethylaminomethyl-cyclohexanol

Example 120

5-dimethylamino-2,4-dimethyl-1,3-diphenyl-pent-1-en-3-ol

Example 121

3-(4-chlorophenyl)-5-dimethylamino-2,4-dimethyl-1-phenyl-pent-1-en-3-ol

Example 122

3-benzyl-5-dimethylamino-2,4-dimethyl-1-phenyl-pent-1-en-3-ol

Example 123

5-dimethylamino-3-(4-fluoro-3-methylphenyl)-2,4-dimethyl-1-phenyl-pent-1-en-3-ol Example 124

5-dimethylamino-2,4-dimethyl-1-phenyl-3-tolyl-pent-1-en-3-ol

Example 125

3-(2-dimethylamino-1-methylethyl)-2-methyl-1-phenylpenta-1,4-dien-3-ol

Example 126

3-(4-tert.-butylphenyl)-5-dimethylamino-2,4-dimethyl-1-phenyl-pent-1-en-3-ol

Example 127

3-cyclopentyl-5-dimethylamino-2,4-dimethyl-1-phenyl-pent-1-en-3-ol

Example 128

5-dimethylamino-2,4-dimethyl-1-phenyl-3-m-tolyl-pent-1-en-3-ol

Example 129

3-cyclohexyl-5-dimethylamino-2,4-dimethyl-1-phenyl-pent-1-en-3-ol

Example 130

5-dimethylamino-3-(4-fluorophenyl)-2,4-dimethyl-1-phenyl-pent-1-en-3-ol

Example 131

5-dimethylamino-2,4-dimethyl-3-phenethyl-1-phenyl-pent-1-en-3-ol

Example 132

3-(2-dimethylamino-1-methylethyl)-2-methyl-1,5-diphenyl-pent-1-an-4-yn-3-ol

Example 133

5-dimethylamino-2,4-dimethyl-1-phenyl-3-thiophen-2-yl-pent-1-en-3-ol

Example 134

3-(2,4-dichlorophenyl)-5-dimethylamino-2,4-dimethyl-1-phenyl-pent-1-en-3-ol

Example 135

5-dimethylamino-3-(3-methoxyphenyl)-2,4-dimethyl-1-phenyl-pent-1-en-3-ol

Example 136

3-(2-dimethylamino-1-methylethyl)-2-methyl-1,6-diphenylhex-1-en-3-ol

Example 137

3-(2,3-dichlorophenyl)-5-dimethylamino-2,4-dimethyl-1-phenyl-pent-1-en-3-ol

Example 138

5-dimethylamino-2,4-dimethyl-1-phenyl-3-p-tolyl-pent-1-en-3-ol

Example 139

5-dimethylamino-3-(4-methoxyphenyl)-2,4-dimethyl-1-phenyl-pent-1-en-3-ol

Example 140

3-cyclohexylmethyl-5-dimethylamino-2,4-dimethyl-1-phenyl-pent-1-en-3-ol

Example 141

5-dimethylamino-3-(5-fluoro-2-methoxyphenyl)-2,4-dimethyl-1-phenyl-pent-1-en-3-ol Example 142

5-dimethylamino-3-(3-fluorophenyl)-2,4-dimethyl-1-phenyl-pent-1-en-3-ol

Example 143

3-(3-chlorophenyl)-5-dimethylamino-2,4-dimethyl-1-phenyl-pent-1-en-3-ol

Example 144

3-(3,5-chlorophenyl)-5-dimethylamino-2,4-dimethyl-1-phenyl-pent-1-en-3-ol

Example 145

3-(2-chlorobenzyl)-5-dimethylamino-2,4-dimethyl-1-phenyl-pent-1-en-3-ol

Example 146

5-dimethylamino-3-(4-fluorobenzyl)-2,4-dimethyl-1-phenyl-pent-1-en-3-ol

Example 147

3-(4-chloro-3-trifluoromethylphenyl)-5-dimethylamino-2,4-dimethyl-1-phenyl-pent-1-en-3-ol Example 148

5-dimethylamino-3-(2-methoxyphenyl)-2,4-dimethyl-1-phenyl-pent-1-en-3-ol

Example 149

5-dimethylamino-2,4-dimethyl-3-(2-methylbenzyl)-1-phenyl-pent-1-en-3-ol

Example 150

3-(3-chloro-4-fluorophenyl)-5-dimethylamino-2,4-dimethyl-1-phenyl-pent-1-en-3-ol Example 151

5-dimethylamino-2,4-dimethyl-1-phenyl-3-(3-trifluoromethyl-phenyl)-pent-1-en-3-ol Example 152

5-dimethylamino-2,4-dimethyl-3-(3-methylbenzyl)-1-phenyl-pent-1-en-3-ol

Example 153

3-(4-chlorobenzyl)-5-dimethylamino-2,4-dimethyl-1-phenyl-pent-1-en-3-ol

Example 154

3-(2-chloro-6-fluorobenzyl)-5-dimethylamino-2,4-dimethyl-1-phenyl-pent-1-en-3-ol Example 155

5-dimethylamino-3-(2,5-dimethylbenzyl)-2,4-dimethyl-1-phenyl-pent-1-en-3-ol

Example 156

3-(3-chlorobenzyl)-5-dimethylamino-2,4-dimethyl-1-phenyl-pent-1-en-3-ol

Example 157

3-(2,4-dichlorobenzyl)-5-dimethylamino-2,4-dimethyl-1-phenyl-pent-1-en-3-ol

Example 158

5-dimethylamino-1-(4-fluorophenyl)-2,4-dimethyl-3-phenyl-pent-1-en-3-ol

Example 159

3-benzyl-5-dimethylamino-1-(4-fluorophenyl)-2,4-dimethyl-pent-1-en-3-ol

Example 160

5-dimethylamino-3-(4-fluoro-3-methylphenyl)-1-(4-fluorophenyl)-2,4-dimethyl-pent-1-en-3-ol Example 161

5-dimethylamino-1-(4-fluorophenyl)-2,4-dimethyl-3-o-tolyl-pent-1-en-3-ol

Example 162

3-(2-dimethylamino-1-methylethyl)-1-(4-fluorophenyl)-2-methyl-penta-1,4-dien-3-ol Example 163

3-(4-tert.-butylphenyl)-5-dimethylamino-1-(4-fluorophenyl)-2,4-dimethyl-pent-1-en-3-ol Example 164

3-cyclopentyl-5-dimethylamino-1-(4-fluorophenyl)-2,4-dimethyl-pent-1-en-3-ol

Example 165

5-dimethylamino-1-(4-fluorophenyl)-2,4-dimethyl-3-m-tolyl-pent-1-en-3-ol

Example 166

3-cyclohexyl-5-dimethylamino-1-(4-fluorophenyl)-2,4-dimethyl-pent-1-en-3-ol

Example 167

5-dimethylamino-1,3-bis-(4-fluorophenyl)-2,4-dimethyl-pent-1-en-3-ol

Example 168

5-dimethylamino-1-(4-fluorophenyl)-2,4-dimethyl-3-phenethyl-pent-1-en-3-ol

Example 169

3-(2-dimethylamino-1-methylethyl)-1-(4-fluorophenyl)-2-methyl-5-phenyl-pent-1-en-4-yn-3-ol Example 170

5-dimethylamino-1-(4-fluorophenyl)-2,4-dimethyl-3-thiophen-2-yl-pent-1-en-3-ol

Example 171

3-(2,4-dichlorophenyl)-5-dimethylamino-1-(4-fluorophenyl)-2,4-dimethyl-pent-1-en-3-ol Example 172

5-dimethylamino-1-(4-fluorophenyl)-3-(3-methoxyphenyl)-2,4-dimethyl-pent-1-en-3-ol Example 173

3-(2-dimethylamino-1-methylethyl)-1-(4-fluorophenyl)-2-methyl-6-phenyl-hex-1-en-3-ol Example 174

3-(2,3-dichlorophenyl)-5-dimethylamino-1-(4-fluorophenyl)-2,4-dimethyl-pent-1-en-3-ol Example 175

5-dimethylamino-1-(4-fluorophenyl)-2,4-dimethyl-3-p-tolyl-pent-1-en-3-ol

Example 176

5-dimethylamino-1-(4-fluorophenyl)-3-(4-methoxyphenyl)-2,4-dimethyl-pent-1-en-3-ol Example 177

3-cyclohexylmethyl-5-dimethylamino-1-(4-fluorophenyl)-2,4-dimethyl-pent-1-en-3-ol Example 178

5-dimethylamino-3-(5-fluoro-2-methoxyphenyl)-1-(4-fluorophenyl)-2,4-dimethyl-pent-1-en-3-ol Example 179

5-dimethylamino-3-(3-fluorophenyl)-1-(4-fluorophenyl)-2,4-dimethyl-pent-1-en-3-ol Example 180

3-(3-chlorophenyl)-5-dimethylamino-1-(4-fluorophenyl)-2,4-dimethyl-pent-1-en-3-ol Example 181

3-(3,5-dichlorophenyl)-5-dimethylamino-1-(4-fluorophenyl)-2,4-dimethyl-pent-1-en-3-ol Example 182

3-(2-chlorobenzyl)-5-dimethylamino-1-(4-fluorophenyl)-2,4-dimethyl-pent-1-en-3-ol Example 183

5-dimethylamino-3-(4-fluorobenzyl)-1-(4-fluorophenyl)-2,4-dimethyl-pent-1-en-3-ol Example 184

5-dimethylamino-1-(4-fluorophenyl)-3-(3-methoxybenzyl)-2,4-dimethyl-pent-1-en-3-ol Example 185

3-(4-chloro-3-trifluoromethylphenyl)-5-dimethylamino-1-(4-fluoro-phenyl)-2,4-dimethyl-pent-1-en-3-ol Example 186

5-dimethylamino-3-(3-fluorobenzyl)-1-(4-fluorophenyl)-2,4-dimethyl-pent-1-en-3-ol Example 187

5-dimethylamino-1-(4-fluorophenyl)-3-(2-methoxyphenyl)-2,4-dimethyl-pent-1-en-3-ol Example 188

5-dimethylamino-1-(4-fluorophenyl)-2,4-dimethyl-3-(2-methyl-benzyl)-pent-1-en-3-ol Example 189

3-(3-chloro-4-fluorophenyl)-5-dimethylamino-1-(4-fluorophenyl)-2,4-dimethyl-pent-1-en-3-ol Example 190

5-dimethylamino-1-(4-fluorophenyl)-2,4-dimethyl-3-(3-trifluoro-methylphenyl)-pent-1-en-3-ol Example 191

5-dimethylamino-1-(4-fluorophenyl)-2,4-dimethyl-3-(3-methyl-benzyl)-pent-1-en-3-ol Example 192

3-(4-chlorobenzyl)-5-dimethylamino-1-(4-fluorophenyl)-2,4-dimethyl-pent-1-en-3-ol Example 193

3-(2-chloro-6-fluorobenzyl)-5-dimethylamino-1-(4-fluorophenyl)-2,4-dimethyl-pent-1-en-3-ol Example 194

5-dimethylamino-3-(2,5-dimethylbenzyl)-1-(4-fluorophenyl)-2,4-dimethyl-pent-1-en-3-ol Example 195

3-(3-chlorobenzyl)-5-dimethylamino-1-(4-fluorophenyl)-2,4-dimethyl-pent-1-en-3-ol Example 196

3-(2,4-dichlorobenzyl)-5-dimethylamino-1-(4-fluorophenyl)-2,4-dimethyl-pent-1-en-3-ol Example 197

1-(4-chlorophenyl)-5-dimethylamino-2,4-dimethyl-3-phenyl-pent-1-en-3-ol

Example 198

1,3-bis-(4-chlorophenyl)-5-dimethylamino-2,4-dimethyl-pent-1-en-3-ol

Example 199

3-benzyl-1-(4-chlorophenyl)-5-dimethylamino-2,4-dimethyl-pent-1-en-3-ol

Example 200

1-(4-chlorophenyl)-5-dimethylamino-3-(4-fluoro-3-methylphenyl)-2,4-dimethyl-pent-1-en-3-ol Example 201

1-(4-chlorophenyl)-5-dimethylamino-2,4-dimethyl-3-o-tolyl-pent-1-en-3-ol

Example 202

1-(4-chlorophenyl)-3-(2-dimethylamino-1-methylethyl)-2-methyl-penta-1,4-dien-3-ol Example 203

3-(4-tert.-butylphenyl)-1-(4-chlorophenyl)-5-dimethylamino-2,4-dimethyl-pent-1-en-3-ol Example 204

1-(4-chlorophenyl)-3-cyclopentyl-5-dimethylamino-2,4-dimethyl-pent-1-en-3-ol

Example 205

1-(4-chlorophenyl)-5-dimethylamino-2,4-dimethyl-3-m-tolyl-pent-1-en-3-ol

Example 206

1-(4-chlorophenyl)-3-cyclohexyl-5-dimethylamino-2,4-dimethyl-pent-1-en-3-ol

Example 207

1-(4-chlorophenyl)-5-dimethylamino-3-(4-fluorophenyl)-2,4-dimethyl-pent-1-en-3-ol Example 208

1-(4-chlorophenyl)-5-dimethylamino-2,4-dimethyl-3-phenethyl-pent-1-en-3-ol

Example 209

1-(4-chlorophenyl)-5-dimethylamino-2,4-dimethyl-3-thiophen-2-yl-pent-1-en-3-ol

Example 210

1-(4-chlorophenyl)-3-(2,4-dichlorophenyl)-5-dimethylamino-2,4-dimethyl-pent-1-en-3-ol Example 211

1-(4-chlorophenyl)-5-dimethylamino-3-(3-methoxyphenyl)-2,4-dimethyl-pent-1-en-3-ol Example 212

1-(4-chlorophenyl)-3-(2-dimethylamino-1-methylethyl)-2-methyl-6-phenyl-hex-1-en-3-ol Example 213

1-(4-chlorophenyl)-3-(2,3-dichlorophenyl)-5-dimethylamino-2,4-dimethyl-pent-1-en-3-ol Example 214

1-(4-chlorophenyl)-5-dimethylamino-2,4-dimethyl-3-p-tolyl-pent-1-en-3-ol

Example 215

1-(4-chlorophenyl)-5-dimethylamino-3-(4-methoxyphenyl)-2,4-dimethyl-pent-1-en-3-ol Example 216

1-(4-chlorophenyl)-3-cyclohexylmethyl-5-dimethylamino-2,4-dimethyl-pent-1-en-3-ol Example 217

1-(4-chlorophenyl)-5-dimethylamino-3-(5-fluoro-2-methoxyphenyl)-2,4-dimethyl-pent-1-en-3-ol Example 218

1-(4-chlorophenyl)-5-dimethylamino-3-(3-fluorophenyl)-2,4-dimethyl-pent-1-en-3-ol Example 219

3-(3-chlorophenyl)-1-(4-chlorophenyl)-5-dimethylamino-2,4-dimethyl-pent-1-en-3-ol Example 220

1-(4-chlorophenyl)-3-(3,5-dichlorophenyl)-5-dimethylamino-2,4-dimethyl-pent-1-en-3-ol Example 221

3-(2-chlorobenzyl)-1-(4-chlorophenyl)-5-dimethylamino-2,4-dimethyl-pent-1-en-3-ol Example 222

1-(4-chlorophenyl)-5-dimethylamino-3-(4-fluorobenzyl)-2,4-dimethyl-pent-1-en-3-ol Example 223

1-(4-chlorophenyl)-5-dimethylamino-3-(3-methoxybenzyl)-2,4-dimethyl-pent-1-en-3-ol Example 224

1-(4-chlorophenyl)-3-(4-chloro-3-trifluoromethylphenyl)-5-dimethylamino-2,4-dimethyl-pent-1-en-3-ol Example 225

1-(4-chlorophenyl)-5-dimethylamino-3-[2-(3-fluorophenyl)-ethyl]-2,4-dimethyl-pent-1-en-3-ol Example 226

1-(4-chlorophenyl)-5-dimethylamino-3-(2-methoxyphenyl)-2,4-dimethyl-pent-1-en-3-ol Example 227

1-(4-chlorophenyl)-5-dimethylamino-2,4-dimethyl-3-(2-methyl-benzyl)-pent-1-en-3-ol Example 228

3-(3-chloro-4-fluorophenyl)-1-(4-chlorophenyl)-5-dimethylamino-2,4-dimethyl-pent-1-en-3-ol Example 229

1-(4-chlorophenyl)-5-dimethylamino-2,4-dimethyl-3-(3-trifluoromethylphenyl)-pent-1-en-3-ol Example 230

1-(4-chlorophenyl)-5-dimethylamino-2,4-dimethyl-3-(3-methylbenzyl-pent-1-en-3-ol Example 231

3-(4-chlorobenzyl)-1-(4-chlorophenyl)-5-dimethylamino-2,4-dimethyl-pent-1-en-3-ol Example 232

3-(2-chloro-6-fluorobenzyl)-1-(4-chlorophenyl)-5-dimethylamino-2,4-dimethyl-pent-1-en-3-ol Example 233

1-(4-chlorophenyl)-5-dimethylamino-3-(2,5-dimethylbenzyl)-2,4-dimethyl-pent-1-en-3-ol Example 234

3-(3-chlorobenzyl)-1-(4-chlorophenyl)-5-dimethylamino-2,4-dimethyl-pent-1-en-3-ol Example 235

1-(4-chlorophenyl)-3-(2,4-dichlorobenzyl)-5-dimethylamino-2,4-dimethyl-pent-1-en-3-ol Example 236

5-dimethylamino-1-(4-methoxyphenyl)-2,4-dimethyl-3-phenyl-pent-1-en-3-ol

Example 237

3-(4-chlorophenyl)-5-dimethylamino-1-(4-methoxyphenyl)-2,4-dimethyl-pent-1-en-3-ol Example 238

3-benzyl-5-dimethylamino-1-(4-methoxyphenyl)-2,4-dimethyl-pent-1-en-3-ol

Example 239

5-dimethylamino-3-(4-fluoro-3-methylphenyl)-1-(4-methoxy-phenyl)-2,4-dimethyl-pent-1-en-3-ol Example 240

5-dimethylamino-1-(4-methoxyphenyl)-2,4-dimethyl-3-o-tolyl-pent-1-en-3-ol

Example 241

3-(2-dimethylamino-1-methylethyl)-1-(4-methoxyphenyl)-2-methyl-penta-1,4-dien-3-ol Example 242

3-(4-tert.-butylphenyl)-5-dimethylamino-1-(4-methoxyphenyl)-2,4-dimethyl-pent-1-en-3-ol Example 243

3-cyclopentyl-5-dimethylamino-1-(4-methoxyphenyl)-2,4-dimethyl-pent-1-en-3-ol

Example 244

5-dimethylamino-1-(4-methoxyphenyl)-2,4-dimethyl-3-m-tolyl-pent-1-en-3-ol

Example 245

3-cyclohexyl-5-dimethylamino-1-(4-methoxyphenyl)-2,4-dimethyl-pent-1-en-3-ol

Example 246

5-dimethylamino-3-(4-fluorophenyl)-1-(4-methoxyphenyl)-2,4-dimethyl-pent-1-en-3-ol Example 247

5-dimethylamino-1-(4-methoxyphenyl)-2,4-dimethyl-3-phenethyl-pent-1-en-3-ol

Example 248

3-(2-dimethylamino-1-methylethyl)-1-(4-methoxyphenyl)-2-methyl-5-phenyl-pent-1-en-4-yn-3-ol Example 249

5-dimethylamino-1-(4-methoxyphenyl)-2,4-dimethyl-3-thiophen-2-yl-pent-1-en-3-ol

Example 250

3-(2,4-dichlorophenyl)-5-dimethylamino-1-(4-methoxyphenyl)-2,4-dimethyl-pent-1-en-3-ol Example 251

5-dimethylamino-3-(3-methoxyphenyl)-1-(4-methoxyphenyl)-2,4-dimethyl-pent-1-en-3-ol Example 252

3-(2-dimethylamino-1-methylethyl)-1-(4-methoxyphenyl)-2-methyl-6-phenyl-hex-1-en-3-ol Example 253

3-(2,3-dichlorophenyl)-5-dimethylamino-1-(4-methoxyphenyl)-2,4-dimethyl-pent-1-en-3-ol Example 254

5-dimethylamino-1-(4-methoxyphenyl)-2,4-dimethyl-3-p-tolyl-pent-1-en-3-ol

Example 255

5-dimethylamino-1,3-bis-(4-methoxyphenyl)-2,4-dimethyl-pent-1-en-3-ol

Example 256

3-cyclohexylmethyl-5-dimethylamino-1-(4-methoxyphenyl)-2,4-dimethyl-pent-1-en-3-ol Example 257

5-dimethylamino-3-(5-fluoro-2-methoxyphenyl)-1-(4-methoxy-phenyl)-2,4-dimethyl-pent-1-en-3-ol Example 258

5-dimethylamino-3-(3-fluorophenyl)-1-(4-methoxyphenyl)-2,4-dimethyl-pent-1-en-3-ol Example 259

3-(3-chlorophenyl)-5-dimethylamino-1-(4-methoxyphenyl)-2,4-dimethyl-pent-1-en-3-ol Example 260

3-(3,5-dichlorophenyl)-5-dimethylamino-1-(4-methoxyphenyl)-2,4-dimethyl-pent-1-en-3-ol Example 261

3-(2-chlorobenzyl)-5-dimethylamino-1-(4-methoxyphenyl)-2,4-dimethyl-pent-1-en-3-ol Example 262

5-dimethylamino-3-(4-fluorobenzyl)-1-(4-methoxyphenyl)-2,4-dimethyl-pent-1-en-3-ol Example 263

5-dimethylamino-3-(3-fluorobenzyl)-1-(4-methoxyphenyl)-2,4-dimethyl-pent-1-en-3-ol Example 264

5-dimethylamino-3-(2-methoxyphenyl)-1-(4-methoxyphenyl )-2,4-dimethyl-pent-1-en-3-ol Example 265

5-dimethylamino-1-(4-methoxyphenyl)-2,4-dimethyl-3-(2-methylbenzyl)-pent-1-en-3-ol Example 266

3-(3-chloro-4-fluorophenyl)-5-dimethylamino-1-(4-methoxy-phenyl)-2,4-dimethyl-pent-1-en-3-ol Example 267

5-dimethylamino-1-(4-methoxyphenyl)-2,4-dimethyl-3-(3-trifluoromethylphenyl)-pent-1-en-3-ol Example 268

3-(4-chlorobenzyl)-5-dimethylamino-1-(4-methoxyphenyl)-2,4-dimethyl-pent-1-en-3-ol Example 269

3-(2-chloro-6-fluorobenzyl)-5-dimethylamino-1-(4-methoxyphenyl)-2,4-dimethyl-pent-1-en-3-ol Example 270

3-(3-chlorobenzyl)-5-dimethylamino-1-(4-methoxyphenyl)-2,4-dimethyl-pent-1-en-3-ol Example 271

2-benzylidene-1-(4-tert.-butylphenyl)-5-dimethylaminomethyl-cyclopentanol

Example 272

2-benzylidene-1-cyclohexyl-5-dimethylaminomethyl-cyclopentanol

Example 273

2-benzylidene-5-dimethylaminomethyl-1-phenethyl-cyclopentanol

Example 274

2-benzylidene-5-dimethylaminomethyl-1-(4-fluorobenzyl)-cyclopentanol

Example 275

2-benzylidene-5-dimethylaminomethyl-1-(3-fluorobenzyl)-cyclopentanol

Example 276

2-benzylidene-5-dimethylaminomethyl-1-(2-methoxyphenyl)-cyclopentanol

Example 277

2-benzylidene-5-dimethylaminomethyl-1-(2-methylbenzyl)-cyclopentanol

Example 278

2-benzylidene-5-dimethylaminomethyl-1-(3-methylbenzyl)-cyclopentanol

Example 279

2-benzylidene-1-(4-chlorobenzyl)-5-dimethylaminomethyl-cyclopentanol

Example 280

2-benzylidene-1-(2-chloro-6-fluorobenzyl)-5-dimethylaminomethyl-cyclopentanol

Example 281

2-benzylidene-5-dimethylaminomethyl-1-(2,5-dimethylbenzyl)-cyclopentanol

Example 282

2-benzylidene-1-(3-chlorobenzyl)-5-dimethylaminomethyl-cyclopentanol

Example 283

2-dimethylaminomethyl-5-(3-methoxybenzyl)-bicyclopentyl-1-ol

Example 284

2-dimethylaminomethyl-5-(3-methoxybenzyl)-1-m-tolyl-cyclopentanol

Example 285

1-cyclohexyl-2-dimethylaminomethyl-5-(3-methoxybenzyl)-cyclopentanol

Example 286

2-dimethylaminomethyl-5-(3-methoxybenzyl)-1-phenethyl-cyclopentanol

Example 287

2-dimethylaminomethyl-5-(3-methoxybenzyl)-1-phenylethynyl-cyclopentanol

Example 288

2-dimethylaminomethyl-5-(3-methoxybenzyl)-1-thiophen-2-yl-cyclopentanol

Example 289

2-dimethylaminomethyl-5-(3-methoxybenzyl)-1-(3-methoxy-phenyl)-cyclopentanol

Example 290

2-dimethylaminomethyl-5-(3-methoxybenzyl)-1-(3-phenylpropyl)-cyclopentanol

Example 291

2-dimethylaminomethyl-5-(3-methoxybenzyl)-1-(4-methoxy-phenyl)-cyclopentanol

Example 292

2-dimethylaminomethyl-1-(3-fluorobenzyl)-5-(3-methoxy-benzylidene)-cyclopentanol Example 293

2-dimethylaminomethyl-5-(3-methoxybenzylidene)-1-(2-methoxyphenyl)-cyclopentanol Example 294

2-dimethylaminomethyl-5-(3-methoxybenzylidene)-1-(2-methylbenzyl)-cyclopentanol

Example 295

2-dimethylaminomethyl-5-(3-methoxybenzylidene)-1-(3-methyl-benzyl)-cyclopentanol Example 296
2-dimethylaminomethyl-1-(2,5-dimethylbenzyl)-5-(3-methoxy-benzylidene)-cyclopentanol Example 297
1-(3-chlorobenzyl)-2-dimethylaminomethyl-5-(3-methoxy-benzylidene)-cyclopentanol Example 298
1-benzyl-2-dimethylaminomethyl-5-(methoxybenzylidene)-cyclopentanol Example 299
2-dimethylaminomethyl-5-(3-methoxybenzylidene)-1-o-tolyl-cyclopentanol Example 300
2-dimethylaminomethyl-5-(3-methoxybenzylidene)-1-vinyl-cyclopentanol Example 301
1-(4-tert.-butylphenyl)-2-dimethylaminomethyl-5-(3-methoxy-benzylidene)-cyclopentanol Example 302
2-dimethylaminomethyl-5-(3-methoxybenzylidene)-bicyclopentyl-1-ol Example 303
1-cyclohexyl-2-dimethylaminomethyl-5-(3-methoxybenzylidene)-cyclopentanol Example 304
2-dimethylaminomethyl-1-(4-fluorophenyl)-5-(3-methoxy-benzylidene)-cyclopentanol Example 305
2-dimethylaminomethyl-5-(3-methoxybenzylidene)-1-phenethyl-cyclopentanol Example 306
2-dimethylaminomethyl-5-(3-methoxybenzylidene)-1-phenyl-ethynyl-cyclopentanol Example 307
2-dimethylaminomethyl-5-(3-methoxybenzylidene)-1-thiophen-2-yl-cyclopentanol Example 308
2-dimethylaminomethyl-5-(3-methoxybenzylidene)-1-(3-methoxyphenyl)-cyclopentanol Example 309
2-dimethylaminomethyl-5-(3-methoxybenzylidene)-1-(3-phenyl-propyl)-cyclopentanol Example 310
2-dimethylaminomethyl-5-(3-methoxybenzylidene)-1-p-tolyl-cyclopentanol Example 311
2-dimethylaminomethyl-5-(3-methoxybenzylidene)-1-(4-methoxyphenyl)-cyclopentanol Example 312
1-(2-chlorobenzyl)-2-dimethylaminomethyl-5-(4-methoxy-benzylidene)-cyclopentanol Example 313
2-dimethylaminomethyl-1-(3-methoxybenzyl)-5-(4-methoxy-benzylidene)-cyclopentanol Example 314
2-dimethylaminomethyl-1-(3-fluorobenzyl)-5-(4-methoxy-benzylidene)-cyclopentanol Example 315
2-dimethylaminomethyl-5-(4-methoxybenzylidene)-1-(2-methoxyphenyl)-cyclopentanol Example 316
2-dimethylaminomethyl-5-(4-methoxybenzylidene)-1-(3-methylbenzyl)-cyclopentanol Example 317
1-(4-chlorobenzyl)-2-dimethylaminomethyl-5-(4-methoxy-benzylidene)-cyclopentanol Example 318
1-(2-chloro-6-fluorobenzyl)-2-dimethylaminomethyl-5-(4-methoxybenzylidene)-cyclopentanol Example 319
1-(3-chlorobenzyl)-2-dimethylaminomethyl-5-(4-methoxy-benzylidene)-cyclopentanol Example 320
1-(2,4-dichlorobenzyl)-2-dimethylaminomethyl-5-(4-methoxy-benzylidene)-cyclopentanol Example 321
2-benzylidene-7-dimethylaminomethyl-1-phenyl-cycloheptanol Example 322
2-benzylidene-1-(4-chlorophenyl)-7-dimethylaminomethyl-cycloheptanol Example 323
1-benzyl-2-benzylidene-7-dimethylaminomethyl-cycloheptanol Example 324
2-benzylidene-7-dimethylaminomethyl-1-(4-fluoro-3-methyl-phenyl)-cycloheptanol Example 325
2-benzylidene-7-dimethylaminomethyl-1-o-tolyl-cycloheptanol Example 326
2-benzylidene-7-dimethylaminomethyl-1-vinyl-cycloheptanol Example 327
2-benzylidene-1-(4-tert.-butylphenyl)-7-dimethylaminomethyl-cycloheptanol Example 328
2-benzylidene-1-cyclopentyl-7-dimethylaminomethyl-cycloheptanol Example 329
2-benzylidene-7-dimethylaminomethyl-1-m-tolyl-cycloheptanol Example 330
2-benzylidene-1-cyclohexyl-7-dimethylaminomethyl-cycloheptanol Example 331
2-benzylidene-7-dimethylaminomethyl-1-(4-fluorophenyl)-cycloheptanol Example 332

2-benzylidene-7-dimethylaminomethyl-1-phenylethynyl-cycloheptanol

Example 333

2-benzylidene-7-dimethylaminomethyl-1-thiophen-2-yl-cycloheptanol

Example 334

2-benzylidene-7-dimethylaminomethyl-1-(3-methoxyphenyl)-cycloheptanol

Example 335

2-benzylidene-1-cyclohexylmethyl-7-dimethylaminomethyl-cycloheptanol

Example 336

2-benzylidene-7-dimethylaminomethyl-1-(3-fluoro-4-methoxy-phenyl)-cycloheptanol

Example 337

2-benzylidene-7-dimethylaminomethyl-1-(3-fluorophenyl)-cycloheptanol

Example 338

2-benzylidene-1-(3-chlorophenyl)-7-dimethylaminomethyl-cycloheptanol

Example 339

2-benzylidene-7-(3,5-dichlorophenyl)-7-dimethylaminomethyl-cycloheptanol

Example 340

2-benzylidene-7-dimethylaminomethyl-1-(4-fluorobenzyl)-cycloheptanol

Example 341

2-benzylidene-7-dimethylaminomethyl-1-(4-methoxybenzyl)-cycloheptanol

Example 342

2-benzylidene-7-dimethylaminomethyl-1-(3-fluorobenzyl)-cycloheptanol

Example 343

2-benzylidene-7-dimethylaminomethyl-1-(2-methoxyphenyl)-cycloheptanol

Example 344

2-benzylidene-7-dimethylaminomethyl-1-(2-methylbenzyl)-cycloheptanol

Example 345

2-benzylidene-1-(3-chloro-4-fluorophenyl)-7-dimethylaminomethyl-cycloheptanol

Example 346

2-benzylidene-7-dimethylaminomethyl-1-(3-trifluoromethylphenyl)-cycloheptanol

Example 347

2-benzylidene-7-dimethylaminomethyl-1-(3-methylbenzyl)-cycloheptanol

Example 348

2-benzylidene-1-(4-chlorobenzyl)-7-dimethylaminomethyl-cycloheptanol

Example 349

2-benzylidene-1-(2-chloro-6-fluorobenzyl)-7-dimethylaminomethyl-cycloheptanol

Example 350

2-benzylidene-7-dimethylaminomethyl-1-(2,5-dimethylbenzyl)-cycloheptanol

Example 351

2-benzylidene-1-(3-chlorobenzyl)-7-dimethylaminomethyl-cycloheptanol

Example 352

2-dimethylaminomethyl-7-(3-methoxybenzylidene)-1-phenyl-cycloheptanol

Example 353

1-(4-chlorophenyl)-2-dimethylaminomethyl-7-(3-methoxy-benzylidene)-cycloheptanol Example 354

1-benzyl-2-dimethylaminomethyl-7-(3-methoxybenzylidene)-cycloheptanol

Example 355

2-dimethylaminomethyl-1-(4-fluoro-3-methylphenyl)-7-(3-methoxybenzylidene)-cycloheptanol Example 356

2-dimethylaminomethyl-7-(3-methoxybenzylidene)-1-o-tolyl-cycloheptanol

Example 357

2-dimethylaminomethyl-7-(3-methoxybenzylidene)-1-vinyl-cycloheptanol

Example 358

1-(4-tert.-butylphenyl)-2-dimethylaminomethyl-7-(3-methoxy-benzylidene)-cycloheptanol Example 359

1-cyclopentyl-2-dimethylaminomethyl-7-(3-methoxybenzylidene)-cycloheptanol

Example 360

2-dimethylaminomethyl-7-(3-methoxybenzylidene)-1-m-tolyl-cycloheptanol

Example 361

1-cyclohexyl-2-dimethylaminomethyl-7-(3-methoxybenzylidene)-cycloheptanol

Example 362

2-dimethylaminomethyl-1-(4-fluorophenyl)-7-(3-methoxy-benzylidene)-cycloheptanol Example 363

2-dimethylaminomethyl-7-(3-methoxybenzylidene)-1-phenethyl-cycloheptanol

Example 364

2-dimethylaminomethyl-7-(3-methoxybenzylidene)-1-phenyl-ethynyl-cycloheptanol

Example 365

2-dimethylaminomethyl-7-(3-methoxybenzylidene)-1-thiophen-2-yl-cycloheptanol

Example 366

2-dimethylaminomethyl-7-(3-methoxybenzylidene)-1-(3-methoxyphenyl)-cycloheptanol Example 367

2-dimethylaminomethyl-7-(3-methoxybenzylidene)-1-(3-phenylpropyl)-cycloheptanol

Example 368

2-dimethylaminomethyl-7-(3-methoxybenzylidene)-1-p-tolyl-cycloheptanol

Example 369

2-dimethylaminomethyl-7-(3-methoxybenzylidene)-1-(4-methoxyphenyl)-cycloheptanol Example 370

1-cyclohexylmethyl-2-dimethylaminomethyl-7-(3-methoxy-benzylidene)-cycloheptanol Example 371

1-(3-chlorophenyl)-2-dimethylaminomethyl-7-(3-methoxy-benzylidene)-cycloheptanol Example 372

1-(3,5-dichlorophenyl)-2-dimethylaminomethyl-7-(3-methoxy-benzylidene)-cycloheptanol Example 373

1-(2-chlorobenzyl)-2-dimethylaminomethyl-7-(3-methoxy-benzylidene)-cycloheptanol Example 374

1-(4-chloro-3-trifluoromethylphenyl)-2-dimethylaminomethyl-7-(3-methoxybenzylidene)-cycloheptanol Example 375

2-dimethylaminomethyl-1-(3-fluorophenyl)-7-(3-methoxy-benzylidene)-cycloheptanol Example 376

2-dimethylaminomethyl-7-(3-methoxybenzylidene)-1-(2-methoxy-phenyl)-cycloheptanol Example 377

2-dimethylaminomethyl-7-(3-methoxybenzylidene)-1-(2-methyl-benzyl)-cycloheptanol Example 378

2-dimethylaminomethyl-7-(3-methoxybenzylidene)-1-(3-trifluoro-methylphenyl)-cycloheptanol Example 379

2-dimethylaminomethyl-7-(3-methoxybenzylidene)-1-(3-methyl-benzyl)-cycloheptanol Example 380

2-dimethylaminomethyl-1-(2,5-dimethylbenzyl)-7-(3-methoxy-benzylidene)-cycloheptanol Example 381

1-(3-chlorobenzyl)-2-dimethylaminomethyl-7-(3-methoxy-benzylidene)-cycloheptanol Example 382

1-benzyl-2-dimethylaminomethyl-7-(4-methoxybenzylidene)-cycloheptanol

Example 383

2-dimethylaminomethyl-1-(4-fluoro-3-methylphenyl)-7-(4-methoxy-benzylidene)-cycloheptanol Example 384

2-dimethylaminomethyl-7-(4-methoxybenzylidene)-1-o-tolyl-cycloheptanol

Example 385

2-dimethylaminomethyl-7-(4-methoxybenzylidene)-1-vinyl-cycloheptanol

Example 386

1-(4-tert.-butylphenyl)-2-dimethylaminomethyl-7-(4-methoxy-benzylidene)-cycloheptanol Example 387

1-cyclopentyl-2-dimethylaminomethyl-7-(4-methoxybenzylidene)-cycloheptanol

Example 388

2-dimethylaminomethyl-7-(4-methoxybenzylidene)-1-m-tolyl-cycloheptanol

Example 389

1-cyclohexyl-2-dimethylaminomethyl-7-(4-methoxybenzylidene)-cycloheptanol

Example 390

2-dimethylaminomethyl-1-(4-fluorophenyl)-7-(4-methoxy-benzylidene)-cycloheptanol Example 391

2-dimethylaminomethyl-7-(4-methoxybenzylidene)-1-phenethyl-cycloheptanol

Example 392

2-dimethylaminomethyl-7-(4-methoxybenzylidene)-1-phenylethynyl-cycloheptanol

Example 393

2-dimethylaminomethyl-7-(4-methoxybenzylidene)-1-thiophen-2-yl-cycloheptanol

Example 394

2-dimethylaminomethyl-7-(4-methoxybenzylidene)-1-(3-methoxy-phenyl)-cycloheptanol Example 395

2-dimethylaminomethyl-7-(4-methoxybenzylidene)-1-(3-phenyl-propyl)-cycloheptanol Example 396

2-dimethylaminomethyl-7-(4-methoxybenzylidene)-1-p-tolyl-cycloheptanol

Example 397

2-dimethylaminomethyl-7-(4-methoxybenzylidene)-1-(4-methoxy-phenyl)-cycloheptanol Example 398

1-cyclohexylmethyl-2-dimethylaminomethyl-7-(4-methoxy-benzylidene)-cycloheptanol Example 399

1-(3-chlorophenyl)-2-dimethylaminomethyl-7-(4-methoxy-benzylidene)-cycloheptanol Example 400

1-(2-chlorobenzyl)-2-dimethylaminomethyl-7-(4-methoxybenzylidene)-cycloheptanol

Example 401

2-dimethylaminomethyl-7-(4-methoxybenzylidene)-1-(2-methoxyphenyl)-cycloheptanol Example 402

2-dimethylaminomethyl-7-(4-methoxybenzylidene)-1-(2-methyl-benzyl)-cycloheptanol Example 403

2-dimethylaminomethyl-7-(4-methoxybenzylidene)-1-(3-trifluoro-methylphenyl)-cycloheptanol Example 404

2-dimethylaminomethyl-7-(4-methoxybenzylidene)-1-(3-methyl-benzyl)-cycloheptanol Example 405

1-(3-chlorobenzyl)-2-dimethylaminomethyl-7-(4-methoxy-benzylidene)-cycloheptanol Example 406

1-(3,5-dichlorophenyl)-2-dimethylaminomethyl-7-(4-methoxy-benzylidene)-cycloheptanol Example 407

2-benzylidene-7-dimethylaminomethyl-1-(3-hydroxyphenyl)-cycloheptanol, hydrochloride Example 408

2-dimethylaminomethyl-1-(3-hydroxyphenyl)-7-(3-methoxy-benzylidene)-cycloheptanol, hydrochloride Example 409

2-benzylidene-7-dimethylaminomethyl-1-(3-methoxyphenyl)-cycloheptanol, hydrochloride Example 410

3-[1-(2-dimethylaminomethyl-1-methylethyl)-1-hydroxy-2-methyl-3-phenyl-allyl]-phenol, hydrochloride Example 411

3-(4-chlorobenzyl)-5-dimethylamino-2,4-dimethyl-1-phenyl-pent-1-en-3-ol, hydrochloride Example 412

5-dimethylamino-3-(3-methoxyphenyl)-2,4-dimethyl-1-phenyl-pent-1-en-3-ol, hydrochloride Example 413

3-(2-benzylidene-6-dimethylaminomethyl-1-hydroxycyclohexyl)-phenol, hydrochloride Example 414

1-benzyl-2-benzylidene-7-(4-methylpiperazin-1-ylmethyl)-cycloheptanol, dihydrochloride Example 415

2-benzylidene-1-(2-chlorobenzyl)-7-(4-methylpiperazin-1-ylmethyl)-cycloheptanol, dihydrochloride Example 416

2-benzylidene-1-(3-chlorobenzyl)-7-(4-methylpiperazin-1-ylmethyl)-cycloheptanol, dihydrochloride Example 417

2-benzylidene-1-(4-chlorobenzyl)-7-(4-methylpiperazin-1-ylmethyl)-cycloheptanol, dihydrochloride Example 418

2-benzylidene-1-(2-fluorobenzyl)-7-(4-methylpiperazin-1-ylmethyl)-cycloheptanol, dihydrochloride Example 419

2-benzylidene-1-(3-fluorobenzyl)-7-(4-methylpiperazin-1-ylmethyl)-cycloheptanol, dihydrochloride Example 420

2-benzylidene-1-(4-fluorobenzyl)-7-(4-methylpiperazin-1-ylmethyl)-cycloheptanol, dihydrochloride Example 421

2-benzylidene-1-(2-methylbenzyl)-7-(4-methylpiperazin-1-ylmethyl)-cycloheptanol, dihydrochloride Example 422

2-benzylidene-1-(3-methylbenzyl)-7-(4-methylpiperazin-1-ylmethyl)-cycloheptanol, dihydrochloride Example 423

2-benzylidene-1-(4-methylbenzyl)-7-(4-methylpiperazin-1-ylmethyl)-cycloheptanol, dihydrochloride Example 424

2-benzylidene-1-(2-methoxybenzyl)-7-(4-methylpiperazin-1-ylmethyl)-cycloheptanol, dihydrochloride Example 425

2-benzylidene-1-(3-methoxybenzyl)-7-(4-methylpiperazin-1-ylmethyl)-cycloheptanol, dihydrochloride Example 426

2-benzylidene-1-(4-methoxybenzyl)-7-(4-methylpiperazin-1-ylmethyl)-cycloheptanol, dihydrochloride Example 427

2-benzylidene-1-(2,6-dichlorobenzyl)-7-(4-methylpiperazin-1-ylmethyl)-cycloheptanol, dihydrochloride Example 428

2-benzylidene-1-(2-chloro-6-fluorobenzyl)-7-(4-methylpiperazin-1-ylmethyl)-cycloheptanol, dihydrochloride Example 429

2-benzylidene-(2,6-difluorobenzyl)-7-(4-methylpiperazin-1-ylmethyl)-cycloheptanol, dihydrochloride Example 430

1-benzyl-2-(4-chlorobenzylidene)-7-(4-methylpiperazin-1-ylmethyl)-cycloheptanol, dihydrochloride Example 431

1-(2-chlorobenzyl)-2-(4-chlorobenzylidene)-7-(4-methylpiperazin-1-ylmethyl)-cycloheptanol, dihydrochloride Example 432

1-(3-chlorobenzyl)-2-(4-chlorobenzylidene)-7-(4-methylpiperazin-1-ylmethyl)-cycloheptanol, dihydrochloride Example 433

1-(4-chlorobenzyl)-2-(4-chlorobenzyliden)-7-(4-methylpiperazin-1-ylmethyl)-cycloheptanol, dihydrochloride Example 434

2-(4-chlorobenzylidene)-1-(2-fluorobenzyl)-7-(4-methylpiperazin-1-ylmethyl)-cycloheptanol, dihydrochloride Example 435

2-(4-chlorobenzylidene)-1-(3-fluorobenzyl)-7-(4-methylpiperazin-1-ylmethyl)-cycloheptanol, dihydrochloride Example 436

2-(4-chlorobenzylidene)-1-(4-fluorobenzyl)-7-(4-methylpiperazin-1-ylmethyl)-cycloheptanol, dihydrochloride Example 437

2-(4-chlorobenzylidene)-1-(2-methylbenzyl)-7-(4-methylpiperazin-1-ylmethyl)-cycloheptanol, dihydrochloride Example 438

2-(4-chlorobenzylidene)-1-(3-methylbenzyl)-7-(4-methylpiperazin-1-ylmethyl)-cycloheptanol, dihydrochloride Example 439

2-(4-chlorobenzylidene)-1-(4-methylbenzyl)-7-(4-methylpiperazin-1-ylmethyl)-cycloheptanol, dihydrochloride Example 440

2-(4-chlorobenzylidene)-1-(2-methoxybenzyl)-7-(4-methylpiperazin-1-ylmethyl)-cycloheptanol, dihydrochloride Example 441

2-(4-chlorobenzylidene)-1-(3-methoxybenzyl)-7-(4-methylpiperazin-1-ylmethyl)-cycloheptanol, dihydrochloride Example 442

2-(4-chlorobenzylidene)-1-(4-methoxybenzyl)-7-(4-methylpiperazin-1-ylmethyl)-cycloheptanol, dihydrochloride Example 443

2-(4-chlorobenzylidene)-1-(2,6-dichlorobenzyl)-7-(4-methyl-piperazin-1-ylmethyl)-cycloheptanol, dihydrochloride Example 444

2-(4-chlorobenzylidene)-1-(2,6-difluorobenzyl)-7-(4-methyl-piperazin-1-ylmethyl)-cycloheptanol, dihydrochloride Example 445

2-(4-chlorobenzylidene)-1-(2-chloro-6-fluorobenzyl)-7-(4-methyl-piperazin-1-ylmethyl)-cycloheptanol, dihydrochloride Example 446

1-benzyl-2-(4-fluorobenzylidene)-7-(4-methylpiperazin-1-ylmethyl)-cycloheptanol, dihydrochloride Example 447

2-(2-chlorobenzyl)-2-(4-fluorobenzylidene)-7-(4-methylpiperazin-1-ylmethyl)-cycloheptanol, dihydrochloride Example 448

1-(3-chlorobenzyl)-2-(4-fluorobenzylidene)-7-(4-methylpiperazin-1-ylmethyl)-cycloheptanol, dihydrochloride Example 449

1-(4-chlorobenzyl)-2-(4-fluorobenzylidene)-7-(4-methylpiperazin-1-ylmethyl)-cycloheptanol, dihydrochloride Example 450

1-(2-fluorobenzyl)-2-(4-fluorobenzylidene)-7-(4-methylpiperazin-1-ylmethyl)-cycloheptanol, dihydrochloride Example 451

2-(3-fluorobenzyl)-2-(4-fluorobenzylidene)-7-(4-methylpiperazin-1-ylmethyl)-cycloheptanol, dihydrochloride Example 452

1-(4-fluorobenzy)-2-(4-fluorobenzylidene)-7-(4-methylpiperazin-1-ylmethyl)-cycloheptanol, dihydrochloride Example 453

2-(4-fluorobenzylidene)-1-(2-methylbenzyl)-7-(4-methylpiperazin-1-ylmethyl)-cycloheptanol, dihydrochloride Example 454

2-(4-fluorobenzylidene)-1-(3-methylbenzyl)-7-(4-methylpiperazin-1-ylmethyl)-cycloheptanol, dihydrochloride Example 455

2-(4-fluorobenzylidene)-1-(4-methylbenzyl)-7-(4-methylpiperazin-1-ylmethyl)-cycloheptanol, dihydrochloride Example 456

2-(4-fluorobenzylidene)-1-(2-methoxybenzyl)-7-(4-methylpiperazin-1-ylmethyl)-cycloheptanol, dihydrochloride Example 457

2-(4-fluorobenzylidene)-1-(3-methoxybenzyl)-7-(4-methylpiperazin-1-ylmethyl)-cycloheptanol, dihydrochloride Example 458

2-(4-fluorobenzylidene)-1-(4-methoxybenzyl)-7-(4-methylpiperazin-1-ylmethyl)-cycloheptanol, dihydrochloride Example 459

1-(2,6-dichlorobenzyl)-2-(4-fluorobenzylidene)-7-(4-methyl-piperazin-1-ylmethyl)-cycloheptanol, dihydrochloride Example 460

1-(2,6-difluorobenzyl)-2-(4-fluorobenzylidene)-7-(4-methyl-piperazin-1-ylmethyl)-cycloheptanol, dihydrochloride Example 461

1-(2-chloro-6-fluorobenzyl)-2-(4-fluorobenzylidene)-7-(4-methyl-piperazin-1-ylmethyl)-cycloheptanol, dihydrochloride Example 462

1-benzyl-2-furan-2-ylmethylene-7-(4-methylpiperazin-1-ylmethyl)-cycloheptanol, dihydrochloride Example 463

1-(2-chlorobenzyl)-2-furan-2-ylmethylene-7-(4-methylpiperazin-1-ylmethyl)-cycloheptanol, dihydrochloride Example 464

1-(3-chlorobenzyl)-2-furan-2-ylmethylene-7-(4-methylpiperazin-1-ylmethyl)-cycloheptanol, dihydrochloride Example 465

1-(4-chlorobenzyl)-2-furan-2-ylmethylene-7-(4-methylpiperazin-1-ylmethyl)-cycloheptanol, dihydrochloride Example 466

1-(2-fluorobenzyl)-2-furan-2-ylmethylene-7-(4-methylpiperazin-1-ylmethyl)-cycloheptanol, dihydrochloride Example 467

1-(3-fluorobenzyl)-2-furan-2-ylmethylene-7-(4-methylpiperazin-1-ylmethyl)-cycloheptanol, dihydrochloride Example 468

1-(4-fluorobenzyl)-2-furan-2-ylmethylene-7-(4-methylpiperazin-1-ylmethyl)-cycloheptanol, dihydrochloride Example 469

2-furan-2-ylmethylene-1-(2-methylbenzyl)-7-(4-methylpiperazin-1-ylmethyl)-cycloheptanol, dihydrochloride Example 470

2-furan-2-ylmethylene-1-(3-methylbenzyl)-7-(4-methylpiperazin-1-ylmethyl)-cycloheptanol, dihydrochloride Example 471

2-furan-2-ylmethylene-1-(4-methylbenzyl)-7-(4-methylpiperazin-1-ylmethyl)-cycloheptanol, dihydrochloride Example 472

2-furan-2-ylmethylene-1-(2-methoxybenzyl)-7-(4-methylpiperazin-1-ylmethyl)-cycloheptanol, dihydrochloride Example 473

2-furan-2-ylmethylene-1-(3-methoxybenzyl)-7-(4-methylpiperazin-1-ylmethyl)-cycloheptanol, dihydrochloride Example 474

2-furan-2-ylmethylene-1-(4-methoxybenzyl)-7-(4-methylpiperazin-1-ylmethyl)-cycloheptanol, dihydrochloride Example 475

1-(2,6-dichlorobenzyl)-2-furan-2-ylmethylene-7-(4-methylpiperazin-1-ylmethyl)-cycloheptanol, dihydrochloride Example 476

1-(2,6-difluorobenzyl)-2-furan-2-ylmethylene-7-(4-methylpiperazin-1-ylmethyl)-cycloheptanol, dihydrochloride Example 477

1-(2-chloro-6-fluorobenzyl)-2-furan-2-ylmethylene-7-(4-methyl-piperazin-1-ylmethyl)-cycloheptanol, dihydrochloride Example 478

1-benzyl-3-furan-2-ylmethylene-7-(4-methylpiperazin-1-ylmethyl)-cycloheptanol, dihydrochloride Example 479

1-(2-chlorobenzyl)-3-furan-2-ylmethylene-7-(4-methylpiperazin-1-ylmethyl)-cycloheptanol, dihydrochloride Example 480

1-(3-chlorobenzyl)-3-furan-2-ylmethylene-7-(4-methylpiperazin-1-ylmethyl)-cycloheptanol, dihydrochloride Example 481

1-(4-chlorobenzyl)-3-furan-2-ylmethylene-7-(4-methylpiperazin-1-ylmethyl)-cycloheptanol, dihydrochloride Example 482

1-(2-fluorobenzyl)-3-furan-2-ylmethylene-7-(4-methylpiperazin-1-ylmethyl)-cycloheptanol, dihydrochloride Example 483

1-(3-fluorobenzyl)-3-furan-2-ylmethylene-7-(4-methylpiperazin-1-ylmethyl)-cycloheptanol, dihydrochloride Example 484

1-(4-fluorobenzyl)-3-furan-2-ylmethylene-7-(4-methylpiperazin-1-ylmethyl)-cycloheptanol, dihydrochloride Example 485

3-furan-2-ylmethylene-1-(2-methylbenzyl)-7-(4-methylpiperazin-1-ylmethyl)-cycloheptanol, dihydrochloride Example 486

3-furan-2-ylmethylene-1-(3-methylbenzyl)-7-(4-methylpiperazin-1-ylmethyl)-cycloheptanol, dihydrochloride Example 487

3-furan-2-ylmethylene-1-(4-methylbenzyl)-7-(4-methylpiperazin-1-ylmethyl)-cycloheptanol, dihydrochloride Example 488

3-furan-2-ylmethylene-1-(2-methoxybenzyl)-7-(4-methylpiperazin-1-ylmethyl)-cycloheptanol, dihydrochloride Example 489

3-furan-2-ylmethylene-1-(3-methoxybenzyl)-7-(4-methylpiperazin-1-ylmethyl)-cycloheptanol, dihydrochloride Example 490

3-furan-2-ylmethylene-1-(4-methoxybenzyl)-7-(4-methylpiperazin-1-ylmethyl)-cycloheptanol, dihydrochloride Example 491

1-(2,6-dichlorobenzyl)-3-furan-2-ylmethylene-7-(4-methylpiperazin-1-ylmethyl)-cycloheptanol, dihydrochloride Example 492

1-(2,6-difluorobenzyl)-3-furan-2-ylmethylene-7-(4-methylpiperazin-1-ylmethyl)-cycloheptanol, dihydrochloride Example 493

1-(2-chloro-6-fluorobenzyl)-3-furan-2-ylmethylene-7-(4-methyl-piperazin-1-ylmethyl)-cycloheptanol, dihydrochloride Pharmacological Investigations Gabapentin is used in the binding assay in order to investigate the binding and affinities of the selected compounds. The affinity of the compounds according to the invention is measured via the displacement of gabapentin from its binding site. If the chosen compounds are able to displace gabapentin from its binding site, then it may be expected that they will exhibit comparable pharmacological properties to gabapentin, for example that they will be effective in treating pain or epilepsy. The compounds according to the invention exhibit a good inhibition/displacement of gabapentin in this assay. The investigated compounds accordingly exhibit in this biochemical assay an affinity for the as yet unknown gabapentin binding site.

| Example | % Inhibition gabapentin, 10 μmole |
|---|---|
| 120 | 37 |
| 152 | 30 |
| 156 | 46 |
| 184 | 47 |
| 223 | 40 |
| 369 | 43 |
| 353 | 44 |

Analgesia Investigation in the Writhing Test in Mice

The investigation of the analgesic efficacy was carried out according to the phenylquinone-induced writhing test in mice (as modified by I. C. Hendershot and J. Forsaith J. Pharmacol. Exp. Ther. 1959 125, 237–240). For this purpose male NMRI mice weighing 25 to 30 g were used. Groups of 10 animals per substance dose received, 10 minutes after intravenous administration of the test substances, 0.3 ml/mouse of a 0.02% aqueous solution of phenylquinone (phenyl benzoquinone, from Sigma, Deisenhofen; solution prepared by addition of 5% of ethanol and storage in a water bath at 45° C.) applied intraperitoneally. The animals were placed individually in observation cages. The number of pain-induced stretching movements (so-called writhing reactions=contortion of the body accompanied by stretching of the rear extremities) was counted using a push-button counter 5 to 20 minutes after administration of the phenylquinone. Animals that had received only physiological saline served as controls. The number of responding animals was determined for some of the examples.

| Example | Responding Animals/Control Animals (Writhing IV) |
|---|---|
| 407 | 6/10 (2.15 mg/kg) |
| 408 | 9/10 (10 mg/kg) |
| 409 | 5/10 (10 mg/kg) |
| 410 | 5/10 (10 mg/kg) |
| 411 | 3/10 (10 mg/kg) |
| 412 | 9/10 (10 mg/kg) |
| 413 | 4/10 (10 mg/kg) |

What is claimed is:

1. A compound of formula I,

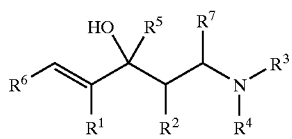

I wherein $R^1$ and $R^2$ independently of one another are $C_{1-6}$ alkyl, branched or unbranched, saturated or unsaturated, unsubstituted or singly or multiply substituted, or $R^1$ and $R^2$ together form a $(CH_2)_{2-9}$ ring that may optionally be substituted by $C_{1-8}$ alkyl, which is branched or unbranched, saturated or unsaturated, unsubstituted or singly or multiply substituted; or by aryl, unsubstituted or singly or multiply substituted, $R^3$ and $R^4$ independently of one another are $C_{1-6}$ alkyl, branched or unbranched, saturated or unsaturated, unsubstituted or singly or multiply substituted; $C_{3-6}$ cycloalkyl, saturated or unsaturated, unsubstituted or singly or multiply substituted; or phenyl, benzyl or phenethyl, unsubstituted or singly or multiply substituted, or $R^3$ and $R^4$ together form a ring and denote $CH_2CH_2OCH_2CH_2$, $CH_2CH_2NR^{22}CH_2CH_2$ or $(CH_2)_{3-6}$, wherein $R^{22}$ is H; $C_{1-10}$ alkyl or $C_{3-10}$ cycloalkyl that is saturated or unsaturated, branched or unbranched, singly or multiply substituted or unsubstituted; aryl or heteroaryl, singly or multiply substituted or unsubstituted; or aryl bound via $C_{1-3}$ alkyl that is saturated or unsaturated, via $C_{3-10}$ cycloalkyl or via heteroaryl, singly or multiply substituted or unsubstituted, $R^5$ is $C_{1-10}$ alkyl, saturated or unsaturated, branched or unbranched, singly or multiply substituted or unsubstituted; $C_{3-9}$ cycloalkyl, saturated or unsaturated, aryl, heteroaryl, aryl bound via saturated or unsaturated $C_{1-3}$ alkyl; $C_{3-10}$ cycloalkyl bound via saturated or unsaturated $C_{1-3}$ alkyl; or heteroalkyl bound via saturated or unsaturated $C_{1-3}$ alkyl, wherein all aryl, heteroaryl and cycloalkyl may independently of one another be unsubstituted or may be independently singly or multiply substituted with F, Cl, Br, I, $OR^{18}$, $SR^{18}$, $SO_2R^{18}$, $SO_2OR^{18}$, CN, $COOR^{18}$, $NR^{19}R^{20}$; $C_1$–$C_{10}$ alkyl, saturated or unsaturated, branched or unbranched, singly or multiply substituted or unsubstituted; $C_{3-9}$ cycloalkyl, saturated or unsaturated, unsubstituted or singly or multiply substituted; aryl or heteroaryl, in each case unsubstituted or singly or multiply substituted; or aryl, $C_{3-9}$ cycloalkyl or heteroaryl bound via saturated or unsaturated $C_{1-3}$ alkyl, which may be unsubstituted or singly or multiply substituted, wherein $R^{18}$ is H; $C_{1-10}$ alkyl, saturated or unsaturated, branched or unbranched, unsubstituted or singly or multiply substituted; $C_{3-9}$ cycloalkyl, saturated or unsaturated, unsubstituted or singly or multiply substituted; aryl or heteroaryl, unsubstituted or singly or multiply substituted; or aryl, $C_{3-9}$ cycloalkyl or heteroaryl bound via saturated or unsaturated $C_{1-3}$ alkyl which may be unsubstituted or singly or multiply substituted; and wherein $R^{19}$ and $R^{20}$ independently of one another are H; $C_{1-10}$ alkyl, saturated or unsaturated, branched or unbranched, unsubstituted or singly or multiply substituted; $C_{3-9}$ cycloalkyl, saturated or unsaturated, unsubstituted or singly or multiply substituted; aryl or heteroaryl, unsubstituted or singly or multiply substituted; or aryl, $C_{3-9}$ cycloalkyl or heteroaryl bound via saturated or unsaturated $C_{1-3}$ alkyl which may be unsubstituted or singly or multiply substituted;

or $R^{19}$ and $R^{20}$ together form $CH_2CH_2OCH_2CH_2$, $CH_2CH_2NR^{21}CH_2CH_2$ or $(CH_2)_{3-6}$, where $R^{21}$ is H; substituted or unsubstituted phenyl; $C_{1-10}$ alkyl, saturated or unsaturated, branched or unbranched, unsubstituted or singly or multiply substituted;

$R^6$ is $C_{1-10}$ alkyl, saturated or unsaturated, branched or unbranched, singly or multiply substituted or unsubstituted; or $C_{5-7}$ cycloalkyl, aryl or heteroaryl, unsubstituted or singly or multiply substituted;

$R^7$ is H; aryl or heteroaryl; unsubstituted or singly or multiply substituted, or a derivative thereof in the form of an acid, a base, a salt, or a solvate.

2. A compound according to claim 1, wherein the derivative is a pharmaceutically acceptable salt, or a hydrate.

3. A compound according to claim 1, wherein the compound is in the form of a racemate, a pure stereoisomer, or a mixture of stereoisomers in any mixing ratio.

4. A compound according to claim 3, wherein the compound is in the form of a pure enantiomer, a pure diastereomer, a mixture of diastereomers in any mixing ratio, or a mixture of enantiomers in any mixing ratio.

5. A compound according to claim 1, wherein $R^7$ is H, heteroaryl or is a group according to formula II,

II

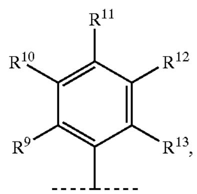

where $R^9$ to $R^{13}$ independently of one another are H, F, Cl, Br, I, $CF_3$, $CHF_2$, $CH_2F$, OH, $OR^{14}$, $OCF_3$, $OCHF_2$, $OCH_2F$, $SR^{14}$, $SO_2CH_3$, $SO_2CF_3$; $C_{1-6}$ alkyl, branched or unbranched, saturated or unsaturated, unsubstituted or singly or multiply substituted; phenyl, unsubstituted or singly or multiply substituted; CN, $COOR^{14}$, $NO_2$, wherein $R^{14}$ is $C_{1-6}$ alkyl, branched or unbranched, saturated or unsaturated, unsubstituted or singly or multiply substituted; or phenyl, benzyl, phenethyl or thiophene, unsubstituted or singly or multiply substituted, or $R^9$ and $R^{10}$, or $R^{10}$ and $R^{11}$ together form an $OCH_2O$ or $OCH_2CH_2O$ ring.

6. A compound according to claim 5, wherein $R^7$ is hydrogen.

7. A compound according to claim 1, wherein $R^1$ and $R^2$ together form a $(CH_2)_{2-5}$ ring, unsubstituted or may optionally be substituted with $C_{1-6}$ alkyl which is branched or unbranched, saturated or unsaturated, unsubstituted or singly or multiply substituted; or an unsubstituted or singly or multiply substituted phenyl, or $R^1$ and $R^2$ independently of one another are $C_{1-3}$ alkyl, unbranched, saturated and unsubstituted.

8. A compound according to claim 7, wherein the $(CH_2)_{2-5}$ ring or phenyl formed by $R^1$ and $R^2$ is unsubstituted.

9. A compound according to claim 8, wherein $R^1$ and $R^2$ together form an unsubstituted $(CH_2)_{2-4}$ ring.

10. A compound according to claim 7, wherein $R^1$ and $R^2$ both denote $CH_3$.

11. A compound according to claim 1, wherein $R^3$ and $R^4$ independently of one another are branched or unbranched, saturated or unsaturated, unsubstituted or singly or multiply substituted $C_{1-6}$ alkyl, or $R^3$ and $R^4$ together form a ring and denote $CH_2CH_2NR^{22}CH_2CH_2$ or $(CH_2)_{3-6}$, wherein $R^{22}$ is H or saturated, branched or unbranched and unsubstituted $C_{1-6}$ alkyl.

12. A compound according to claim 11, wherein both $R^3$ and $R^4$ are $CH_3$.

13. A compound according to claim 11, wherein $R^3$ and $R^4$ form a ring and denote $(CH_2)_{4-5}$ or $CH_2CH_2NR^{22}CH_2CH_2$.

14. A compound according to claim 11, wherein $R^{22}$ is H or $CH_3$.

15. A compound according to claim 1, wherein $R^5$ is $C_{1-6}$ alkyl, saturated or unsaturated, branched or unbranched, singly or multiply substituted or unsubstituted; $C_{5-6}$ cycloalkyl, phenyl, thiophenyl, furyl, benzofuranyl, benzothiophenyl, pyrrolyl, pyridinyl, pyrimidinyl, quinolinyl, isoquinolinyl or quinazolinyl; or phenyl, $C_{5-6}$ cycloalkyl, thiophenyl, furyl, benzofuranyl, benzothiophenyl, pyrrolyl, pyridinyl, pyrimidinyl, quinolinyl, isoquinolinyl, quinazolinyl bound via saturated or unsaturated $C_{1-3}$ alkyl, wherein all aryl, heteroaryl and cycloalkyl independently of one another may be unsubstituted or singly or multiply substituted.

16. A compound according to claim 15, wherein $R^5$ is phenyl, furyl, thiophenyl or $C_{5-6}$ cycloalkyl; or phenyl, furyl, thiophenyl or $C_{5-6}$ cycloalkyl bound via saturated or unsaturated $C_{1-3}$ alkyl.

17. A compound according to claim 15, wherein all aryl, heteroaryl and cycloalkyl independently of one another are unsubstituted, or are singly or multiply substituted by substituents selected independently of one another from the group consisting of F, Cl, Br, I, OH, O—$C_{1-4}$ alkyl, $C_{1-6}$ alkyl, $CF_3$, $CHF_2$, $CH_2F$, $NH_2$ and SH.

18. A compound according to claim 15, wherein $R^5$ is $C_{1-3}$ alkyl, saturated or unsaturated, unsubstituted or unbranched; naphthyl, furyl, cyclohexyl, cyclopentyl, phenyl or thiophenyl, unsubstituted or singly or multiply substituted; or phenyl bound via saturated or unsaturated $C_{1-3}$ alkyl and unsubstituted or singly or multiply substituted.

19. A compound according to claim 18, wherein all aryl, heteroaryl and cycloalkyl independently of one another are unsubstituted, or are singly or multiply substituted by substituents selected independently of one another from the group consisting of F, Cl, Br, I, OH, O—$C_{1-4}$ alkyl, $C_{1-6}$ alkyl, $CF_3$, $CHF_2$, $CH_2F$, $NH_2$ and SH.

20. A compound according to claim 15, wherein $R^5$ is selected from the group consisting of $CH{=}CH_2$, cyclohexyl, cyclopentyl, phenyl, phenethyl (phenyl bound via $CH_2$—$CH_2$), benzyl (phenyl bound via $CH_2$) and thiophenyl.

21. A compound according to claim 20, wherein the phenyl, phenethyl, benzyl and thiophenyl are independent of each other singly or multiply substituted by a substituent selected from the group consisting of F, Cl, Br, I, OH, $OCH_3$, $OC_2H_5$, $OC_3H_7$, SH, $CF_3$, $CHF_2$, $CH_2F$, $CH_3$, $C_2H_5$, $C_3H_7$, $C_4H_9$ and t-butyl.

22. A compound according to claim 1, wherein $R^6$ is phenyl or furyl, unsubstituted or singly or multiply substituted.

23. A compound according to claim 22, wherein $R^6$ is phenyl or fury which is unsubstituted or singly or multiply substituted by substituents selected independently of one another from the group consisting of fluorine, chlorine, $CH_3$, $OCH_3$, $CF_3$ and tert.-butyl.

24. A compound according to claim 1, wherein $R^5$ is aryl, $C_{3-9}$ cycloalkyl or heteroaryl bound via saturated or unsaturated $C_{1-3}$ alkyl, which $C_{1-3}$ alkyl is: —$CH_2$—, —$C_2H_4$—, —$C_3H_6$—, —C≡C—, —CH=CH—, —CH=CH—$CH_2$—, —$CH_2$—CH=CH—, —C≡C—$CH_2$— or —$CH_2$—C≡C—.

25. A compound according to claim 24, wherein $R^5$ is aryl, $C_{3-9}$ cycloalkyl or heteroaryl bound via saturated or unsaturated $C_{1-3}$ alkyl, which $C_{1-3}$ alkyl is: —$CH_2$—, —$C_2H_4$— or —C≡C—.

26. A compound according to claim 1, which is selected from the group consisting of:

2-benzylidene-1-(3-chlorobenzyl)-6-dimethylaminomethyl-cyclohexanol 2-benzylidene-6-dimethylaminomethyl-1-(2,5-dimethyl-benzyl)-cyclohexanol 2-benzylidene-1-(2-chloro-6-fluorobenzyl)-6-dimethylamino-methyl-cyclohexanol 2-benzylidene-1-(4-chlorobenzyl-6-dimethylaminomethyl)-cyclohexanol 2-benzylidene-6-dimethylaminomethyl-1-(3-methylbenzyl)-cyclohexanol 2-benzylidene-6-dimethylaminomethyl-1-(3-trifluoromethyl-phenyl)-cyclohexanol 2-benzylidene-1-(3-chloro-4-fluorophenyl)-6-dimethylamino-methyl-cyclohexanol 2-benzylidene-6-dimethylaminomethyl-1-(2-methylbenzyl)-cyclohexanol 2-benzylidene-6-dimethylaminomethyl-1-(2-methoxyphenyl)-cyclohexanol 2-benzylidene-6-dimethylaminomethyl-1-(3-fluorobenzyl)-cyclohexanol 2-benzylidene-1-(4-chloro-3-trifluoromethylphenyl)-6-dimethylamino-methyl-cyclohexanol 2-benzylidene-6-dimethylaminomethyl-1-(3-methoxybenzyl)-cyclohexanol 2-benzylidene-6-dimethylaminomethyl-1-(4-fluorobenzyl)-cyclohexanol 2-benzylidene-1-(2-chlorobenzyl)-6-dimethylaminomethyl-cyclohexanol 2-benzylidene-1-(3,5-dichlorophenyl)-6-dimethylamino-methyl-cyclohexanol 2-benzylidene-1-(3-chlorophenyl)-6-dimethylaminomethyl-cyclohexanol 2-benzylidene-6-dimethylaminomethyl-1-(3-fluorophenyl)-cyclohexanol 2-benzylidene-6-dimethylaminomethyl-1-(5-fluoro-2-methoxyphenyl)-cyclohexanol 2-benzylidene-1-cyclohexylmethyl-6-dimethylaminomethyl-cyclohexanol 2-benzylidene-6-dimethylaminomethyl-1-(4-methoxyphenyl)-cyclohexanol 2-benzylidene-6-dimethylaminomethyl-1-p-tolyl-cyclohexanol 2-benzylidene-6-dimethylaminomethyl-1-(3-phenylpropyl)-cyclohexanol 2-benzylidene-6-dimethylaminomethyl-1-(3-methoxyphenyl)-cyclohexanol 2-benzylidene-6-dimethylaminomethyl-1-thiophen-2-yl-cyclohexanol 2-benzylidene-6-dimethylaminomethyl-1-phenylethynyl-cyclohexanol 2-benzylidene-6-dimethylaminomethyl-1-phenethyl-cyclohexanol 2-benzylidene-6-dimethylaminomethyl-1-(4-fluorophenyl)-cyclohexanol 2-benzylidene-6-dimethylaminomethyl-bicyclohexyl-1-ol 2-benzylidene-6-dimethylaminomethyl-1-m-tolyl-cyclohexanol 2-benzylidene-1-cyclopentyl-6-dimethylaminomethyl-cyclohexanol 2-benzylidene-1-(4-tert.-butylphenyl)-6-dimethylaminomethyl-cyclohexanol 2-benzylidene-6-dimethylaminomethyl-1-vinyl-cyclohexanol 2-benzylidene-6-dimethylaminomethyl-1-o-tolyl-cyclohexanol 2-benzylidene-6-dimethylaminomethyl-1-(4-fluoro-3-methylphenyl)-cyclohexanol 1-benzyl-2-benzylidene-6-dimethylaminomethyl-cyclohexanol 2-benzylidene-1-(4-chlorophenyl)-6-dimethylaminomethyl-cyclohexanol 2-benzylidene-6-dimethylaminomethyl-1-phenyl-cyclohexanol 1-(3-chlorobenzyl)-2-(4-chlorobenzylidene)-6-dimethyl-aminomethyl-cyclohexanol 2-(4-chlorobenzylidene)-6-dimethylaminomethyl-1-(2,5-dimethylbenzyl)-cyclohexanol 2-(4-chlorobenzylidene)-1-(2-chloro-6-fluorobenzyl)-6-dimethylaminomethyl-cyclohexanol 1-(4-chlorobenzyl)-2-(4-chlorobenzylidene)-6-dimethyl-aminomethyl-cyclohexanol 2-(4-chlorobenzylidene)-6-dimethylaminomethyl-1-(3-trifluoromethylphenyl)-cyclohexanol 2-(4-chlorobenzylidene)-1-(3-chloro-4-fluorophenyl)-6-dimethylamino-methyl-cyclohexanol 2-(4-chlorobenzylidene)-6-dimethylaminomethyl-1-(2-methylbenzyl)-cyclohexanol 2-(4-chlorobenzylidene)-6-dimethylaminomethyl-1-(2-methoxyphenyl)-cyclohexanol 2-(4-chlorobenzylidene)-6-dimethylaminomethyl-1-(3-fluorobenzyl)-cyclohexanol 2-(4-chlorobenzylidene)-1-(4-chloro-3-trifluoromethyl-phenyl)-6-dimethylaminomethyl-cyclohexanol 2-(4-chlorobenzylidene)-6-dimethylaminomethyl-1-(3-methoxybenzyl)-cyclohexanol 2-(4-chlorobenzylidene)-6-dimethylaminomethyl-1-(4-fluorobenzyl)-cyclohexanol 1-(2-chlorobenzyl)-2-(4-chlorobenzylidene)-6-dimethyl-aminomethyl-cyclohexanol 2-(4-chlorobenzylidene)-1-(3,5-dichlorophenyl)-6-dimethylaminomethyl-cyclohexanol 2-(4-chlorobenzylidene)-1-(3-chlorophenyl)-6-dimethyl-aminomethyl-cyclohexanol 2-(4-chlorobenzylidene)-6-dimethylaminomethyl-1-(3-fluorophenyl)-cyclohexanol 2-(4-chlorobenzylidene)-6-dimethylaminomethyl-1-(5-fluoro-2-methoxy-phenyl)-cyclohexanol 2-(4-chlorobenzylidene)-1-cyclohexylmethyl-6-dimethyl-aminomethyl-cyclohexanol 2-(4-chlorobenzylidene)-6-dimethylaminomethyl-1-(4-methoxyphenyl)-cyclohexanol 2-(4-chlorobenzylidene)-6-dimethylaminomethyl-1-p-tolyl-cyclohexanol 2-(4-chlorobenzylidene)-6-dimethylaminomethyl-1-(3-phenylpropyl)-cyclohexanol 2-(4-chlorobenzylidene)-6-dimethylaminomethyl-1-(3-methoxyphenyl)-cyclohexanol 2-(4-chlorobenzylidene)-6-dimethylaminomethyl-1-thiophen-2-yl-cyclohexanol 2-(4-chlorobenzylidene)-6-dimethylaminomethyl-1-phenyl-ethynyl-cyclohexanol 2-(4-chlorobenzylidene)-6-dimethylaminomethyl-1-phenethyl-cyclohexanol 2-(4-chlorobenzylidene)-6-dimethylaminomethyl-1-(4-fluorophenyl)-cyclohexanol 2-(4-chlorobenzylidene)-6-dimethylaminomethyl-bicylcohexyl-1-ol 2-(4-chlorobenzylidene)-6-dimethylaminomethyl-1-m-tolyl-cyclohexanol 2-(4-chlorobenzylidene)-1-cyclopentyl-6-dimethylamino-methyl-cyclohexanol 1-(4-tert.-butylphenyl)-2-(4-chlorobenzylidene-6-dimethyl-aminomethyl-cyclohexanol 2-(4-chlorobenzylidene)-6-dimethylaminomethyl-1-vinyl-cyclohexanol 2-(4-chlorobenzylidene)-6-dimethylaminomethyl-1-o-tolyl-cyclohexanol 2-(4-chlorobenzylidene)-6-dimethylaminomethyl-1-(4-fluoro-3-methylphenyl)-cyclohexanol 1-benzyl-2-(4-chlorobenzylidene)-6-dimethylaminomethyl-cyclohexanol 2-(4-chlorobenzylidene)-1-(4-chlorophenyl)-6-dimethyl-aminomethyl-cyclohexanol 2-(4-chlorobenzylidene)-6-dimethylaminomethyl-1-phenyl-cyclohexanol 1-(3-chlorobenzyl)-2-dimethylaminomethyl-6-(4-methoxy-benzylidene)-cyclohexanol 2-dimethylaminomethyl-1-(2,5-dimethylbenzyl)-6-(4-methoxybenzylidene)-cyclohexanol 1-(2-chloro-6-fluorobenzyl)-2-dimethylaminomethyl-6-(4-methoxybenzyl-idene)-cyclohexanol 2-dimethylaminomethyl-6-(4-methoxybenzylidene)-1-(3-methylbenzyl)-cyclohexanol 2-dimethylaminomethyl-6-(4-methoxybenzylidene)-1-(3-trifluoromethylphenyl)-cyclohexanol 1-(3-chloro-4-fluorophenyl)-2-dimethylaminomethyl-6-(4-methoxybenzyl-idene)-cyclohexanol 2-dimethylaminomethyl-6-(4-methoxybenzylidene)-1-(2-methoxyphenyl)-cyclohexanol 1-(4-chloro-3-trifluoromethylphenyl)-2-dimethylamino-methyl-6-(4-methoxybenzylidene)-cyclohexanol 2-dimethylaminomethyl-1-(4-fluorobenzyl)-6-(4-methoxy-benzylidene)-cyclohexanol 1-(2-chlorobenzyl)-2-dimethylaminomethyl-6-(4-methoxy-benzylidene)-cyclohexanol 1-(3,5-dichlorophenyl)-2-dimethylaminomethyl-6-(4-methoxybenzylidene)-cyclohexanol 1-(3-chlorophenyl)-2-dimethylaminomethyl-6-(4-methoxy-benzylidene)-cyclohexanol 2-dimethylaminomethyl-1-(5-fluoro-2-methoxyphenyl)-6-(4-methoxybenzyl-idene)-cyclohexanol 1-cyclohexylmethyl-2-dimethylaminomethyl-6-(4-methoxy-benzylidene)-cyclohexanol 2-dimethylaminomethyl-6-(4-methoxybenzylidene)-1-(4-methoxyphenyl)-cyclohexanol 2-dimethylaminomethyl-6-(4-methoxybenzylidene)-1-p-tolyl-cyclohexanol 1-(2,3-dichlorophenyl)-2-dimethylaminomethyl-6-(4-methoxybenzylidene)-cyclohexanol 2-dimethylaminomethyl-6-(4-methoxybenzylidene)-1-(3-phenylpropyl)-cyclohexanol 2-dimethylaminomethyl-6-(4-methoxybenzylidene)-1-(3-methoxyphenyl)-cyclohexanol 2-dimethylaminomethyl-6-(4-methoxybenzylidene)-1-thiophen-2-yl-cyclohexanol 2-dimethylaminomethyl-6-(4-methoxybenzylidene)-1-phenylethynyl-cyclohexanol 2-dimethylaminomethyl-6-(4-methoxybenzylidene)-1-phenethyl-cyclohexanol 2-dimethylaminomethyl-1-(4-fluorophenyl)-6-(4-methoxy-benzylidene)-cyclohexanol 6-dimethylaminomethyl-2-(4-methoxybenzylidene)-bicyclohexyl-1-ol 2-dimethylaminomethyl-6-(4-methoxybenzylidene)-1-m-tolyl-cyclohexanol 1-cyclopentyl-2-dimethylaminomethyl-6-(4-methoxy-benzylidene)-cyclohexanol 1-(4-tert.-butylphenyl)-2-dimethylaminomethyl-6-(4-methoxybenzylidene)-cyclohexanol 2-dimethylaminomethyl-6-(4-methoxybenzylidene)-1-vinyl-cyclohexanol 2-dimethylaminomethyl-6-(4-methoxybenzylidene)-1-o-tolyl-cyclohexanol 2-dimethylaminomethyl-1-(4-fluoro-3-methylphenyl)-6-(4-methoxy-benzylidene)-cyclohexanol 1-benzyl-2-dimethylaminomethyl-6-(4-methoxybenzylidene)-cyclohexanol 1-(4-chlorophenyl)-2-dimethylaminomethyl-6-(4-methoxy-benzylidene)-cyclohexanol 2-dimethylaminomethyl-6-(4-methoxybenzylidene)-1-phenyl-cyclohexanol 1-(3-chlorobenzyl)-2-dimethylaminomethyl-6-(3-methoxy-benzylidene)-cyclohexanol 2-dimethylaminomethyl-1-(2,5-dimethylbenzyl)-6-(3-methoxybenzylidene)-cyclohexanol 2-dimethylaminomethyl-6-(3-methoxybenzylidene)-1-(2-methylbenzyl)-cyclohexanol 2-dimethylaminomethyl-6-(3-methoxybenzylidene)-1-(2-methoxyphenyl)-cyclohexanol 1-(4-chloro-3-trifluoromethylphenyl)-2-dimethylamino-methyl-6-(3-methoxybenzylidene)-cyclohexanol 1-(2-chlorobenzyl)-2-dimethylaminomethyl-6-(3-methoxybenzylidene)-cyclohexanol 6-dimethylaminomethyl-2-(3-methoxybenzylidene)-bicyclohexyl-1-ol 1-cyclopentyl-2-dimethylaminomethyl-6-(3-methoxybenzylidene)-cyclohexanol 2-dimethylaminomethyl-6-(3-methoxybenzylidene)-1-vinyl-cyclohexanol 2-dimethylaminomethyl-1-(4-fluoro-3-methylphenyl)-6-(3-methoxy-benzylidene)-cyclohexanol 1-benzyl-2-dimethylaminomethyl-6-(3-methoxybenzylidene)-cyclohexanol 2-dimethylaminomethyl-6-(3-methoxybenzylidene)-1-phenyl-cyclohexanol 1-benzyl-2-(2-chlorobenzylidene)-6-dimethylaminomethyl-cyclohexanol 5-dimethylaminomethyl-2,4-dimethyl-1,3-diphenyl-pent-1-en-3-ol 3-(4-chlorophenyl)-5-dimethylamino-2,4-dimethyl-1-phenyl-pent-1-en-3-ol 3-benzyl-5-dimethylamino-2,4-dimethyl-1-phenyl-pent-1-en-3-ol 5-dimethylamino-3-(4-fluoro-3-methylphenyl)-2,4-dimethyl-1-phenyl-pent-1-en-3-ol 5-dimethylamino-2,4-dimethyl-1-phenyl-3-o-tolyl-pent-1-en-3-ol 3-(2-dimethylamino-1-methylethyl)-2-methyl-1-phenylpenta-1,4-dien-3-ol 3-(4-tert.-butylphenyl)-5-dimethylamino-2,4-dimethyl-1-phenyl-pent-1-en-3-ol 3-cyclopentyl-5-dimethylamino-2,4-dimethyl-1-phenyl-pent-1-en-3-ol 5-dimethylamino-2,4-dimethyl-1-phenyl-3-m-tolyl-pent-1-en-3-ol 3-cyclohexyl-5-dimethylamino-2,4-dimethyl-1-phenyl-pent-1-en-3-ol 5-dimethylamino-3-(4-fluorophenyl)-2,4-dimethyl-1-phenyl-pent-1-en-3-ol 5-dimethylamino-2,4-dimethyl-3-phenethyl-1-phenyl-pent-1-en-3-ol 3-(2-dimethylamino-1-methylethyl)-2-methyl-1,5-diphenyl-pent-1-en-4-yn-3-ol 5-dimethylamino-2,4-dimethyl-1-phenyl-3-thiophen-2-yl-pent-1-en-3-ol 3-(2,4-dichlorophenyl)-5-dimethylamino-2,4-dimethyl-1-phenyl-pent-1-en-3-ol 5-dimethylamino-3-(3-methoxyphenyl)-2,4-dimethyl-1-phenyl-pent-1-en-3-ol 3-(2-dimethylamino-1-methylethyl)-2-methyl-1,6-diphenylhex-1-en-3-ol 3-(2,3-dichlorophenyl)-5-dimethylamino-2,4-dimethyl-1-phenyl-pent-1-en-3-ol 5-dimethylamino-2,4-dimethyl-1-phenyl-3-p-tolyl-pent-1-en-3-ol 5-dimethylamino-3-(4-methoxyphenyl)-2,4-dimethyl-1-phenyl-pent-1-en-3-ol 3-cyclohexylmethyl-5-dimethylamino-2,4-dimethyl-1-phenyl-pent-1-en-3-ol 5-dimethylamino-3-(5-fluoro-2-methoxyphenyl)-2,4-dimethyl-1-phenyl-pent-1-en-3-ol 5-dimethylamino-3-(3-fluorophenyl)-2,4-dimethyl-1-phenyl-pent-1-en-3-ol 3-(3-chlorophenyl)-5-dimethylamino-2,4-dimethyl-1-phenyl-pent-1-en-3-ol 3-(3,5-chlorophenyl)-5-dimethylamino-2,4-dimethyl-1-phenyl-pent-1-en-3-ol 3-(2-chlorobenzyl)-5-dimethylamino-2,4-dimethyl-1-phenyl-pent-1-en-3-ol 5-dimethylamino-3-(4-fluorobenzyl)-2,4-dimethyl-1-phenyl-pent-1-en-3-ol 3-(4-chloro-3-trifluoromethylphenyl)-5-dimethylamino-2,4-dimethyl-1-phenyl-pent-1-en-3-ol 5-dimethylamino-3-(2-methoxyphenyl)-2,4-dimethyl-1-phenyl-pent-1-en-3-ol 5-dimethylamino-2,4-dimethyl-3-(2-methylbenzyl)-1-phenyl-pent-1-en-3-ol 3-(3-chloro-4-fluorophenyl)-5-dimethylamino-2,4-dimethyl-1-phenyl-pent-1-en-3-ol 5-dimethylamino-2,4-dimethyl-1-phenyl-3-(3-trifluoromethylphenyl)-pent-1-en-3-ol 5-dimethylamino-2,4-dimethyl-3-(3-methylbenzyl)-1-phenyl-pent-1-en-3-ol 3-(4-chlorobenzyl)-5-dimethylamino-2,4-dimethyl-1-phenyl-pent-1-en-3-ol 3-(2-chloro-6-fluorobenzyl)-5-dimethylamino-2,4-dimethyl-1-phenyl-pent-1-en-3-ol 5-dimethylamino-3-(2,5-dimethylbenzyl)-2,4-dimethyl-1-phenyl-pent-1-en-3-ol 3-(3-chlorobenzyl)-5-dimethylamino-2,4-dimethyl-1-phenyl-pent-1-en-3-ol 3-(2,4-dichlorobenzyl)-5-dimethylamino-2,4-dimethyl-1-phenyl-pent-1-en-3-ol 5-dimethylamino-1-(4-fluorophenyl)-2,4-dimethyl-3-phenyl-pent-1-en-3-ol 3-benzyl-5-dimethylamino-1-(4-fluorophenyl)-2,4-dimethyl-pent-1-en-3-ol 5-dimethylamino-3-(4-fluoro-3-methylphenyl)-1-(4-fluoro-phenyl)-2,4-dimethyl-pent-1-en-3-ol 5-dimethylamino-1-(4-fluorophenyl)-2,4-dimethyl-3-o-tolyl-pent-1-en-3-ol 3-(2-dimethylamino-1-methylethyl)-1-(4-fluorophenyl)-2-methyl-pent-1,4-dien-3-ol 3-(4-tert.-butylphenyl)-5-dimethylamino-1-(4-fluorophenyl)-2,4-dimethyl-pent-1-en-3-ol 3-cyclopentyl-5-dimethylamino-1-(4-fluorophenyl)-2,4-dimethyl-pent-1-en-3-ol 5-dimethylamino-1-(4-fluorophenyl)-2,4-dimethyl-3-m-tolyl-pent-1-en-3-ol 3-cyclohexyl-5-dimethylamino-1-(4-fluorophenyl)-2,4-dimethyl-pent-1-en-3-ol 5-dimethylamino-1,3-bis-(4-fluorophenyl)-2,4-dimethyl-pent-1-en-3-ol 5-dimethylamino-1-(4-fluorophenyl)-2,4-dimethyl-3-phenethyl-pent-1-en-3-ol 3-(2-dimethylamino-1-methylethyl)-1-(4-fluorophenyl)-2-methyl-5-phenyl-pent-1-en-4-yn-3-ol 5-dimethylamino-1-(4-fluorophenyl)-2,4-dimethyl-3-thiophen-2-yl-pent-1-en-3-ol 3-(2,4-dichlorophenyl)-5-dimethylamino-1-(4-fluorophenyl)-2,4-dimethyl-pent-1-en-3-ol 5-dimethylamino-1-(4-fluorophenyl)-3-(3-methoxyphenyl)-2,4-dimethyl-pent-1-en-3-ol 3-(2-dimethylamino-1-methylethyl)-1-(4-fluorophenyl)-2-methyl-6-phenyl-hex-1-en-3-ol 3-(2,3-dichlorophenyl)-5-dimethylamino-1-(4-fluorophenyl)-2,4-dimethyl-pent-1-en-3-ol 5-dimethylamino-1-(4-fluorophenyl)-2,4-dimethyl-3-p-tolyl-pent-1-en-3-ol 5-dimethylamino-1-(4-fluorophenyl)-3-(4-methoxyphenyl)-2,4-dimethyl-pent-1-en-3-ol 3-cyclohexylmethyl-5-dimethylamino-1-(4-fluorophenyl)-2,4-dimethyl-pent-1-en-3-ol 5-dimethylamino-3-(5-fluoro-2-methoxyphenyl)-1-(4-fluorophenyl)-2,4-dimethyl-pent-1-en-3-ol 5-dimethylamino-3-(3-fluorophenyl)-1-(4-fluorophenyl)-2,4-dimethyl-pent-1-en-3-ol 3-(3-chlorophenyl)-5-dimethylamino-1-(4-fluorophenyl)-2,4-dimethyl-pent-1-en-3-ol 3-(3,5-dichlorophenyl)-5-dimethylamino-1-(4-fluorophenyl)-2,4-dimethyl-pent-1-en-3-ol 3-(2-chlorobenzyl)-5-dimethylamino-1-(4-fluorophenyl)-2,4-dimethyl-pent-1-en-3-ol 5-dimethylamino-3-(4-fluorobenzyl)-1-(4-fluorophenyl)-2,4-dimethyl-pent-1-en-3-ol 5-dimethylamino-1-(4-fluorophenyl)-3-(3-methoxybenzyl)-2,4-dimethyl-pent-1-en-3-ol 3-(4-chloro-3-trifluoromethylphenyl)-5-dimethylamino-1-(4-fluorophenyl)-2,4-dimethyl-pent-1-en-3-ol 5-dimethylamino-3-(3-fluorobenzyl)-1-(4-fluorophenyl)-2,4-dimethyl-pent-1-en-3-ol 5-dimethylamino-1-(4-fluorophenyl)-3-(2-methoxyphenyl)-2,4-dimethyl-pent-1-en-3-ol 5-dimethylamino-1-(4-fluorophenyl)-2,4-dimethyl-3-(2-methylbenzyl)-pent-1-en-3-ol 3-(3-chloro-4-fluorophenyl)-5-dimethylamino-1-(4-fluorophenyl)-2,4-dimethyl-pent-1-en-3-ol 5-dimethylamino-1-(4-fluorophenyl)-2,4-dimethyl-3-(3-trifluoromethylphenyl)-pent-1-en-3-ol 5-dimethylamino-1-(4-fluorophenyl)-2,4-dimethyl-3-(3-methylbenzyl)-pent-1-en-3-ol 3-(4-chlorobenzyl)-5-dimethylamino-1-(4-fluorophenyl)-2,4-dimethyl-pent-1-en-3-ol 3-(2-chloro-6-fluorobenzyl)-5-dimethylamino-1-(4-fluoro-phenyl)-2,4-dimethyl-pent-1-en-3-ol 5-dimethylamino-3-(2,5-dimethylbenzyl)-1-(4-fluorophenyl)-2,4-dimethyl-pent-1-en-3-ol 3-(3-chlorobenzyl)-5-dimethylamino-1-(4-fluorophenyl)-2,4-dimethyl-pent-1-en-3-ol 3-(2,4-dichlorobenzyl)-5-dimethylamino-1-(4-fluorophenyl)-2,4-dimethyl-pent-1-en-3-ol 1-(4-chlorophenyl)-5-dimethylamino-2,4-dimethyl-3-phenyl-pent-1-en-3-ol 1,3-bis-(4-chlorophenyl)-5-dimethylamino-2,4-dimethyl-pent-1-en-3-ol 3-benzyl-1-(4-chlorophenyl)-5-dimethylamino-2,4-dimethyl-pent-1-en-3-ol 1-(4-chlorophenyl)-5-dimethylamino-3-(4-fluoro-3-methyl-phenyl)-2,4-dimethyl-pent-1-en-3-ol 1-(4-chlorophenyl)-5-dimethylamino-2,4-dimethyl-3-o-tolyl-pent-1-en-3-ol 1-(4-chlorophenyl)-3-(2-dimethylamino-1-methylethyl)-2-methyl-penta-1,4-dien-3-ol 3-(4-tert.-butylphenyl)-1-(4-chlorophenyl)-5-dimethylamino-2,4-dimethyl-pent-1-en-3-ol 1-(4-chlorophenyl)-3-cyclopentyl-5-dimethylamino-2,4-dimethyl-pent-1-en-3-ol 1-(4-chlorophenyl)-5-dimethylamino-2,4-dimethyl-3-m-tolyl-pent-1-en-3-ol 1-(4-chlorophenyl)-3-cyclohexyl-5-dimethylamino-2,4-dimethyl-pent-1-en-3-ol 1-(4-chlorophenyl)-5-dimethylamino-3-(4-fluorophenyl)-2,4-dimethyl-pent-1-en-3-ol 1-(4-chlorophenyl)-5-dimethylamino-2,4-dimethyl-3-phenethyl-pent-1-en-3-ol 1-(4-chlorophenyl)-5-dimethylamino-2,4-dimethyl-3-thiophen-2-yl-pent-1-en-3-ol 1-(4-chlorophenyl)-3-(2,4-dichlorophenyl)-5-dimethylamino-2,4-dimethyl-pent-1-en-3-ol 1-(4-chlorophenyl)-5-dimethylamino-3-(3-methoxyphenyl)-2,4-dimethyl-pent-1-en-3-ol 1-(4-chlorophenyl)-3-(2-dimethylamino-1-methylethyl)-2-methyl-6-phenyl-hex-1-en-3-ol 1-(4-chlorophenyl)-3-(2,3-dichlorophenyl)-5-dimethylamino-2,4-dimethyl-pent-1-en-3-ol 1-(4-chlorophenyl)-5-dimethylamino-2,4-dimethyl-3-p-tolyl-pent-1-en-3-ol 1-(4-chlorophenyl)-5-dimethylamino-3-(4-methoxyphenyl)-2,4-dimethyl-pent-1-en-3-ol 1-(4-chlorophenyl)-3-cyclohexylmethyl-5-dimethylamino-2,4-dimethyl-pent-1-en-3-ol 1-(4-chlorophenyl)-5-dimethylamino-3-(5-fluoro-2-methoxyphenyl)-2,4-dimethyl-pent-1-en-3-ol 1-(4-chlorophenyl)-5-dimethylamino-3-(3-fluorophenyl)-2,4-dimethyl-pent-1-en-3-ol 3-(3-chlorophenyl)-1-(4-chlorophenyl)-5-dimethylamino-2,4-dimethyl-pent-1-en-3-ol 1-(4-chlorophenyl)-3-(3,5-dichlorophenyl)-5-dimethylamino-2,4-dimethyl-pent-1-en-3-ol 3-(2-chlorobenzyl)-1-(4-chlorophenyl)-5-dimethylamino-2,4-dimethyl-pent-1-en-3-ol 1-(4-chlorophenyl)-5-dimethylamino-3-(4-fluorobenzyl)-2,4-dimethyl-pent-1-en-3-ol 1-(4-chlorophenyl)-5-dimethylamino-3-(3-methoxybenzyl)-2,4-dimethyl-pent-1-en-3-ol 1-(4-chlorophenyl)-3-(4-chloro-3-trifluoromethylphenyl)-5-dimethylamino-2,4-dimethyl-pent-1-en-3-ol 1-(4-chlorophenyl)-5-dimethylamino-3-[2-(3-fluorophenyl)-ethyl]-2,4-dimethyl-pent-1-en-3-ol 1-(4-chlorophenyl)-5-dimethylamino-3-(2-methoxyphenyl)-2,4-dimethyl-pent-1-en-3-ol 1-(4-chlorophenyl)-5-dimethylamino-2,4-dimethyl-3-(2-methylbenzyl)-pent-1-en-3-ol 3-(3-chloro-4-fluorophenyl)-1-(4-chlorophenyl)-5-dimethyl-amino-2,4-dimethyl-pent-1-en-3-ol 1-(4-chlorophenyl)-5-dimethylamino-2,4-dimethyl-3-(3-trifluoromethylphenyl)-pent-1-en-3-ol 1-(4-chlorophenyl)-5-dimethylamino-2,4-dimethyl-3-(3-methylbenzyl)-pent-1-en-3-ol 3-(4-chlorobenzyl)-1-(4-chlorophenyl)-5-dimethylamino-2,4-dimethyl-pent-1-en-3-ol 3-(2-chloro-6-fluorobenzyl)-1-(4-chlorophenyl)-5-dimethyl-amino-2,4-dimethyl-pent-1-en-3-ol 1-(4-chlorophenyl)-5-dimethylamino-3-(2,5-dimethylbenzyl)-2,4-dimethyl-pent-1-en-3-ol 3-(3-chlorobenzyl)-1-(4-chlorophenyl)-5-dimethylamino-2,4-dimethyl-pent-1-en-3-ol 1-(4-chlorophenyl)-3-(2,4-dichlorobenzyl)-5-dimethylamino-2,4-dimethyl-pent-1-en-3-ol 5-dimethylamino-1-(4-methoxyphenyl)-2,4-dimethyl-3-phenyl-pent-1-en-3-ol 3-(4-chlorophenyl)-5-dimethylamino-1-(4-methoxyphenyl)-2,4-dimethyl-pent-1-en-3-ol 3-benzyl-5-dimethylamino-1-(4-methoxyphenyl)-2,4-dimethyl-pent-1-en-3-ol 5-dimethylamino-3-(4-fluoro-3-methylphenyl)-1-(4-methoxyphenyl)-2,4-dimethyl-pent-1-en-3-ol 5-dimethylamino-1-(4-methoxyphenyl)-2,4-dimethyl-3-o-tolyl-pent-1-en-3-ol 3-(2-dimethylamino-1-methylethyl)-1-(4-methoxyphenyl)-2-methyl-penta-1,4-dien-3-ol 3-(4-tert.-butylphenyl)-5-dimethylamino-1-(4-methoxy-phenyl)-2,4-dimethyl-pent-1-en-3-ol 3-cyclopentyl-5-dimethylamino-1-(4-methoxyphenyl)-2,4-dimethyl-pent-1-en-3-ol 5-dimethylamino-1-(4-methoxyphenyl)-2,4-dimethyl-3-m-tolyl-pent-1-en-3-ol 3-cyclohexyl-5-dimethylamino-1-(4-methoxyphenyl)-2,4-dimethyl-pent-1-en-3-ol 5-dimethylamino-3-(4-fluorophenyl)-1-(4-methoxyphenyl)-2,4-dimethyl-pent-1-en-3-ol 5-dimethylamino-1-(4-methoxyphenyl)-2,4-dimethyl-3-phenethyl-pent-1-en-3-ol 3-(2-dimethylamino-1-methylethyl)-1-(4-methoxyphenyl)-2-methyl-5-phenyl-pent-1-en-4-yn-3-ol 5-dimethylamino-1-(4-methoxyphenyl)-2,4-dimethyl-3-thiophen-2-yl-pent-1-en-3-ol 3-(2,4-dichlorophenyl)-5-dimethylamino-1-(4-methoxy-phenyl)-2,4-dimethyl-pent-1-en-3-ol 5-dimethylamino-3-(3-methoxyphenyl)-1-(4-methoxyphenyl)-2,4-dimethyl-pent-1-en-3-ol 3-(2-dimethylamino-1-methylethyl)-1-(4-methoxyphenyl)-2-methyl-6-phenyl-hex-1-en-3-ol 3-(2,3-dichlorophenyl)-5-dimethylamino-1-(4-methoxy-phenyl)-2,4-dimethyl-pent-1-en-3-ol 5-dimethylamino-1-(4-methoxyphenyl)-2,4-dimethyl-3-p-tolyl-pent-1-en-3-ol 5-dimethylamino-1,3-bis-(4-methoxyphenyl)-2,4-dimethyl-pent-1-en-3-ol 3-cyclohexylmethyl-5-dimethylamino-1-(4-methoxyphenyl)-2,4-dimethyl-pent-1-en-3-ol 5-dimethylamino-3-(5-fluoro-2-methoxyphenyl)-1-(4-methoxyphenyl)-2,4-dimethyl-pent-1-en-3-ol 5-dimethylamino-3-(3-fluorophenyl)-1-(4-methoxyphenyl)-2,4-dimethyl-pent-1-en-3-ol 3-(3-chlorophenyl)-5-dimethylamino-1-(4-methoxyphenyl)-2,4-dimethyl-pent-1-en-3-ol 3-(3,5-dichlorophenyl)-5-dimethylamino-1-(4-methoxyphenyl)-2,4-dimethyl-pent-1-en-3-ol 3-(2-chlorobenzyl)-5-dimethylamino-1-(4-methoxyphenyl)-2,4-dimethyl-pent-1-en-3-ol 5-dimethylamino-3-(4-fluorobenzyl)-1-(4-methoxyphenyl)-2,4-dimethyl-pent-1-en-3-ol 5-dimethylamino-3-(3-fluorobenzyl)-1-(4-methoxyphenyl)-2,4-dimethyl-pent-1-en-3-ol 5-dimethylamino-3-(2-methoxyphenyl)-1-(4-methoxyphenyl)-2,4-dimethyl-pent-1-en-3-ol 5-dimethylamino-1-(4-methoxyphenyl)-2,4-dimethyl-3-(2-methylbenzyl)-pent-1-en-3-ol 3-(3-chloro-4-fluorophenyl)-5-dimethylamino-1-(4-methoxy-phenyl)-2,4-dimethyl-pent-1-en-3-ol 5-dimethylamino-1-(4-methoxyphenyl)-2,4-dimethyl-3-(3-trifluoromethylphenyl)-pent-1-en-3-ol 3-(4-chlorobenzyl)-5-dimethylamino-1-(4-methoxyphenyl)-2,4-dimethyl-pent-1-en-3-ol 3-(2-chloro-6-fluorobenzyl)-5-dimethylamino-1-(4-methoxy-phenyl)-2,4-dimethyl-pent-1-en-3-ol 3-(3-chlorobenzyl)-5-dimethylamino-1-(4-methoxyphenyl)-2,4-dimethyl-pent-1-en-3-ol 2-benzylidene-1-(4-tert.-butylphenyl)-5-dimethylaminomethyl-cyclopentanol 2-benzylidene-1-cyclohexyl-5-dimethylaminomethyl-cyclopentanol 2-benzylidene-5-dimethylaminomethyl-1-phenethyl-cyclopentanol 2-benzylidene-5-dimethylaminomethyl-1-(4-fluorobenzyl)-cyclopentanol 2-benzylidene-5-dimethylaminomethyl-1-(3-fluorobenzyl)-cyclopentanol 2-benzylidene-5-dimethylaminomethyl-1-(2-methoxyphenyl)-cyclopentanol 2-benzylidene-5-dimethylaminomethyl-1-(2-methylbenzyl)-cyclopentanol 2-benzylidene-5-dimethylaminomethyl-1-(3-methylbenzyl)-cyclopentanol 2-benzylidene-1-(4-chlorobenzyl)-5-dimethylaminomethyl-cyclopentanol 2-benzylidene-1-(2-chloro-6-fluorobenzyl)-5-dimethylamino-methyl-cyclopentanol 2-benzylidene-5-dimethylaminomethyl-1-(2,5-dimethyl-benzyl)-cyclopentanol 2-benzylidene-1-(3-chlorobenzyl)-5-dimethylaminomethyl-cyclopentanol 2-dimethylaminomethyl-5-(3-methoxybenzyl)-bicyclopentyl-1-ol 2-dimethylaminomethyl-5-(3-methoxybenzyl)-1-m-tolyl-cyclopentanol 1-cyclohexyl-2-dimethylaminomethyl-5-(3-methoxybenzyl)-cyclopentanol 2-dimethylaminomethyl-5-(3-methoxybenzyl)-1-phenethyl-cyclopentanol 2-dimethylaminomethyl-5-(3-methoxybenzyl)-1-phenyl-ethynyl-cyclopentanol 2-dimethylaminomethyl-5-(3-methoxybenzyl)-1-thiophen-2-yl-cyclopentanol 2-dimethylaminomethyl-5-(3-methoxybenzyl)-1-(3-methoxy-phenyl)-cyclopentanol 2-dimethylaminomethyl-5-(3-methoxybenzyl)-1-(3-phenyl-propyl)-cyclopentanol 2-dimethylaminomethyl-5-(3-methoxybenzyl)-1-(4-methoxy-phenyl)-cyclopentanol 2-dimethylaminomethyl-1-(3-fluorobenzyl)-5-(3-methoxy-benzylidene)-cyclopentanol 2-dimethylaminomethyl-5-(3-methoxybenzylidene)-1-(2-methoxyphenyl)-cyclopentanol 2-dimethylaminomethyl-5-(3-methoxybenzylidene)-1-(2-methylbenzyl)-cyclopentanol 2-dimethylaminomethyl-5-(3-methoxybenzylidene)-1-(3-methylbenzyl)-cyclopentanol 2-dimethylaminomethyl-1-(2,5-dimethylbenzyl)-5-(3-methoxybenzylidene)-cyclopentanol 1-(3-chlorobenzyl)-2-dimethylaminomethyl-5-(3-methoxybenzylidene)-cyclopentanol 1-benzyl-2-dimethylaminomethyl-5-(3-methoxybenzylidene)-cyclopentanol 2-dimethylaminomethyl-5-(3-methoxybenzylidene)-1-o-tolyl-cyclopentanol 2-dimethylaminomethyl-5-(3-methoxybenzylidene)-1-vinyl-cyclopentanol 1-(4-tert.-butylphenyl)-2-dimethylaminomethyl-5-(3-methoxybenzylidene)-cyclopentanol 2-dimethylaminomethyl-5-(3-methoxybenzylidene)-bicyclopentyl-1-ol 1-cyclohexyl-2-dimethylaminomethyl-5-(3-methoxy-benzylidene)-cyclopentanol 2-dimethylaminomethyl-1-(4-fluorophenyl)-5-(3-methoxy-benzylidene)-cyclopentanol 2-dimethylaminomethyl-5-(3-methoxybenzylidene)-1-phenethyl-cyclopentanol 2-dimethylaminomethyl-5-(3-methoxybenzylidene)-1-phenylethynyl-cyclopentanol 2-dimethylaminomethyl-5-(3-methoxybenzylidene)-1-thiophen-2-yl-cyclopentanol 2-dimethylaminomethyl-5-(3-methoxybenzylidene)-1-(3-methoxyphenyl)-cyclopentanol 2-dimethylaminomethyl-5-(3-methoxybenzylidene)-1-(3-phenylpropyl)-cyclopentanol 2-dimethylaminomethyl-5-(3-methoxybenzylidene)-1-p-tolyl-cyclopentanol 2-dimethylaminomethyl-5-(3-methoxybenzylidene)-1-(4-methoxyphenyl)-cyclopentanol 1-(2-chlorobenzyl)-2-dimethylaminomethyl-5-(4-methoxy-benzylidene)-cyclopentanol 2-dimethylaminomethyl-1-(3-methoxybenzyl)-5-(4-methoxy-benzylidene)-cyclopentanol 2-dimethylaminomethyl-1-(3-fluorobenzyl)-5-(4-methoxy-benzylidene)-cyclopentanol 2-dimethylaminomethyl-5-(4-methoxybenzylidene)-1-(2-methoxyphenyl)-cyclopentanol 2-dimethylaminomethyl-5-(4-methoxybenzylidene)-1-(3-methylbenzyl)-cyclopentanol 1-(4-chlorobenzyl)-2-dimethylaminomethyl-5-(4-methoxy-benzylidene)-cyclopentanol 1-(2-chloro-6-fluorobenzyl)-2-dimethylaminomethyl-5-(4-methoxy-benzylidene)-cyclopentanol 1-(3-chlorobenzyl)-2-dimethylaminomethyl-5-(4-methoxy-benzylidene)-cyclopentanol 1-(2,4-dichlorobenzyl)-2-dimethylaminomethyl-5-(4-methoxybenzylidene)-cyclopentanol 2-benzylidene-7-dimethylaminomethyl-1-phenyl-cycloheptanol 2-benzylidene-1-(4-chlorophenyl)-7-dimethylaminomethyl-cycloheptanol 1-benzyl-2-benzylidene-7-dimethylaminomethyl-cycloheptanol 2-benzylidene-7-dimethylaminomethyl-1-(4-fluoro-3-methylphenyl)-cycloheptanol 2-benzylidene-7-dimethylaminomethyl-1-o-tolyl-cycloheptanol 2-benzylidene-7-dimethylaminomethyl-1-vinyl-cycloheptanol 2-benzylidene-1-(4-tert.-butylphenyl)-7-dimethylamino-methyl-cycloheptanol 2-benzylidene-1-cyclopentyl-7-dimethylaminomethyl-cycloheptanol 2-benzylidene-7-dimethylaminomethyl-1-m-tolyl-cycloheptanol 2-benzylidene-1-cyclohexyl-7-dimethylaminomethyl-cycloheptanol 2-benzylidene-7-dimethylaminomethyl-1-(4-fluorophenyl)-cycloheptanol 2-benzylidene-7-dimethylaminomethyl-1-phenylethynyl-cycloheptanol 2-benzylidene-7-dimethylaminomethyl-1-thiophen-2-yl-cycloheptanol 2-benzylidene-7-dimethylaminomethyl-1-(3-methoxyphenyl)-cycloheptanol 2-benzylidene-1-cyclohexylmethyl-7-dimethylaminomethyl-cycloheptanol 2-benzylidene-7-dimethylaminomethyl-1-(3-fluoro-4-methoxyphenyl)-cycloheptanol 2-benzylidene-7-dimethylaminomethyl-1-(3-fluorophenyl)-cycloheptanol 2-benzylidene-1-(3-chlorophenyl)-7-dimethylaminomethyl-cycloheptanol 2-benzylidene-1-(3,5-dichlorophenyl)-7-dimethylamino-methyl-cycloheptanol 2-benzylidene-7-dimethylaminomethyl-1-(4-fluorobenzyl)-cycloheptanol 2-benzylidene-7-dimethylaminomethyl-1-(4-methoxybenzyl)-cycloheptanol 2-benzylidene-7-dimethylaminomethyl-1-(3-fluorobenzyl)-cycloheptanol 2-benzylidene-7-dimethylaminomethyl-1-(2-methoxyphenyl)-cycloheptanol 2-benzylidene-7-dimethylaminomethyl-1-(2-methylbenzyl)-cycloheptanol 2-benzylidene-1-(3-chloro-4-fluorophenyl)-7-dimethylamino-methyl-cyclo-heptanol 2-benzylidene-7-dimethylaminomethyl-1-(3-trifluoromethyl-phenyl)-cycloheptanol 2-benzylidene-7-dimethylaminomethyl-1-(3-methylbenzyl)-cycloheptanol 2-benzylidene-1-(4-chlorobenzyl)-7-dimethylaminomethyl-cycloheptanol 2-benzylidene-1-(2-chloro-6-fluorobenzyl)-7-dimethylamino-methyl-cyclo-heptanol 2-benzylidene-7-dimethylaminomethyl-1-(2,5-dimethylbenzyl)-cyclo-heptanol 2-benzylidene-1-(3-chlorobenzyl)-7-dimethylaminomethyl-cycloheptanol 2-dimethylaminomethyl-7-(3-methoxybenzylidene)-1-phenyl-cycloheptanol 1-(4-chlorophenyl)-2-dimethylaminomethyl-7-(3-methoxy-benzylidene)-cycloheptanol 1-benzyl-2-dimethylaminomethyl-7-(3-methoxybenzylidene)-cycloheptanol 2-dimethylaminomethyl-1-(4-fluoro-3-methylphenyl)-7-(3-methoxy-benzylidene)-cycloheptanol 2-dimethylaminomethyl-7-(3-methoxybenzylidene)-1-o-tolyl-cycloheptanol 2-dimethylaminomethyl-7-(3-methoxybenzylidene)-1-vinyl-cycloheptanol 1-(4-tert.-butylphenyl)-2-dimethylaminomethyl-7-(3-methoxybenzylidene)-cycloheptanol 1-cyclopentyl-2-dimethylaminomethyl-7-(3-methoxy-benzylidene)-cycloheptanol 2-dimethylaminomethyl-7-(3-methoxybenzylidene)-1-m-tolyl-cycloheptanol 1-cyclohexyl-2-dimethylaminomethyl-7-(3-methoxy-benzylidene)-cycloheptanol 2-dimethylaminomethyl-1-(4-fluorophenyl)-7-(3-methoxy-benzylidene)-cycloheptanol 2-dimethylaminomethyl-7-(3-methoxybenzylidene)-1-phenethyl-cycloheptanol 2-dimethylaminomethyl-7-(3-methoxybenzylidene)-1-phenylethynyl-cycloheptanol 2-dimethylaminomethyl-7-(3-methoxybenzylidene)-1-thiophen-2-yl-cycloheptanol 2-dimethylaminomethyl-7-(3-methoxybenzylidene)-1-(3-methoxyphenyl)-cycloheptanol 2-dimethylaminomethyl-7-(3-methoxybenzylidene)-1-(3-phenylpropyl)-cycloheptanol 2-dimethylaminomethyl-7-(3-methoxybenzylidene)-1-p-tolyl-cycloheptanol 2-dimethylaminomethyl-7-(3-methoxybenzylidene)-1-(4-methoxyphenyl)-cycloheptanol 1-cyclohexylmethyl-2-dimethylaminomethyl-7-(3-methoxy-benzylidene)-cycloheptanol 1-(3-chlorophenyl)-2-dimethylaminomethyl-7-(3-methoxy-benzylidene)-cycloheptanol 1-(3,5-dichlorophenyl)-2-dimethylaminomethyl-7-(3-methoxybenzylidene)-cycloheptanol 1-(2-chlorobenzyl)-2-dimethylaminomethyl-7-(3-methoxy-benzylidene)-cycloheptanol 1-(4-chloro-3-trifluoromethylphenyl)-2-dimethylamino-methyl-7-(3-methoxybenzyl idene)-cycloheptanol 2-dimethylaminomethyl-1-(3-fluorophenyl)-7-(3-methoxybenzylidene)-cycloheptanol 2-dimethylaminomethyl-7-(3-methoxybenzylidene)-1-(2-methoxyphenyl)-cycloheptanol 2-dimethylaminomethyl-7-(3-methoxybenzylidene)-1-(2-methylbenzyl)-cycloheptanol 2-dimethylaminomethyl-7-(3-methoxybenzylidene)-1-(3-trifluoromethylphenyl)-cycloheptanol 2-dimethylaminomethyl-7-(3-methoxybenzylidene)-1-(3-methylbenzyl)-cycloheptanol 2-dimethylaminomethyl-1-(2,5-dimethylbenzyl)-7-(3-methoxybenzylidene)-cycloheptanol 1-(3-chlorobenzyl)-2-dimethylaminomethyl-7-(3-methoxy-benzylidene)-cycloheptanol 1-benzyl-2-dimethylaminomethyl-7-(4-methoxybenzylidene)-cycloheptanol 2-dimethylaminomethyl-1-(4-fluoro-3-methylphenyl)-7-(4-methoxybenzylidene)-cycloheptanol 2-dimethylaminomethyl-7-(4-methoxybenzylidene)-1-o-tolyl-cycloheptanol 2-dimethylaminomethyl-7-(4-methoxybenzylidene)-1-vinyl-cycloheptanol 1-(4-tert.-butylphenyl)-2-dimethylaminomethyl-7-(4-methoxybenzylidene)-cycloheptanol 1-cyclopentyl-2-dimethylaminomethyl-7-(4-methoxybenzylidene)-cycloheptanol 2-dimethylaminomethyl-7-(4-methoxybenzylidene)-1-m-tolyl-cycloheptanol 1-cyclohexyl-2-dimethylaminomethyl-7-(4-methoxybenzylidene)-cycloheptanol 2-dimethylaminomethyl-1-(4-fluorophenyl)-7-(4-methoxybenzylidene)-cycloheptanol 2-dimethylaminomethyl-7-(4-methoxybenzylidene)-1-phenethyl-cycloheptanol 2-dimethylaminomethyl-7-(4-methoxybenzylidene)-1-phenethynyl-cycloheptanol 2-dimethylaminomethyl-7-(4-methoxybenzylidene)-1-thiophen-2-yl-cycloheptanol 2-dimethylaminomethyl-7-(4-methoxybenzylidene)-1-(3-methoxyphenyl)-cycloheptanol 2-dimethylaminomethyl-7-(4-methoxybenzylidene)-1-(3-phenylpropyl)-cycloheptanol 2-dimethylaminomethyl-7-(4-methoxybenzylidene)-1-p-tolyl-cycloheptanol 2-dimethylaminomethyl-7-(4-methoxybenzylidene)-1-(4-methoxyphenyl)-cycloheptanol 1-cyclohexylmethyl-2-dimethylaminomethyl-7-(4-methoxy-benzylidene)-cycloheptanol 1-(3-chlorophenyl)-2-dimethylaminomethyl-7-(4-methoxy-benzylidene)-cycloheptanol 1-(2-chlorobenzyl)-2-dimethylaminomethyl-7-(4-methoxy-benzylidene)-cycloheptanol 2-dimethylaminomethyl-7-(4-methoxybenzylidene)-1-(2-methoxyphenyl)-cycloheptanol 2-dimethylaminomethyl-7-(4-methoxybenzylidene)-1-(2-methylbenzyl)-cycloheptanol 2-dimethylaminomethyl-7-(4-methoxybenzylidene)-1-(3-trifluoromethylphenyl)-cycloheptanol 2-dimethylaminomethyl-7-(4-methoxybenzylidene)-1-(3-methylbenzyl)-cycloheptanol 1-(3-chlorobenzyl)-2-dimethylaminomethyl-7-(4-methoxy-benzylidene)-cycloheptanol 1-(3,5-dichlorophenyl)-2-dimethylaminomethyl-7-(4-methoxybenzylidene)-cycloheptanol 2-benzylidene-7-dimethylaminomethyl-1-(3-hydroxyphenyl)-cycloheptanol 2-dimethylaminomethyl-1-(3-hydroxyphenyl)-7-(3-methoxy-benzylidene)-cycloheptanol 2-benzylidene-7-dimethylaminomethyl-1-(3-methoxyphenyl)-cycloheptanol 3-[1-(2-dimethylaminomethyl-1-methylethyl)-1-hydroxy-2-methyl-3-phenyl-allyl]-phenol 3-(4-chlorobenzyl)-5-dimethylamino-2,4-dimethyl-1-phenyl-pent-1-en-3-ol 5-dimethylamino-3-(3-methoxyphenyl)-2,4-dimethyl-1-phenyl-pent-1-en-3-ol 3-(2-benzylidene-6-dimethylaminomethyl-1-hydroxycyclo-hexyl)-phenol 1-benzyl-2-benzylidene-7-(4-methylpiperazin-1-ylmethyl)-cycloheptanol 2-benzylidene-1-(2-chlorobenzyl)-7-(4-methylpiperazin-1-ylmethyl)-cycloheptanol 2-benzylidene-1-(3-chlorobenzyl)-7-(4-methylpiperazin-1-ylmethyl)-cycloheptanol 2-benzylidene-1-(4-chlorobenzyl)-7-(4-methylpiperazin-1-ylmethyl)-cycloheptanol 2-benzylidene-1-(2-fluorobenzyl)-7-(4-methylpiperazin-1-ylmethyl)-cycloheptanol 2-benzylidene-1-(3-fluorobenzyl)-7-(4-methylpiperazin-1-ylmethyl)-cycloheptanol 2-benzylidene-1-(4-fluorobenzyl)-7-(4-methylpiperazin-1-ylmethyl)-cycloheptanol 2-benzylidene-1-(2-methylbenzyl)-7-(4-methylpiperazin-1-ylmethyl)-cycloheptanol 2-benzylidene-1-(3-methylbenzyl)-7-(4-methylpiperazin-1-ylmethyl)-cycloheptanol 2-benzylidene-1-(4-methylbenzyl)-7-(4-methylpiperazin-1-ylmethyl)-cycloheptanol 2-benzylidene-1-(2-methoxybenzyl)-7-(4-methylpiperazin-1-ylmethyl)-cycloheptanol 2-benzylidene-1-(3-methoxybenzyl)-7-(4-methylpiperazin-1-ylmethyl)-cycloheptanol 2-benzylidene-1-(4-methoxybenzyl)-7-(4-methylpiperazin-1-ylmethyl)-cycloheptanol 2-benzylidene-1-(2,6-dichlorobenzyl)-7-(4-methylpiperazin-1-ylmethyl)-cycloheptanol 2-benzylidene-1-(2-chloro-6-fluorobenzyl)-7-(4-methyl-piperazin-1-ylmethyl)-cycloheptanol 2-benzylidene-1-(2,6-difluorobenzyl)-7-(4-methylpiperazin-1-ylmethyl)-cycloheptanol 1-benzyl-2-(4-chlorobenzylidene)-7-(4-methylpiperazin-1-ylmethyl)-cycloheptanol 1-(2-chlorobenzyl)-2-(4-chlorobenzylidene)-7-(4-methyl-piperazin-1-ylmethyl)-cycloheptanol 1-(3-chlorobenzyl)-2-(4-chlorobenzylidene)-7-(4-methylpiperazin-1-ylmethyl)-cycloheptanol 1-(4-chlorobenzyl)-2-(4-chlorobenzylidene)-7-(4-methyl-piperazin-1-ylmethyl)-cycloheptanol 2-(4-chlorobenzylidene)-1-(2-fluorobenzyl)-7-(4-methyl-piperazin-1-ylmethyl)-cycloheptanol 2-(4-chlorobenzylidene)-1-(3-fluorobenzyl)-7-(4-methyl-piperazin-1-ylmethyl)-cycloheptanol 2-(4-chlorobenzylidene)-1-(4-fluorobenzyl)-7-(4-methyl-piperazin-1-ylmethyl)-cycloheptanol 2-(4-chlorobenzylidene)-1-(2-methylbenzyl)-7-(4-methyl-piperazin-1-ylmethyl)-cycloheptanol 2-(4-chlorobenzylidene)-1-(3-methylbenzyl)-7-(4-methyl-piperazin-1-ylmethyl)-cycloheptanol 2-(4-chlorobenzylidene)-1-(4-methylbenzyl)-7-(4-methyl-piperazin-1-ylmethyl)-cycloheptanol 2-(4-chlorobenzylidene)-1-(2-methoxybenzyl)-7-(4-methyl-piperazin-1-ylmethyl)-cycloheptanol 2-(4-chlorobenzylidene)-1-(3-methoxybenzyl)-7-(4-methyl-piperazin-1-ylmethyl)-cycloheptanol 2-(4-chlorobenzylidene)-1-(4-methoxybenzyl)-7-(4-methyl-piperazin-1-ylmethyl)-cycloheptanol 2-(4-chlorobenzylidene)-1-(2,6-dichlorobenzyl)-7-(4-methyl-piperazin-1-ylmethyl)-cycloheptanol 2-(4-chlorobenzylidene)-1-(2,6-difluorobenzyl)-7-(4-methyl-piperazin-1-ylmethyl)-cycloheptanol 2-(4-chlorobenzylidene)-1-(2-chloro-6-fluorobenzyl)-7-(4-methyl-piperazin-1-ylmethyl)-cycloheptanol 1-benzyl-2-(4-fluorobenzylidene)-7-(4-methylpiperazin-1-ylmethyl)-cycloheptanol 1-(2-chlorobenzyl)-2-(4-fluorobenzylidene)-7-(4-methyl-piperazin-1-ylmethyl)-cycloheptanol 1-(3-chlorobenzyl)-2-(4-fluorobenzylidene)-7-(4-methyl-piperazin-1-ylmethyl)-cycloheptanol 1-(4-chlorobenzyl)-2-(4-fluorobenzylidene)-7-(4-methyl-piperazin-1-ylmethyl)-cycloheptanol 1-(2-fluorobenzyl)-2-(4-fluorobenzylidene)-7-(4-methyl-piperazin-1-ylmethyl)-cycloheptanol 1-(3-fluorobenzyl)-2-(4-fluorobenzylidene)-7-(4-methyl-piperazin-1-ylmethyl)-cycloheptanol 1-(4-fluorobenzyl)-2-(4-fluorobenzylidene)-7-(4-methyl-piperazin-1-ylmethyl)-cycloheptanol 2-(4-fluorobenzylidene)-1-(2-methylbenzyl)-7-(4-methyl-piperazin-1-ylmethyl)-cycloheptanol 2-(4-fluorobenzylidene)-1-(3-methylbenzyl)-7-(4-methyl-piperazin-1-ylmethyl)-cycloheptanol 2-(4-fluorobenzylidene)-1-(4-methylbenzyl)-7-(4-methyl-piperazin-1-ylmethyl)-cycloheptanol 2-(4-fluorobenzylidene)-1-(2-methoxybenzyl)-7-(4-methyl-piperazin-1-ylmethyl)-cycloheptanol 2-(4-fluorobenzylidene)-1-(3-methoxybenzyl)-7-(4-methyl-piperazin-1-ylmethyl)-cycloheptanol 2-(4-fluorobenzylidene)-1-(4-methoxybenzyl)-7-(4-methyl-piperazin-1-ylmethyl)-cycloheptanol 1-(2,6-dichlorobenzyl)-2-(4-fluorobenzylidene)-7-(4-methyl-piperazin-1-ylmethyl)-cycloheptanol 1-(2,6-difluorobenzyl)-2-(4-fluorobenzylidene)-7-(4-methyl-piperazin-1-ylmethyl)-cycloheptanol 1-(2-chloro-6-fluorobenzyl)-2-(4-fluorobenzylidene)-7-(4-methylpiperazin-1-ylmethyl)-cycloheptanol 1-benzyl-2-furan-2-ylmethylene-7-(4-methylpiperazin-1-ylmethyl)-cycloheptanol 1-(2-chlorobenzyl)-2-furan-2-ylmethylene-7-(4-methyl-piperazin-1-ylmethyl)-cycloheptanol 1-(3-chlorobenzyl)-2-furan-2-ylmethylene-7-(4-methyl-piperazin-1-ylmethyl)-cycloheptanol 1-(4-chlorobenzyl)-2-furan-2-ylmethylene-7-(4-methyl-piperazin-1-ylmethyl)-cycloheptanol 1-(2-fluorobenzyl)-2-furan-2-ylmethylene-7-(4-methyl-piperazin-1-ylmethyl)-cycloheptanol 1-(3-fluorobenzyl)-2-furan-2-ylmethylene-7-(4-methyl-piperazin-1-ylmethyl)-cycloheptanol 1-(4-fluorobenzyl)-2-furan-2-ylmethylene-7-(4-methyl-piperazin-1-ylmethyl)-cycloheptanol 2-furan-2-ylmethylene-1-(2-methylbenzyl)-7-(4-methyl-piperazin-1-ylmethyl)-cycloheptanol 2-furan-2-ylmethylene-1-(3-methylbenzyl)-7-(4-methyl-piperazin-1-ylmethyl)-cycloheptanol 2-furan-2-ylmethylene-1-(4-methylbenzyl)-7-(4-methyl-piperazin-1-ylmethyl)-cycloheptanol 2-furan-2-ylmethylene-1-(2-methoxybenzyl)-7-(4-methyl-piperazin-1-ylmethyl)-cycloheptanol 2-furan-2-ylmethylene-1-(3-methoxybenzyl)-7-(4-methyl-piperazin-1-ylmethyl)-cycloheptanol 2-furan-2-ylmethylene-1-(4-methoxybenzyl)-7-(4-methyl-piperazin-1-ylmethyl)-cycloheptanol 1-(2,6-dichlorobenzyl)-2-furan-2-ylmethylene-7-(4-methyl-piperazin-1-ylmethyl)-cycloheptanol 1-(2,6-difluorobenzyl)-2-furan-2-ylmethylene-7-(4-methyl-piperazin-1-ylmethyl)-cycloheptanol 1-(2-chloro-6-fluorobenzyl)-2-furan-2-ylmethylene-7-(4-methylpiperazin-1-ylmethyl)-cycloheptanol 1-benzyl-3-furan-2-ylmethylene-7-(4-methylpiperazin-1-ylmethyl)-cycloheptanol 1-(2-chlorobenzyl)-3-furan-2-ylmethylene-7-(4-methyl-piperazin-1-ylmethyl)-cycloheptanol 1-(3-chlorobenzyl)-3-furan-2-ylmethylene-7-(4-methyl-piperazin-1-ylmethyl)-cycloheptanol 1-(4-chlorobenzyl)-3-furan-2-ylmethylene-7-(4-methyl-piperazin-1-ylmethyl)-cycloheptanol 1-(2-fluorobenzyl)-3-furan-2-ylmethylene-7-(4-methyl-piperazin-1-ylmethyl)-cycloheptanol 1-(3-fluorobenzyl)-3-furan-2-ylmethylene-7-(4-methyl-piperazin-1-ylmethyl)-cycloheptanol 1-(4-fluorobenzyl)-3-furan-2-ylmethylene-7-(4-methyl-piperazin-1-ylmethyl)-cycloheptanol 3-furan-2-ylmethylene-1-(2-methylbenzyl)-7-(4-methyl-piperazin-1-ylmethyl)-cycloheptanol 3-furan-2-ylmethylene-1-(3-methylbenzyl)-7-(4-methyl-piperazin-1-ylmethyl)-cycloheptanol 3-furan-2-ylmethylene-1-(4-methylbenzyl)-7-(4-methyl-piperazin-1-ylmethyl)-cycloheptanol 3-furan-2-ylmethylene-1-(2-methoxybenzyl)-7-(4-methyl-piperazin-1-ylmethyl)-cycloheptanol 3-furan-2-ylmethylene-1-(3-methoxybenzyl)-7-(4-methyl-piperazin-1-ylmethyl)-cycloheptanol 3-furan-2-ylmethylene-1-(4-methoxybenzyl)-7-(4-methyl-piperazin-1-ylmethyl)-cycloheptanol 1-(2,6-dichlorobenzyl)-3-furan-2-ylmethylene-7-(4-methyl-piperazin-1-ylmethyl)-cycloheptanol 1-(2,6-difluorobenzyl)-3-furan-2-ylmethylene-7-(4-methyl-piperazin-1-ylmethyl)-cycloheptanol, and 1-(2-chloro-6-fluorobenzyl)-3-furan-2-ylmethylene-7-(4-methyl-piperazin-1-ylmethyl)-cycloheptanol.

27. A physiologically acceptable salt of a compound according to claim 26.

28. A hydrate of a compound according to claim 26.

29. A hydrochloride or dihydrochloride of a compound according to claim 26.

30. An E isomer of a compound according to claim 1, wherein the E isomer is as shown in formula I':

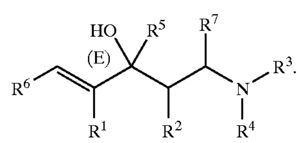

31. A compound according to claim 1, wherein $R^7$ is hydrogen and $R^1$ and $R^2$ together form a ring, and the OH group and the aminomethylene group $CHR^7—NR^3R^4$ according to formula I are in the cis position relative to one another, as shown in formula I":

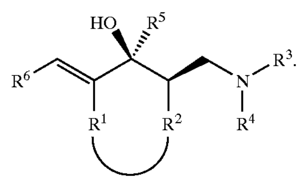

32. A pharmaceutical composition comprising at least one compound according to claim 1, and a pharmaceutically suitable excipient.

33. A pharmaceutical composition according to claim 32, wherein the compound is present as a pure diastereomer, a pure enantiomer, a racemate, a non-equimolar mixture of diastereomers, an equimolar mixture of diastereomers, or an non-equimolar mixture of enantiomers.

34. A process for the production of a compound according to claim 1, the process comprising reacting a β-aminoketone of formula IA, in which $R^1$ to $R^4$, $R^6$ and $R^7$ are as defined for formula I

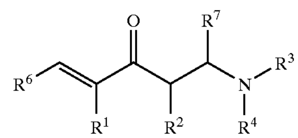

with an organometallic compound of formula III $$R^5—Z \qquad \text{III}$$

in which Z denotes MgCl, MgBr, MgI or Li and $R^5$ is as defined for formula I, to form a compound of the formula I.

* * * * *